US008262991B2

(12) United States Patent
Carlsen et al.

(10) Patent No.: US 8,262,991 B2
(45) Date of Patent: Sep. 11, 2012

(54) APPARATUS FOR ANALYSING FLUID TAKEN FROM A BODY

(75) Inventors: Thomas Nikolai Carlsen, Copenhagen (DK); Peter Christiansen, Lyngby (DK); Kristjan Freyr Gudmundsson, Ballerup (DJ); Frederik Nikolaj Svaerke Sonnenborg, Jyllinge (DK)

(73) Assignee: Lattec I/S, Hillerod (DK)

( * ) Notice: Subject to any disclaimer, the term of this patent is extended or adjusted under 35 U.S.C. 154(b) by 1337 days.

(21) Appl. No.: 10/848,603

(22) Filed: May 19, 2004

(65) Prior Publication Data

US 2005/0003522 A1    Jan. 6, 2005

Related U.S. Application Data

(60) Provisional application No. 60/476,647, filed on Jun. 9, 2003, provisional application No. 60/549,149, filed on Mar. 3, 2004.

(30) Foreign Application Priority Data

May 19, 2003 (DK) .................................. 2003 00751
Mar. 3, 2004 (DK) .................................. 2004 00358

(51) Int. Cl.
    *G01N 21/00* (2006.01)
(52) U.S. Cl. ................ 422/63; 422/64; 422/65; 422/67; 436/180
(58) Field of Classification Search .............. 422/63–65, 422/67, 99–100, 500–502; 436/180
See application file for complete search history.

(56) References Cited

U.S. PATENT DOCUMENTS

| 4,152,390 A | 5/1979 | Nosco et al. |
| 4,187,077 A | 2/1980 | Covington et al. |
| 4,219,529 A | 8/1980 | Tersteeg et al. |

(Continued)

FOREIGN PATENT DOCUMENTS

DE    197 06 520 A1    8/1998

(Continued)

OTHER PUBLICATIONS

Notification of Transmittal of the International Search Report and The Written Opinion of the International Searching Authority, or the Declaration mailed Mar. 4, 2005, in PCT/DK2004/000355 including International Search Report and Written Opinion.

*Primary Examiner* — Jyoti Nagpaul
(74) *Attorney, Agent, or Firm* — Stephen A. Bent; Foley & Lardner LLP

(57) ABSTRACT

The present invention relates generally to an apparatus for analysing fluid taken from a body, and more in particularly for analysing body fluids from mammals. The analysis apparatus is coupled to a dairy system for milking of cows, wherein it may be useful to analyse the status of the milk. The apparatus is preferably located as early as possible in the production chain in order to obtain results as close as possible to the cows. Hence the environment in which the apparatus is to be used may be harsh towards internal apparatus modules or consumables, therefore the apparatus is isolated and the internal environment is conditioned regarding humidity, temperature as well as the amount of ammonium. Furthermore the steps for analysing milk is automated inside the apparatus in order to avoid influence from the external environment.

15 Claims, 71 Drawing Sheets
(64 of 71 Drawing Sheet(s) Filed in Color)

U.S. PATENT DOCUMENTS

| | | | |
|---|---|---|---|
| 4,224,032 A | | 9/1980 | Glover et al. |
| 4,296,069 A | | 10/1981 | Smith et al. |
| 4,296,070 A | | 10/1981 | Montalto et al. |
| 4,298,571 A | | 11/1981 | DiFulvio et al. |
| 4,320,757 A | | 3/1982 | Whitney et al. |
| 4,387,990 A | | 6/1983 | Yazawa et al. |
| 4,419,871 A | | 12/1983 | Zonco et al. |
| 4,512,952 A | | 4/1985 | Blanding et al. |
| 4,568,519 A | | 2/1986 | Hamilton et al. |
| 4,708,886 A | | 11/1987 | Nelson |
| 4,892,830 A | | 1/1990 | Findley et al. |
| 4,919,887 A | * | 4/1990 | Wakatake ............... 422/67 |
| 5,037,613 A | | 8/1991 | Shaw et al. |
| 5,043,143 A | | 8/1991 | Shaw et al. |
| 5,075,079 A | | 12/1991 | Kerr et al. |
| 5,089,418 A | | 2/1992 | Shaw et al. |
| 5,169,787 A | | 12/1992 | Knappe et al. |
| 5,173,261 A | | 12/1992 | Krause et al. |
| 5,174,960 A | | 12/1992 | Shaw et al. |
| 5,192,506 A | * | 3/1993 | Kureshy et al. ............ 422/64 |
| 5,192,693 A | | 3/1993 | Yazawa et al. |
| 5,196,168 A | | 3/1993 | Muszak et al. |
| 5,244,632 A | | 9/1993 | Shaw et al. |
| 5,250,262 A | | 10/1993 | Heidt et al. |
| 5,258,163 A | | 11/1993 | Krause et al. |
| 5,284,622 A | | 2/1994 | Krause et al. |
| 5,330,716 A | | 7/1994 | Shaw et al. |
| 5,408,535 A | | 4/1995 | Howard, III et al. |
| 5,419,871 A | | 5/1995 | Muszak et al. |
| 5,578,269 A | * | 11/1996 | Yaremko et al. ............ 422/64 |
| 5,660,793 A | | 8/1997 | Seto et al. |
| 5,889,585 A | | 3/1999 | Markart |
| 5,989,917 A | * | 11/1999 | McAleer et al. ............ 436/46 |
| 6,151,110 A | | 11/2000 | Markart |
| 6,228,636 B1 | | 5/2001 | Yahiro et al. |
| 6,264,891 B1 | | 7/2001 | Heyneker et al. |
| 6,458,596 B1 | | 10/2002 | Poellmann |
| 6,524,845 B1 | | 2/2003 | Markart et al. |
| 6,551,558 B1 | | 4/2003 | Mann et al. |
| 7,182,911 B1 | | 2/2007 | Komatsu |
| 2002/0114733 A1 | | 8/2002 | Copeland et al. |

FOREIGN PATENT DOCUMENTS

| | | |
|---|---|---|
| DE | 198 22 770 A1 | 11/1999 |
| EP | 0 042 338 B1 | 12/1981 |
| EP | 0 042 339 B1 | 12/1981 |
| EP | 0 042 340 B1 | 12/1981 |
| EP | 0 098 773 B1 | 1/1984 |
| EP | 0 148 203 B1 | 7/1985 |
| EP | 0 388 168 B1 | 9/1990 |
| EP | 0 397 255 B1 | 11/1990 |
| EP | 0 397 256 B1 | 11/1990 |
| EP | 0 449 100 B1 | 10/1991 |
| EP | 0 487 149 B1 | 5/1992 |
| EP | 0 511 120 A1 | 10/1992 |
| EP | 0 550 091 A1 | 7/1993 |
| EP | 0 585 595 A2 | 3/1994 |
| EP | 0 679 895 B1 | 11/1995 |
| EP | 0 634 659 B1 | 6/1997 |
| JP | 06308132 | 11/1994 |
| JP | 11094842 | 4/1999 |
| JP | 11211730 | 8/1999 |
| WO | 99/57561 | 11/1999 |
| WO | 03/006997 | 1/2003 |
| WO | 2004/034063 A2 | 4/2004 |

* cited by examiner

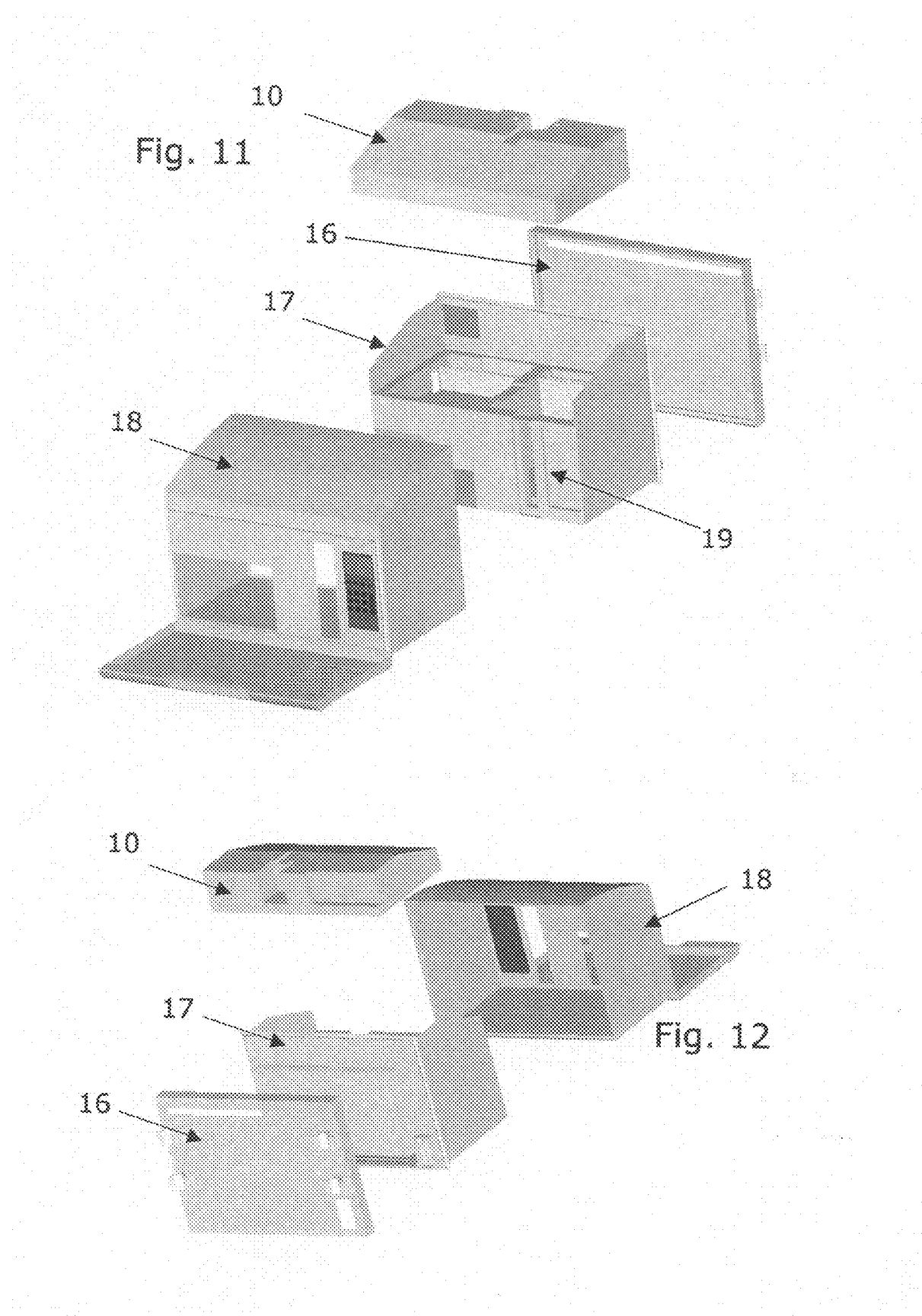

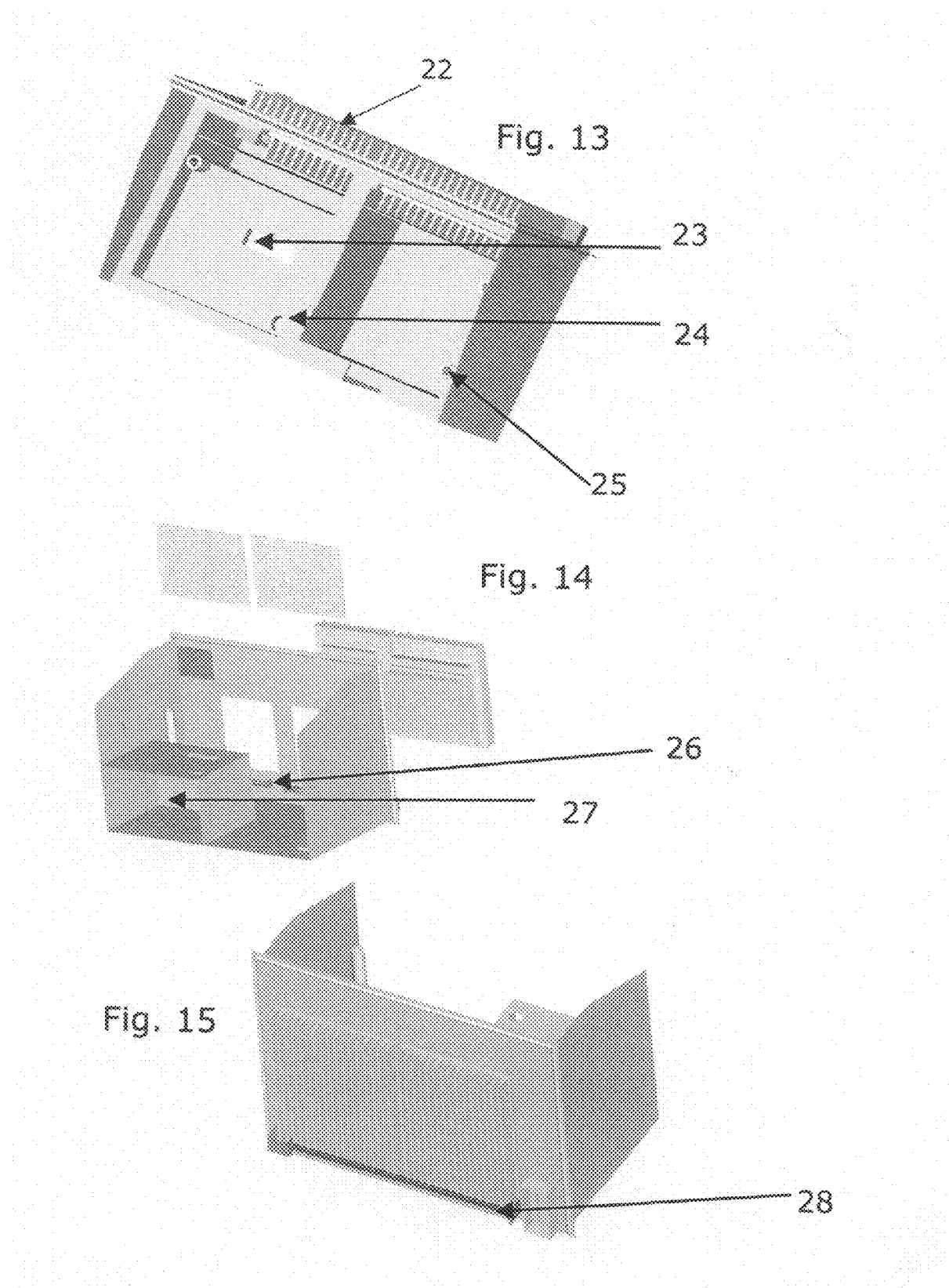

2 EMBODIMENT 43    44    45

35

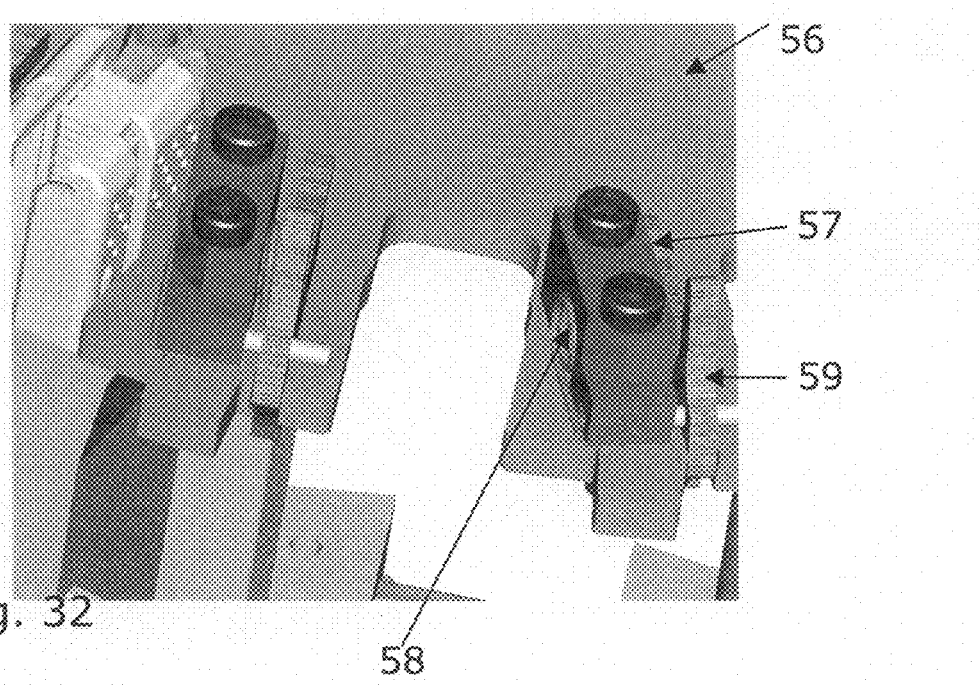
Fig. 32
Fig. 33
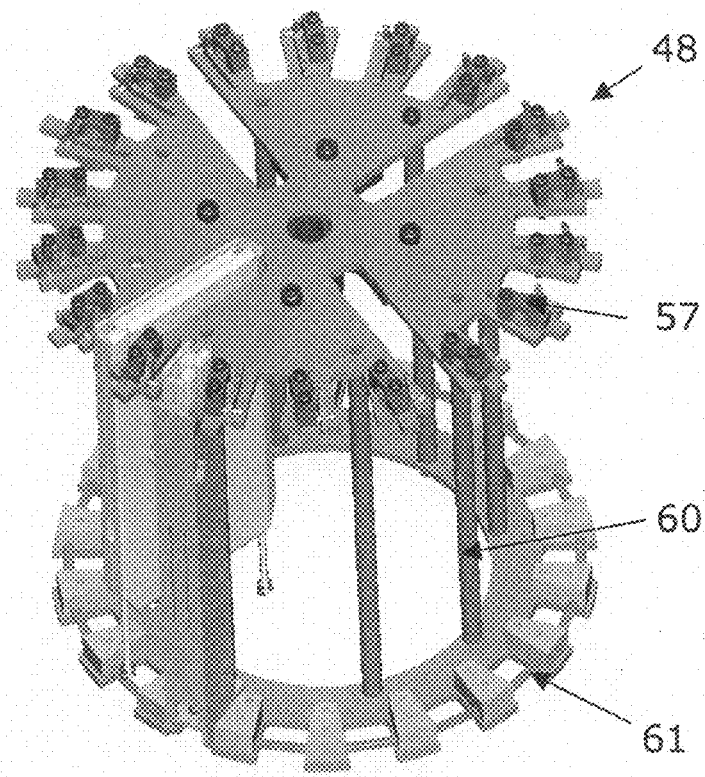

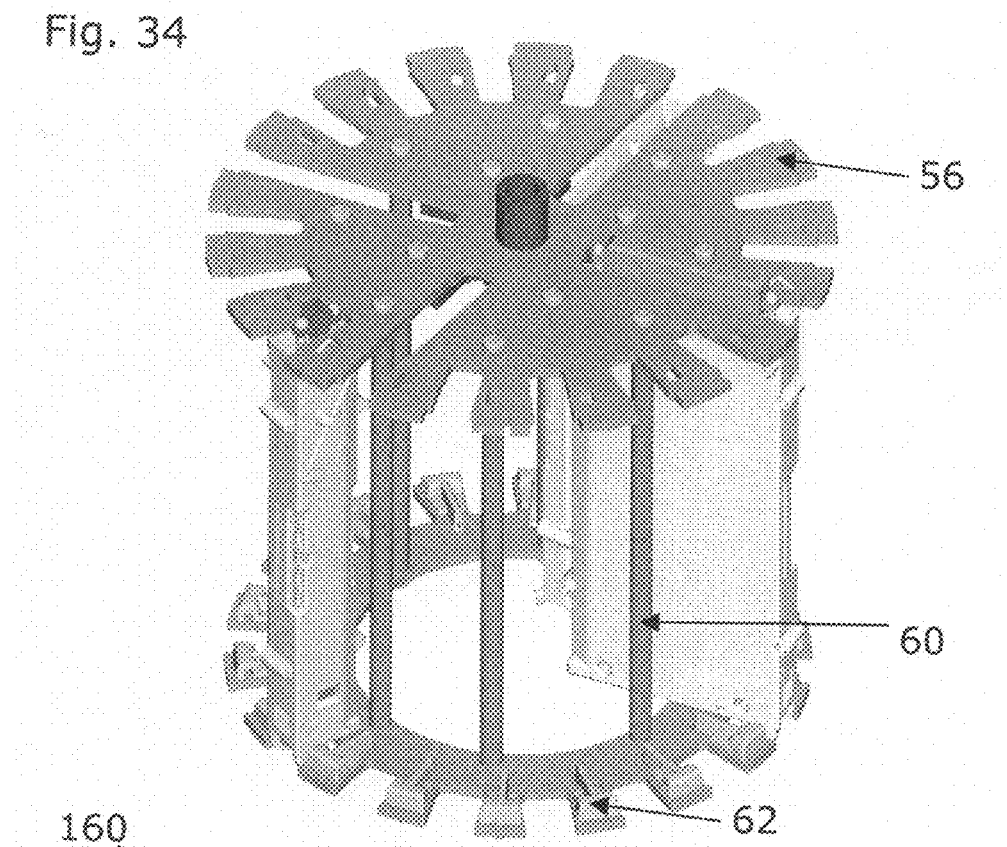
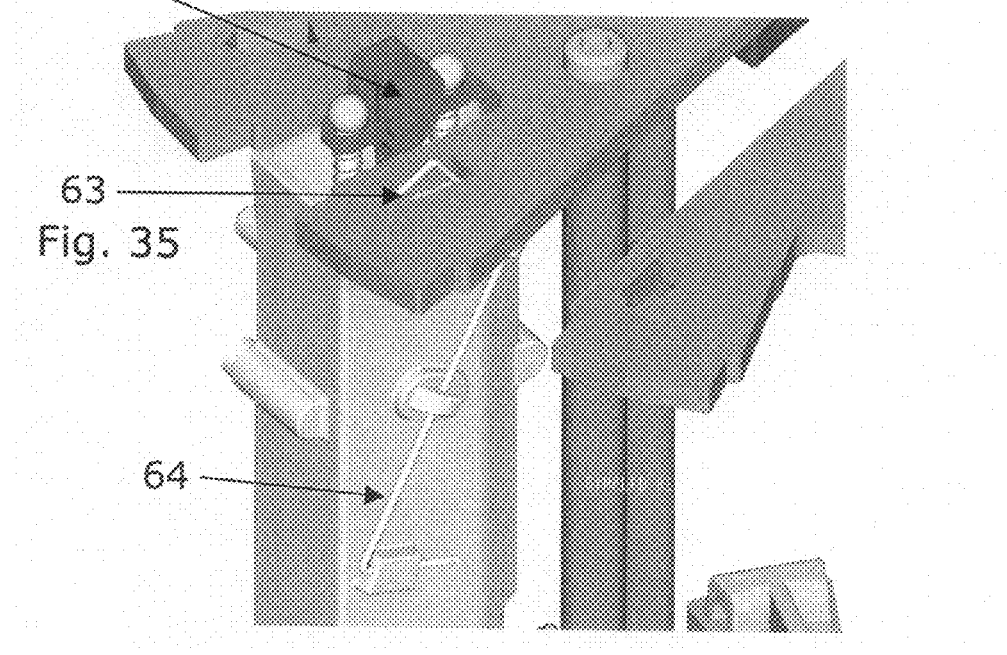

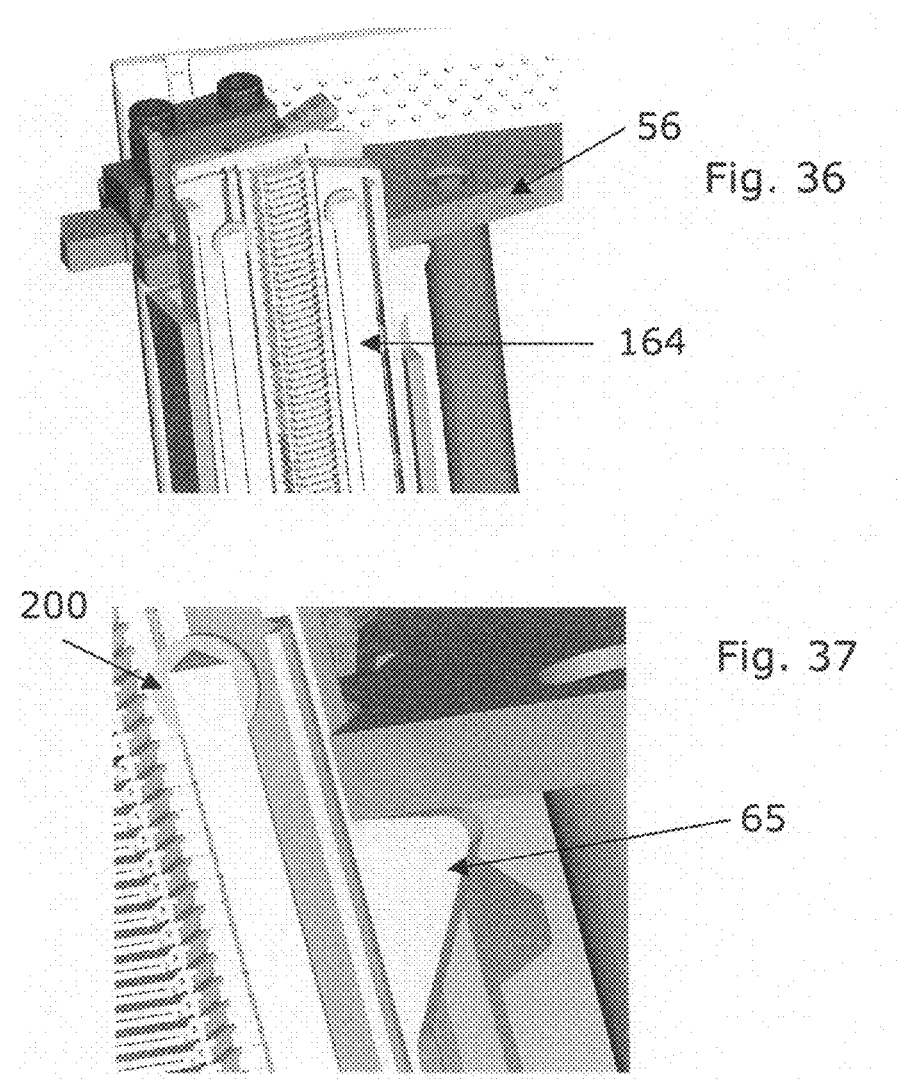

INCUBATOR

Incubator

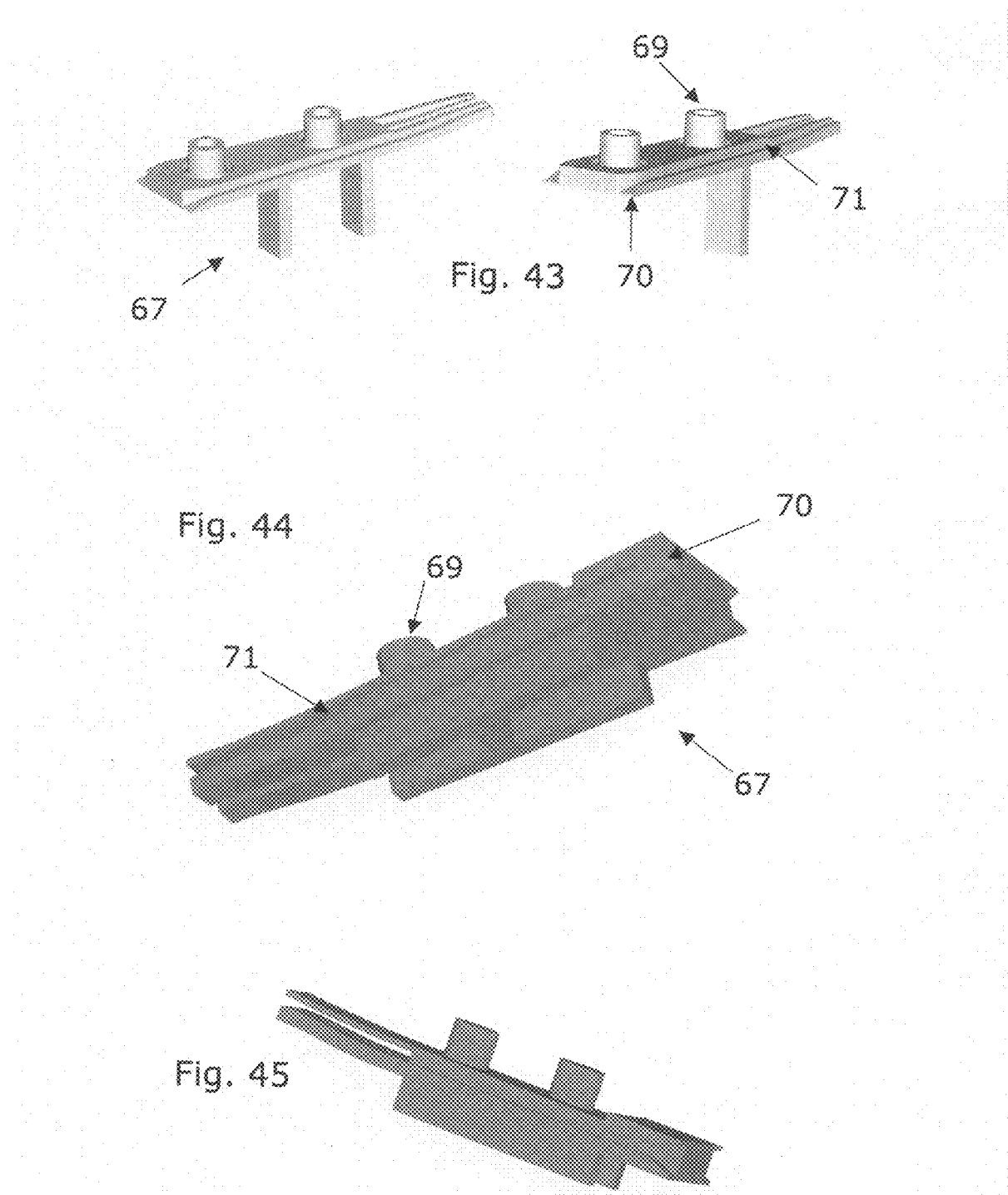

Wet system

Fig. 74a
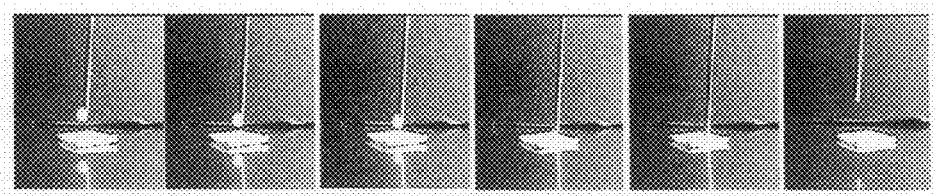
Fig. 74b
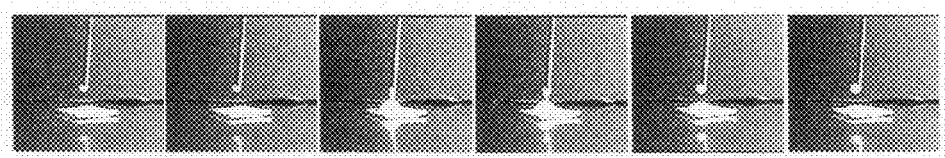
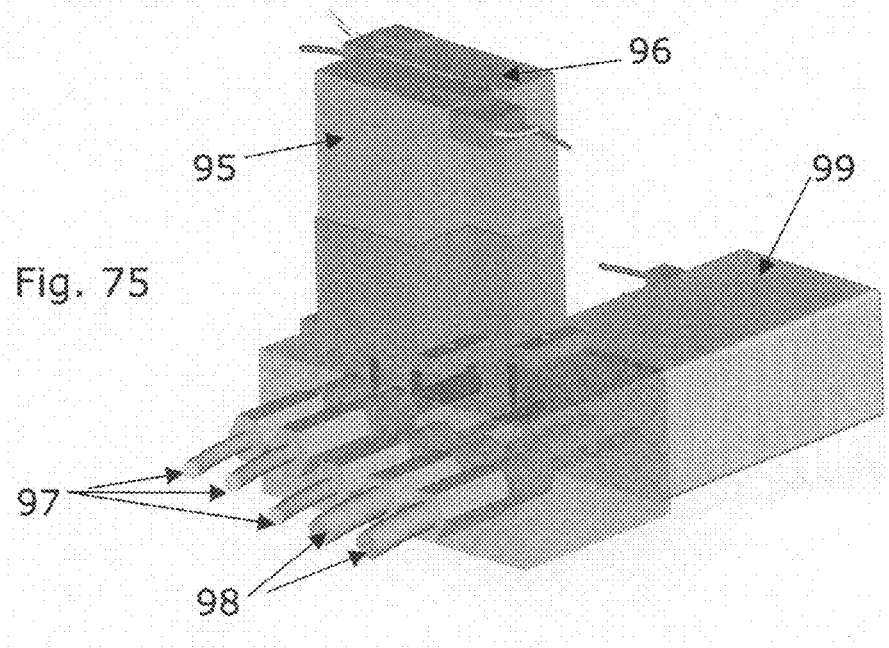
Fig. 75

RELOAD HATCH

COOLING SYSTEM

CARTRIDGE HOLDER

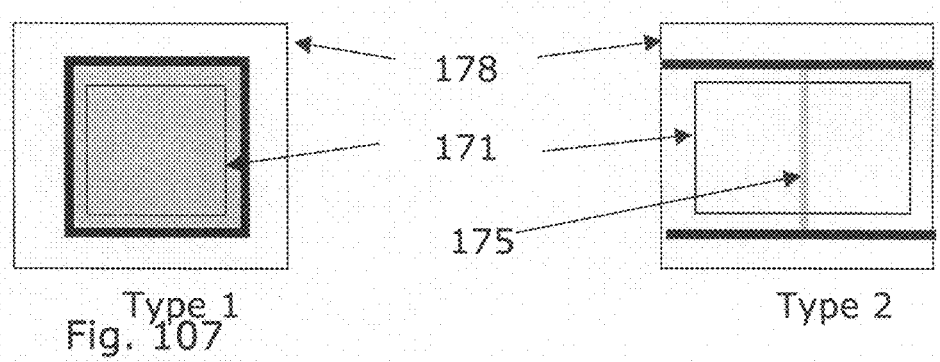
Fig. 107  Type 1    Type 2
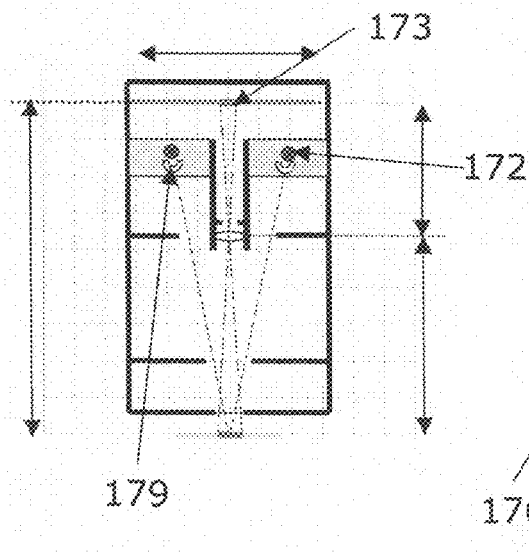
Fig. 108
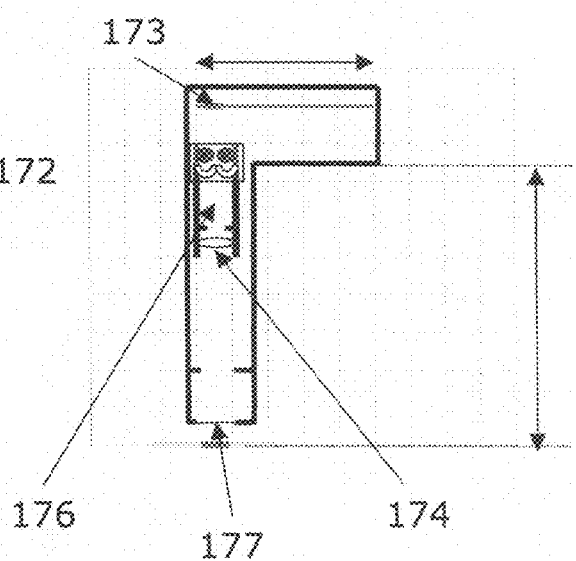
Fig. 109

APPARATUS FOR ANALYSING FLUID TAKEN FROM A BODY

CROSS-REFERENCE TO RELATED APPLICATIONS

We claim the benefit of priority of the following applications, the contents of which are incorporated herein by reference: Danish Patent Applications PA 2003 00751, filed 19 May 2003, and PA 2004 00358, filed 3 Mar. 2004; and U.S. Provisional Patent Applications 60/476,647, filed 9 Jun. 2003 and 60/549,149, filed 3 Mar. 2004.

FIELD OF THE INVENTION

The present invention relates generally to an apparatus for analysing fluid taken from a body, and more in particularly for analysing body fluids from mammals. The apparatus provides an automated analysis of milk. The invention further relates to a method for performing an analysis of body fluids.

BACKGROUND

In recent years analysis instruments have been used in the dairy industry for optimising the production and for quality assurance at all stages along the production line at the dairies. The analysis instruments are usually installed in special analysing rooms where the environment usually is not so harsh to the equipment or the biosensors that are needed in the process.

Performing the analysis late in the production process may results in many problems for the reason that if a milk sample is bad it already have been mixed in a larger batch and thus the whole batch might have to be wasted due to this. Moreover storage space and transportation space is wasted because of transportation of bad milk, thus the logistic is not as effective as it could be.

Countermeasures can be raised earlier if a milk sample turns out to be bad. Furthermore it is easier and faster to pinpoint the exact source of the bad milk sample.

Furthermore it is possible to find the animal producing the bad milk sample and at an early stage treat the animal for decease's causing the bad milk sample. Thus it is possible to prevent development of for example mastitis or other illnesses that may result in a lower production of milk.

Therefore many advantages could be achieved by installing an analysis apparatus as close to the source of milk to be analysed as possible.

An installation on sites where the environment is harsh could have crucial impact on the analysis result. However a lot of advantages may be achieved by installing an analysis apparatus as close to the source of fluid to be analysed as possible.

For the latter kind of apparatus it is a problem to keep the whole apparatus, and more specifically the sensitive parts inside, separated from environmental influence. Without loosing processing speed or result in high investment costs in the system to which the analysis apparatus should be installed to.

BRIEF DESCRIPTION OF THE INVENTION

Therefore the present invention addresses the above-described problems and hence provides a solution wherein it is possible to achieve different internal environment(s) inside an analysis apparatus compared to the environment wherein the analysis apparatus is located. Furthermore it may be possible to achieve even two or more different internal environments. The internal environments may also be different from each other.

Preferred embodiments of the apparatus comprise storage for storing sticks or other kinds of biosensors, an incubator and transferring means for moving sticks from storage to incubator. The incubator comprises an incubator transport, for example an incubator disc on which the sticks are to be loaded. During one transportation cycle of the incubator transport, for example during one rotation of the incubator disc the apparatus performs the steps of loading the sticks on to the incubator disc, thermal conditioning of the sticks, dosing of the body fluid, incubation of the sticks carrying the body fluid and analysing the result. Finally the sticks are automatically removed from the incubator disc into a waste container.

As presented above the present invention relates to an apparatus for analyzing chemical contents in a body fluid sample.

A preferred embodiment, which will be disclosed in sections below, embodies in general the following step:
  a specific volume of a sample of the body fluid is dosaged on a drystick.
  the drystick with dosaged fluid is incubated for a certain time, and
  the result (intensity of color on the stick) is preferably measured by an optical reader.

In this application some specific terms are used, below follows a brief description of these.

The main parts of the apparatus are preferably:
  A Storage: Preferably a cylindrical storage for drysticks containing two or more different formats of drysticks, stored at controlled temperature and humidity. Means for loading sticks in cartridges into the storage and for presenting sticks to a stickmover. However the storage may also be organised as linear or matrix storage.
  A stickmover, able of transferring sticks of different format from the storage to an incubator.
  An incubator: Preferably a circular incubator receiving sticks from storage, transferring sticks to dosage and reader. However the incubator may also be organised for linear or matrix storage during incubation of sticks.
  A dosage system receiving the sample, preferably thermostating the sample and dosing the sample on the drystick. Furthermore the dosing system preferably adds additional fluids to the stick.
  Preferably two insulating enclosures insulating storage and incubator towards environment and each other, and minimizing the exchange of humidity and harmful gases with the environment and each other. A third insulation enclosure for electronics, separating the electronics from storage and incubator in order to minimize heat flow from the electronics, and separating the electronics from the environment temperature, humidity and harmful gases.
  A thermostation system securing a fixed temperature in storage and incubator.
  A humidity control system securing a low humidity level in storage.
  A cabinet protecting against moisture, water and dust.

Preferred features and effects which are envisaged obtainable by preferred embodiments of the invention are presented in the following lists:
  Storage carrousel and reload hatch
  A system enabling a precise positioning of a cartridge in relation to a storage disc, allowing the locking and releasing of the cartridge and a cartridge keeper and a rotation/translation of the same presenting the cartridge for removal/insertion, the actuating system being out of physical contact with the storage/keeper/cartridge during the storage operation.

A circular or linear storage, able of storing different sizes of dry sticks and by a linear or circular movement presenting the drysticks to a transfer mechanism.

A geometry in the storage carrousel fixing the cartridge in a precise position.

An integration of positioning detection blades in the top-disc of the storage, minimizing the tolerances between cartridge and detection blades, enabling a precise positioning of a cartridge in front of the transfer mechanism.

A reload hatch for accessing the storage room from the side of the storage carrousel, with a mechanism enabling the locking and releasing of a drystick cartridge and a cartridge keeper mounted to the storage geometry. The keeper and cartridge are preferably not in physical contact with the reload hatch during normal operation of the storage.

A cartridge keeper able of receiving a user loaded, or automatic loaded cartridge, comprising drysticks, and in cooperation with a mechanism, e.g. in a reload hatch, and the geometry of the storage, precisely positioning and locking the cartridge.

A mechanism in the cartridge keeper pushing the sticks towards the top or the bottom of the cartridge, presenting the sticks to a stickmover.

A lock in the cartridge keeper, positioning the cartridge in a first position, from where the keeper with cartridge can be loaded into a position close to locked position.

A mechanism in the cartridge keeper, preferably a spring-loaded piston, allowing a further positioning of the cartridge in the keeper, enabling a geometry on the cartridge to engage with the geometry of the storage, the same mechanism securing the position of the cartridge in relation to the geometry of the storage.

A protrusion in the cartridge keeper enabling a locking of the keeper to the reload hatch, from a certain opening position of the reload hatch, enabling a secure removal and insertion of cartridges.

A mechanism in the cartridge keeper, preferably a spring, engaging with the storage, locking the keeper to the storage.

A mechanism moving the cartridge keeper to a position where a cartridge can be loaded, when the keeper and cartridge are released from the storage disc, e.g. a spring actuated revolving movement around the front bottom corner of the cartridge keeper.

A mechanism in the reload hatch and reload hatch frame actuated by the opening of same hatch or by another actuator. When opening the reload hatch the mechanism engages with the cartridge keeper spring, which releases the keeper. This actuation releases the keeper comprising the cartridge, which will move to a position where the cartridge can be removed.

The use of a molecular sieve in an analyser for body fluids, to dry the air and remove ammonia (NH3) and hydrogen sulphide (H2S) from the air in the storage where the drysticks are stored.

The molecular sieve material being contained in a container similar to the drystick cartridges, enabling the insertion and removal of the molecular sieve in the storage, in a similar manner as the drystick cartridges.

The use of a molecular sieve in an instrument placed in an environment where the air contains H2S and/or NH3, for protecting electronics against corrosion Incubator disc A disc with 'teeth' around the periphery allowing a stickmover pawl to insert drysticks of different lengths at optional radial position on the disc. Additionally allowing the stickmover to remove the drysticks from the disc.

An element called a slot, mounted to the disc, forming a guide for the movement of the stick, and a precise positioning of the stick in the vertical and tangential direction. A lock element, preferably a spring, e.g. as part of the slot geometry, fixing the stick in the radial direction, when not pushed by the stickmover, and securing physical contact between the stick and the surface of the disc, or a surface of the slot with preferably a precisely defined distance to the bottom surface of the disc.

The removal of the stick from the slot, by pushing the stick and letting the stick, in a free fall, reach a stick waste container.

Detection blades as part of the slot, used together with photosensors to position the incubator disc in front of the transfer mechanism.

The removal of used sticks from the incubator, preferably by pushing the used stick by a new stick being inserted at the same place in the incubator.

Drives for storage and incubator

Stepmotor and positioning sensors preferably placed on one mounting rig, making it possible to make a calibration of the drive system before mounting it to the AI. The major part of the tolerances in the tangential positioning of the carrousels will be added by the positioning sensors and the placement of these in relation to the discs. By measuring an individual calibration value for the sensors that can be used in the HW/SW positioning of the stepmotors this part of the tolerance chain may be sorted out.

Stick waste container and chute leading to the waste container

A sliding hatch/fane placed before or in the chute leading to the container or in the container. The fane interacting with a sensor in the open position and another sensor in the closed position, giving the possibility to detect a drystick obstructing the fanes movement. The fane is preferably driven by a mechanism (motor with crankshaft and spring) allowing the fane to stop in a position between open and closed, if obstructed by a drystick.

The hatch/fane minimizing the airflow between waste container and incubator.

A control strategy for stickwaste detection.

Stickmover

A mechanism able of transferring a drystick from the storage to the incubator in a linear motion, by a pawl pushing the stick. A geometry of the pawl in combination with a springloaded guidance of the pawl and a guiding ramp on the cartridge, securing a precise grip on the drystick and an adaption to tolerances in the positioning of cartridge, sticks, storage carrousel and stickmover guideway.

A guidance of the pawl, lifting it as it retracts after delivering a drystick to the incubator, allowing it to pass above the cartridges in the storage, in its movement towards the home position.

The pawls linear motion is preferably driven by a teeth rack or a spindle.

A hatch opened by the passing pawl system, minimizing the air and heat transfer between storage and incubator.

Control strategy for storage, incubator and stickmover

A strategy for the control of the stickmover, the storage carrousel and the incubator, enabling a precise positioning during normal operation, and a safe restart after power failure.

A protection of the mechanical systems by a surveyance of the signals from the sensors, making it possible to stop the stepmotors if e.g. a drystick is stuck in a guidance.

A positioning of the stepmotors, at normal operation, by counting steps from a home position detected by a photosensor, preferably the number of steps being calculated on basis of an individual calibration value for the photosensor, making additionally position feedback unnecessary.

Storage and incubator:

At least two photosensors and a detection blade for each position in the storage. At normal operation a detection blade at a position ahead of the desired stop position for the storage/incubator, is detected by the photosensor, and the precise stop position is obtained by counting the steps on the stepmotor driving the storage/incubator carrousel, from the detection blade to stop position. During restart from power failure the two or more photosensors are used together with at least two detection blades, to detect whether the storage is in a position where a stick can be transferred. The photosensors being positioned in such a way that they are activated by two detection blades, at a storage position suited for sticktransport. 360° is detected by a slit in the disc, a blade on the disc or a hall element.

Stickmover:

Two photosensors and three detection blades, giving the position of the stickmover (home, in or above cartridge, in guideway, in incubator). At normal operation a home detection blade is detected by the photosensor, and the precise stop position is obtained by counting the steps on the stepmotor driving the slide in the stick mover, from the home detection blade to stop position.

Beam

A suspension element positioning the mechanical systems precisely in relation to each other. Enabling a retraction from the cabinet and a fixation at a position where the mechanical systems are free of the cabinet, allowing visual inspection and repair, while the system is working.

Made of stainless steel to minimize the heat transfer between incubator and storage, or of two aluminium plates joined by steel rails.

Enabling an easy assembly and service of the mechanical modules.

Wet system

A precise dosage of a sample through a dosage needle, using another liquid dosaged by a precision pump, to push the sample through the needle.

The minimizing of carry over from a previous sample to the next sample, using the next sample to remove the previous from the tube. An enhancement of this cleaning by introducing air bubbles in the flow of the next sample, the airbubbles stopping the backflow of the sample near the tube wall. The airbubbles can additionally be used for the control of the pumps moving the samples in the tubes: The bubbles can be injected into the sample at a known position (e.g. preferably the front or the rear of the sample). The bubbles can be seen by an optical bubble detector/sensor. When the detector sees the bubbles the programmed control unit will know that e.g. the sample front is positioned at the bubble sensor. On the basis of these signals the pumps can be stopped when the sample is at a desired position in the flow system. The airbubbles can additionally be used for keeping track of the separation between a first and a second sample.

A dosage head with preferably two dosage needles, allowing dosage of a sample and another liquid, at the drystick at the same time.

A cleaning of the outside of the sample dosage needle, by flushing liquid from the other needle, with the dosage head positioned in a chamber with a geometry forcing the liquid from the other needle to surround the dosage needle. A slow controlled retraction of the needle from the cleaning chamber, while the chamber is still filled with cleaning liquid, securing that no cleaning liquid drops remains on the needle.

A dosage sequence for the dosage needles, resulting in a precise and reproducible dosage on a dry stick. The sequence being dosage at a certain height above the stick, followed by a lowering of the dosage head, letting the dosage needles touch the stick, followed by a lifting of the dosage head, the result being that remaining sample at the dosage needle tip and outside cylinder, is drawn of the needle.

The use of a bubble detector, able to distinguish between liquid and milk. The bubble detector can be used for:

Detecting the introduced air bubbles, for controlling the movement of the sample in the tubes.

Detecting the introduced airbubbles and unintended airbubbles in the sample, avoiding that these are contained in the sample volume applied to the stick.

Preferred control strategy for minimising carry-over

A method for minimising carry over in a dosage system comprising at least one dosage pump, a mainline comprising a valve and a drain, a pipe leading to a dosage unit, the dosage unit comprises at least one needle, a drain funnel and a dosage position, the method comprises the steps of:

pumping a part of a sample of the body fluid to the mainline drain, in order to clean the mainline from the previous sample, switching the valve so that a second part of the sample is directed to the pipe (dosage line) leading to the dosage unit, flushing the dosage line with a first part of the second part of the sample while the dosage needle is placed above a drain funnel, Moving the dosage needle to a narrow cavity where a second liquid is added by a second needle, the second liquid immersing and thus cleaning the needles on the outside.

Moving the needles slowly away from the narrow cavity, in order to draw the second liquid off the outside of the needles, leaving the needles with no liquid droplets, filling part of the dosage line with the second liquid so that a last part of the sample is pushed out from the needle onto a test stick.

Cabinet

A cabinet composed of three main elements:

A main cabinet part serving as suspension for the insulation house surrounding storage and incubator and electronics.

A front cabinet serving as environmental protection preferably together with the main cabinet.

A back or bottom cabinet, being part of the main cabinet, serving as environmental protection for the outer cooling ribs and fans, allowing fresh air to enter the outer cooling ribs, separating the cooling air from the instrument interior. The cooling ribs can be placed at the back or the bottom of the cabinet.

A double enclosure construction, serving as protection against humidity, NH3 and H2S, consisting of an outer protection (cabinet front and bottom) and an inner protection (insulation enclosure).

An arrangement of airguide plate, cooling rib and fan, securing a stable temperature in the incubator room.

Thermostatation sandwich

A sandwich 150 composed of an outer cooling fin 151, at least one peltier element 1521, a heat transfer bridge 155, an insulating element 153, gaskets 152, 154 and an inner cooling rib 156. The sandwich being produced as a finished unit, ready for assembly through a hole in the inner main cabinet and the insulation house. Enabling an easy mounting and dismantling of the cooling sandwich to the cabinet, without risk of damaging the sensitive peltier elements.

The invention described above preferably relates to a technical system and associated methods for analyzing body fluid.

Thus it is an object of the present invention to provide a solution that detects unwanted substances in a fluid such as milk, as close to the origin of the fluid as possible. In this way disadvantages such as, decease's among the milking animals, occupied storage space, occupied transportation space, unusable batches of fluid, difficulties in finding the source of the unusable fluid etc. may be avoided.

It is an advantage achieved by the present invention to automatically analyze the result obtained on the teststicks in order to save time.

It is further an advantage achieved by the present invention to facilitate service and to secure a more precise analyze of test sticks.

It is further an advantage achieved by the present invention to obtain a more secure result of analysis and to obtain statistics.

It is further an advantage achieved by the present invention to facilitate remote control and error detection.

It is further an advantage achieved by the present invention to facilitate the storing of cartridges, thus increasing the user-friendliness.

It is further an advantage achieved by the present invention to automatically transport teststicks between storage and an incubator in a manner, which reduce environmental influence on the test sticks.

It is further an advantage achieved by the present invention to facilitate loading and unloading, thus increasing the user-friendliness.

It is further an advantage achieved by the present invention to reduce carry-over from previous samples, thus achieving a more accurate test result.

It is further an advantage achieved by the present invention to dosage more precisely an amount of liquid on a test stick and at the same time reduce carry-over to the following sample.

It is further an advantage achieved by the present invention to facilitate removal of used teststicks in a secure manner, which reduces the environmental influence on the analysis process.

It is further an advantage achieved by the present invention to provide a solution in order to achieve at least one different internal environment compared to an outer environment.

It is further an advantage achieved by the present invention to provide a solution in order to achieve different environments within an analysis apparatus.

According to a first aspect of the invention the above object and advantages are achieved by providing an apparatus for analysing fluid taken from a body, said apparatus comprising at least one storage storing sticks and/or other kinds of biosensors to which the fluid is to be dosed, at least one incubator being distinct from the storage and transfer means for transferring sticks from the storage to the incubator.

In a second aspect of the invention, the above and other objects are fulfilled by an optical reader for reading the degree of chemical reaction found on test sticks, the optical reader comprising; at least one image sensor capable of capturing images, at least one lens, at least one memory, at least one illumination source, and a controller.

In a third aspect of the invention, the above and other objects are fulfilled by a housing for an optical reader, the housing comprises outer walls forming the housing, a front end facing a test stick and a back end, the housing further comprises; an image sensor capable of capturing still or motion images, at least one lens, and at least one opening in the outer walls for image capturing, wherein the front end comprises the at least one opening.

In a fourth aspect of the invention, the above and other objects are fulfilled by a computer system for controlling an optical reader for reading test sticks, the optical reader comprises; a first illumination source for illumination of the test sticks, a second illumination source for illumination of the test sticks, at least one lens, outer walls forming a housing, and at least one opening in the outer walls for image capturing, inner screening walls for screening off light, and a transportation mechanism for transporting test stick in to an object field, the computer system comprises; an internal bus, at least one image sensor capable of capturing still or motion images, a controller, an illumination source driver, a processor, a memory, Internal signal interface, and External signal interface, the computer system being characterised in that the controller synchronises the image capture sensor with the movement of the transportation mechanism.

In a fifth aspect of the invention, the above and other objects are fulfilled by a cartridge keeper for storing of the cartridges in a storage device, the cartridge keeper comprises: a housing defining a storing pit for a cartridge, said housing comprises: a charge opening for receiving said cartridges, a bottom, side walls, a plunger for supporting a movable bottom plate in said cartridge, at least one internal spring device for asserting a force on to the plunger, and mounting means for mounting of the cartridge keeper into the storage device.

In a sixth aspect of the invention, the above and other objects are fulfilled by a stickmover for moving a stick between two positions, the stickmover comprises a motor, at least one gearwheel, a slide, a pawl that manoeuvre the stick, a pawl lifter, and a coulisse comprising tracks for guiding of the pawl lifter, wherein the pawl and the pawl lifter is mounted to the slide by hinges.

In a seventh aspect of the invention, the above and other objects are fulfilled by a reload hatch for loading cartridges into an analysis instrument, wherein the reload hatch comprises a flipper for pushing a cartridge keeper comprising a cartridge into position in a storage carousel and a retractor for retracting the flipper.

In an eight aspect of the invention, the above and other objects are fulfilled by a method for minimising carry over in a dosage system comprising at least one dosage pump, a mainline comprising a valve and a drain, a pipe (dosage line) leading to a dosage unit, the dosage unit comprises at least one needle, a drain funnel and a dosage position, the method comprises the steps of:

pumping a part of a sample of the body fluid to the mainline drain, in order to clean the mainline from the previous sample, switching the valve so that a second part of the sample is directed to the pipe leading to the dosage unit, flushing the dosage line with a first part of the second part of the sample while the dosage needle is placed above a drain funnel, filling a part the dosage line with the second liquid so that a last part of the sample is pushed out from the needle onto a test stick.

In a ninth aspect of the invention, the above and other objects are fulfilled by a method for dosing a first liquid sample on to a test stick using a dosage pump, a second liquid and a dosage head comprising a dosage needle, the method comprises the steps of:

placing the dosage head above the stick so that there is a distance between a tip of the dosage needle and the stick, dosing the first liquid sample, lowering the dosage head, letting the tip of the dosage needle touch the stick, and lifting the dosage head, wherein the first liquid sample is pushed by the second liquid apportioned by the dosage pump.

In a tenth aspect of the invention, the above and other objects are fulfilled by a waste storage device for used sticks, the device comprising:

a container for receiving used sticks, a hatch cover, a motor for closing and opening the hatch cover, and at least one sensor, wherein the hatch cover is moved by the motor.

Furthermore the incubator in the apparatus may furthermore comprise first fluid dosing means for dosing the body fluid to be analysed to a stick. By having the dosing means in the incubator a more closed system can be achieved, hence not so sensitive to environmental influences.

The apparatus may furthermore comprising second dosing means for dosing other fluids to the sticks and/or biosensors. The second dosing means may preferably be located inside the incubator similar to the first dosing means. By having a second dosing means it is possible to apply a second fluid to the sticks and also possible to clean the first dosing means by using the second dosing means.

The apparatus may furthermore comprise thermostation means for heating and cooling of the incubator. In this way it is easier to achieve a more stable environment inside the incubator.

Furthermore the storage in the apparatus may also comprise thermostation means for heating and cooling. By having this it is easier to achieve a stable storage environment for the sticks.

It is possible to have different temperatures in the storage and incubator since the sticks may need a certain temperature for storage and another temperature in the incubator in order to react with the fluid.

The incubator may further comprise reading means for detection of a signal produced on a stick or biosensor after application of the fluid. Preferably the reading means comprises an image chip.

Furthermore the incubator may comprises stick removal means. In order to remove used sticks and make place for new sticks.

The incubator may further comprise an incubator disc comprising means for positioning, keeping and guiding sticks during the incubation. The means may also be called guiding means.

The guiding means for positioning and guiding sticks are preferably made of plastic but may be manufactured in other materials such as metal or rubber.

Preferably the means comprises a slit in the side wherein the stick is guided. In the entrance the slit may have one or two slopes in order to facilitate the insertion of a stick into the slit.

The guiding means may have two embodiments one where the stick is guided between the guiding mean and the incubator disc and one wherein the stick is guided only by the guiding mean since the slit is located a bit from the side facing the incubator disc.

Which to choose between may depend on the application in which the guiding means are to be used. In some applications the stick may adhere to the incubator disc because of static electricity. This can be avoided by guiding the stick only by the guiding means. On the other hand, using the incubator slot as part of the guiding means will give a shorter tolerance chain towards the optical reader.

Preferably the storage comprises a storage disc. By having a substantially circular storage it is easier for a user to access thus load and unload the storage from one opening.

Furthermore the storage comprises means for rotation of the storage disc. Some examples may be electric motors such as a stepmotor or the alike.

The same goes for the incubator part. The incubator is preferably rotated by an electric motor, such as a stepmotor.

The apparatus may furthermore comprise means for monitoring the number of used sticks. Such means may be different kind of sensors such as photo sensors, mechanical sensors etc.

In order to obtain a stable environment inside the storage such as conditioning of humidity content in the storage, molecular sieve or other desiccant type are preferably used.

In the same way conditioning of ammonia and hydrogen sulphide content in the storage is preferably performed in the same way such as with a molecular sieve or other desiccant type.

Preferably the molecular sieve is mounted in a cartridge for usage in the apparatus.

The apparatus preferably comprises computer means for controlling the different processes and functions such as transportation of sticks, analysis of the reaction on the stick and error alarms etc.

In order to make the analysis instrument user-friendly it preferably comprises a user interface comprising at least one of the following;

a keyboard so that a user may input values and/or instructions, a screen so that the analysis instrument can inform the user about different happenings, results or problems that may occur, a cartridge loading station for loading cartridges, so that a user can change cartridges comprising sticks or desiccants, a stickwaste container loading station, so that a user may empty the apparatus from used sticks in an efficient manner without interrupting or interfering with an analysis, a diluent container loading station, so that a user is able to change or refill diluent or change to a second liquid for any other purpose such as cleaning or the alike of the system, a liquid waste funnel cleaning station, so that the waste of a cleaning can be removed from the apparatus, and a wet system filter changing station, so that a user can change the filter.

The rotating means may be variable rotating means such as electric motors for controlling the rotation speed of the storage transport or incubator transport, preferably the storage and incubator transports are circular such as a storage disc and an incubator disc.

Furthermore the rotating means for the storage and incubator transports are step motors facilitating a precise positioning of the storage transport and incubator transport.

The storage and the incubator are preferably thermally isolated from each other and/or isolated so as to avoid or limit humidity and/or heat exchange between the storage and the incubator. In this way it is easier to keep the right storage condition in the storage wherein the sticks can be stored longer without losing their function.

In the same way it is possible to provide the right condition in the incubator wherein the sticks are supposed to react with a fluid.

In order to obtain an effective control of the condition in different parts of the apparatus a combination of thermal control, insulation, humidity-conditioning etc is preferably used.

Preferably the apparatus comprises a dosage system driven by a spindle or other linear or rotational system, for dosing body fluid at one or more locations, preferably at least at two different locations.

Furthermore the apparatus preferably comprises a protection towards the outer environment, the protection preferably comprises a main cabinet, an outer top cover and insulation enclosures, creating a double sealing.

The apparatus may comprise means for cooling and or heating such as a central conditioning system.

Preferably the apparatus comprises sensors for different functions such as sensors for checking that hatches has been closed correctly etc.

Preferably the apparatus comprises at least one sensor in the stickmover for monitoring the transferring of a stick to the incubator disc.

Preferably the apparatus comprises at least one sensor for monitoring the position of a stick in the incubator disc so that the stick is positioned correctly.

The apparatus preferably comprises tubes for transportation of fluid samples. The tubes may preferably be made of rubber or plastic or any other material suitable for transportation of fluids.

Furthermore the apparatus may comprise an air inlet valve(s) in order to provide a system for minimising carry over from a first sample to a second sample. Preferably an air pump enters air into the tubes in between samples.

Preferably the air is entered into the tubes in a last part of the first sample or in a first part of the second sample.

Furthermore the apparatus comprises pumps for moving the fluid samples in the tubes.

Preferably the apparatus comprises bubble detectors for detection of bubbles and thus for management of fluid samples.

Moreover a method is provided for analysing of fluid, which utilises an apparatus according to the invention, wherein at least one rotation of the incubator disc or incubator transport comprises the steps of:
 loading sticks into the incubator,
 dosage of fluid on to the sticks,
 incubation,
 reading, and
 removal of sticks.

The apparatus may furthermore comprise an optical reader for reading the degree of chemical reaction found on test sticks, preferably the optical reader comprises;
 at least one image sensor capable of capturing images,
 at least one lens,
 at least one memory, for storage of data,
 at least one illumination source, and
 a controller.

The apparatus may comprise a housing for an optical reader, the housing preferably comprises outer walls forming the housing, a front end facing a test stick and a back end, the housing may further comprise;
 an image sensor capable of capturing still or motion images,
 at least one lens, and
 at least one opening in the outer walls for image capturing, wherein the front end comprises the at least one opening.

The housing protects the optical reader from influence from the environment, such as light, temperature etc.

In order to control the reading of a stick, the apparatus preferably comprises a computer system for controlling an optical reader for reading test sticks. Preferably the computer system comprises;
 an internal bus,
 at least one image sensor capable of capturing still or motion images,
 a controller,
 an illumination source driver,
 a processor,
 a memory,
 Internal signal interface, and
 External signal interface, The controller preferably synchronises an image capture sensor with the movement of a transportation mechanism such as an incubator disc, stickmover or storage disc.

In order to facilitate the loading and storing of sticks into/in the apparatus, and the unloading of empty cartridges, the apparatus preferably comprises at least one cartridge keeper for storing of the cartridges in a storage device, the cartridge keeper comprises:
 a housing defining a storing pit for a cartridge, said housing comprises:
 a charge opening for receiving said cartridges,
 a bottom,
 side walls,
 a plunger for supporting a movable bottom plate in said cartridge,
 at least one internal spring device for asserting a force on to the plunger, and mounting means for mounting of the cartridge keeper into the storage device.

Furthermore the apparatus preferably comprises a stickmover for moving a stick between two positions, such as between the storage and incubator. The stickmover comprises a motor, at least one gearwheel, a slide, a pawl that manoeuvre the stick, a pawl lifter, and a coulisse comprising tracks for guiding of the pawl lifter. The pawl and the pawl lifter are preferably mounted to the slide by hinges.

The apparatus may furthermore comprise a reload hatch for loading cartridges into the apparatus, wherein the reload hatch may comprise a flipper for pushing a cartridge keeper comprising a cartridge into position in a storage carousel and a retractor for retracting the flipper.

More over the apparatus preferably comprise a waste storage device for used sticks, the storage device preferably comprises:
 a container for receiving used sticks,
 a hatch cover,
 a motor for closing and opening the hatch cover, and
 at least one sensor.

Preferably the hatch cover is connected to the motor by a spring or other flexible element so that it can flex if something gets stuck in the waste opening.

Optical Reading Module

The optical reader comprised in the apparatus or analysis instrument as described earlier, preferably comprises a movable lens. This facilitates the calibration of the system and thus makes it more user friendly.

The optical reader preferably comprising a first illumination source and a second illumination source. The illumination sources may be used depending on what kind of sticks that are to be analysed. Furthermore one stick may be read twice, first illuminated by the first source and then illuminated by the second source. This may give a more accurate reading result.

The illumination sources are preferably Light Emitting Diodes. However any other kind of light sources may be used.

Preferably the first illumination source emits light of a specific wavelength, different from the wavelength of the light of the second illumination source.

The controller preferably comprises a processor adapted to image processing, so that the processing of images is performed as fast as possible.

The memory related to the optical reader preferably comprises at least one flash memory.

Furthermore the memory preferably comprises at least one RAM and one flash memory In order to connect the different devices the apparatus preferably comprises an internal data bus to which at least the image sensor, the controller and the memory is connected.

The other devices that needs to communicate with the controller for synchronisation of reading sticks in the apparatus are preferably also connected to the controller.

The controller further comprises an illumination source driver for controlling the on/off switching of the illumination sources. Hence the illumination sources are preferably connected to the illumination source driver.

Optical Reader Housing

The optical reader housing preferably comprises a lens tube in which the lens can move back and forth. Furthermore the lens tube may comprise a second and a third lens in order to achieve more possibilities for focusing and thus change the distance between the stick to be read and the image sensor.

Preferably the housing comprises one or more illumination sources as described above.

In order to be able to have a flexible design of the optical reading housing, the housing may comprise inner screening walls. These walls make it possible to direct and/or reflect the light inside the housing so as to achieve the best illumination of the area to be illuminated.

Preferably the lens tube is mounted inline with the at least one opening in the housing and the image sensor.

The illumination sources are preferably positioned relatively to each other on opposite side of the lens tube. In order to achieve the same illumination effect on the illuminated sticks from both the illumination sources.

Preferably the illumination source is positioned so that no direct light can reach the image sensor. Preferably this may be achieved by using screening walls in order to direct and/or reflect the light.

In order to protect the devices inside the housing the at least one opening is preferably covered by a transparent membrane. In this way the electronics inside the reader housing is protected from environmental influences.

The at least one lens inside the lens tube may preferably be movable in order to facilitate calibration and user-friendliness Furthermore the housing may preferably comprise illumination sources wherein the first illumination source emits light of a specific wavelength, different from the wavelength of the light of the second illumination source.

More over the housing may comprise a filter comprising at least two colours. This embodiment can be used wherein the illumination sources emits light of the same wavelength. The filter is preferably synchronised whit the incubator through the controller so that it can change and thus illuminate the stick with a light that relates to the specific filter.

Preferably the filter may be the membrane covering the at least one opening in the housing and facing the stick to be read.

The housing may furthermore comprise reflectors for reflecting light from the illumination source towards the stick to be illuminated.

Optical Reader Computer System (Interfaces)

Furthermore the computer system described above comprises a controller for preferably controlling the illumination source driver.

The controller may synchronises the image sensor and the illumination source driver with the transportation mechanism. In order to take a photo of the sticks at the right time so that the best result is achieved. Preferably the transportation mechanism is a rotating disc.

The computer system preferably comprises a database for storage of reference objects. In this way the system can check the image taken by the image sensor and compare it with earlier taken images or reference images in order to achieve a more accurate result.

The method for reading the amount of chemical reaction found on a test stick may comprise at least some of the following steps or all of them:
    calibrating an image sensor in an optical reading module,
    synchronising the image sensor and an illumination source with a transportation mechanism,
    controlling if the transport mechanism is in a fix position,
    if the transport mechanism is in a fix position sending a request to the optical reading module,
    measuring an amount of reflected light with the image sensor,
    calculate values,
    comparing the values with a reference database, and
    returning the values to a controller,
The request sent by the transport mechanism or the incubator may comprise a specified object type and an illumination wavelength. For example the type of stick and hence which of the illumination sources that should be used, or if both the illumination sources should be used.

Storage Keepers

The cartridge keeper described above preferably comprises a spring device in the vicinity of the charge opening and mounted onto the side of one of the halves, for preferably interacting with an upper storage disc, thus holding the cartridge keeper in position in the storage device.

The cartridge keeper preferably comprises mounting means such as hinges in the vicinity of the bottom of the keeper. In this way the keeper may be tilted out from the storage mechanism such as a storage carrousel.

Furthermore the cartridge keeper may comprise retaining means for holding the cartridge in a loading position during the loading into an analysis instrument. The retaining means may be plastic protrusions mounted on a flexible part of the cartridge keeper. The protrusions preferably interacts with a slit, hole or opening in a cartridge.

Moreover the cartridge keeper may comprise at least one external spring device in the vicinity of the bottom, for providing a tilting force on to the cartridge keeper when it is mounted in a storage mechanism in an analysis instrument.

The cartridge keeper may comprise an internal bottom-stop for preventing the cartridge to be inserted too far.

Preferably the bottom-stop can move between two positions in order to push the cartridge against a bottom of a storage top disc.

The bottom-stop preferably has a cavity for receiving the plunger, and one abutment surface on each side of the cavity for abutting the cartridge when the cartridge is being stored in the storage keeper pit.

Furthermore the bottom-stop preferably comprises a cavity on the opposite side of the bottom-stop in relation to the abutment surfaces, for receiving a spring which provides the necessary force for pushing the cartridge against the bottom of a storage top disc.

The cartridge keeper preferably comprises at least two internal guide tracks for guiding the bottom stop in the same direction as the plunger is moving. By having these tracks the movement of the bottom-stop becomes much more stable. Hence, errors during loading/unloading etc are avoided.

Moreover the housing preferably comprises at least one hole in one of the walls for receiving an engagement protrusion integrated in the bottom-stop. By having this engagement protrusion the movement of the bottom stop is controlled within certain limits. It also prevents the bottom stop to fall loose when the housing is not loaded with a cartridge.

Hence the bottom-stop can move between two positions defined by the hole in the wall or by the hole in the wall and the bottom of the storage keeper.

Preferably the bottom-stop is forced towards the top position by a spring so that when the cartridge keeper is not loaded the bottom-stop is in an upper position and when it is loaded the bottom-stop is in a lowered position.

The cartridge keeper comprises a housing, which is preferably made of two halves.

Preferably the top of the two halves are inclined away from each other in order to facilitate the loading of a cartridge.

Furthermore the two halves are mounted by screw means in order to facilitate maintenance of the cartridge keepers and the devices mounted inside the keepers.

Moreover the internal spring device for the plunger is mounted in the bottom of the housing, so as to provide the longest possible way for the plunger to move.

The internal spring device preferably comprises:
at least one rod having a first and a second end,
at least one spring, and
at least one stop mean for preventing the spring to fall of the rod,
wherein the spring is mounted lengthways on the rod.

Furthermore the rod may have at least one stop-device in the second end.

Preferably the first end of the rod is mounted in the vicinity of the bottom of the cartridge keeper. In the internal spring device the rods are preferably the devices mounted in the bottom of the housing as described above.

The internal spring device preferably comprises a plunger device movable mounted on the rod between the spring and the stop means.

In an embodiment the plunger are preferably movable mounted to two rods between the spring and the stop means as described above.

The second end of the at least one rod may further comprises two incisions for receiving locking means. These locking means may be bricks that locks the rod to the bottom of the cartridge keeper. The bricks are preferably attached on opposite sides of the bottom.

Stickmover

The slide described above may preferably comprises teeth's for propulsion of the slide. Hence the teeth's interacts with a gearwheel mounted on a motor.

The pawl for pushing sticks is preferably flexible or hinged and spring loaded, so that it can follow a guide ramp on a cartridge. Hence the pawl is preferably resilient suspended to the slide so that it can follow a guide ramp on a cartridge.

The stickmover may preferably comprise a hatch for closing and opening a guide tunnel wherein the hatch is mechanically connected to the closing and opening device. The hatch prevents air etc to travel from the storage to the incubator or vice versa. Thus a more stable incubator and storage environment is achieved.

The closing and opening device described above comprises a protrusion for interacting with the slide, so that when the slides moves it pushes the protrusion which is mechanically connected to the hatch, so that the hatch opens.

The pawl preferably comprises an incision for receiving slides. Thus the part that interacts with the slides is preferably designed so that it fits with the design of the slides. Hence it provides a more secure catch, movement and release of the slides.

The tracks in the coulisse preferably comprise a flexible track changer for steering of the pawl lifter. When the stickmover moves a stick towards the incubator the pawl lifter preferably passes under the flexible track changer, on the return path the pawl lifter preferably passes on the upper side of the track changer and is thus steered to a different track.

The guide tunnel or stickmover tunnel, in which the sticks are transported on their way from the storage to the incubator may preferably comprise at least one sensor for monitoring if the pawl moves a stick or not.

Reload Hatch

The reload hatch described above may preferably comprise sensor means for securing that the hatch has been securely closed. If the hatch is not securely closed the stored sticks may be destroyed, hence the result from the analysis may come out wrong.

Furthermore the hatch preferably comprise a lock arrangement for guiding the hatch the last distance to a closed position. This is done automatically, the user only closes the hatch to an almost closed position wherein the mechanics inside the apparatus is able to interact with the hatch and close it to a closed position.

Therefore the lock arrangement preferably comprises a motor and a locking pawl for closing the hatch. Preferably the locking pawl engages with the hatch when the hatch is nearly closed by a user.

The locking pawl is preferably moved to close the hatch, by a motor with a gearwheel that engages with a teeth rack.

Furthermore the reload hatch preferably comprise guiding means for guiding a storage keeper. Hence when the hatch is opened, guiding means guides the storage keeper down to a load or unload position depending on if the storage keeper contains a cartridge or not. Preferably the load and unload position is the same.

Moreover the reload hatch preferably comprising a release arm for actuating a keeper spring mounted to the keeper, which holds the keeper in position in the storage carousel.

Even further the reload hatch may preferably comprise a depressor arm for pushing the cartridge down into the keeper. Hence during the loading process the cartridge is pressed down in the keeper. When the keeper is in position in the storage the depressor arm may release its pressure and the cartridge preferably moves to a storage position wherein the protrusion on the cartridge preferably interacts with the bottom side of the upper disc in the storage.

Carry-over Control Koncept

The carry-over control method described above may furthermore comprise the steps of:

Moving the dosage needle to a cavity where a second liquid is added by a second needle, the second liquid immersing and thus cleaning the needles on the outside.

Moving the needles slowly away from the cavity, in order to draw the second liquid off the outside of the needles.

Stick Waste

The waste storage device described above may preferably comprise at least two sensors, a first sensor for detecting that the container is in place, a second sensor for detecting if the hatch cover is in closed position. If these are not correct it may have impact of the internal environment of the analysis apparatus. Hence the result of the analysis may come out erroneous.

Furthermore the waste storage device may comprising a third sensor for detecting if the hatch cover is in open position. By having this sensor the internal computer system controlling the apparatus is able to control when it is safe to transfer a stick from the incubator into the waste storage.

Moreover the waste storage device preferably comprises a sensor for monitoring the number of sticks that are transferred. Hence an alarm may be activated when the waste storage is close to full.

The monitoring is preferably done by counting the number of sticks transferred between the incubator and a storage. The storage is preferably the waste storage, however the number of sticks may also be measured between the stick storage and incubator.

The hatch cover is preferably connected to the motor by a spring or other flexible element. This is more safe since if the opening is obstructed by a stick the hatch is able to flex and thus mechanical or electrical damage may be avoided.

The method for managing a waste storage device comprising a container for receiving used sticks, a hatch cover, a motor for closing and opening the hatch cover, and at least one sensor for sensing that the hatch cover is in closed position, the method preferably comprises the following steps:

checking if the sensor sends a signal that the hatch cover has returned to closed position after the hatch cover has been opened, and if no signal is sent by the sensor an alarm is triggered.

These and other aspects of the invention will be apparent from and elucidated with reference to the embodiments described hereinafter.

BRIEF DESCRIPTION OF FIGURES

The patent or application file contains at least one drawing executed in color. Copies of this patent or patent application publication with color drawing(s) will be provided by the Office upon request and payment of the necessary fee.

FIG. 11 shows an exploded view of the analysis apparatus from the front.

FIG. 12 shows an exploded view of the analysis apparatus from the back.

FIG. 13 shows a view of an analysis apparatus from above

FIG. 14 shows an exploded front view also showing the cooling arrangement in a second embodiment.

FIG. 15 shows a back view of a second embodiment of an analysis apparatus.

FIG. 32 shows details located on the upper disc in the storage carrousel, for mounting of cartridges in the storage carrousel.

FIG. 33 shows two types of cartridges mounted in a storage carrousel.

FIG. 34 shows another embodiment of storage carrousel also comprising two types of cartridges.

FIG. 35 shows details located on the upper disc in the storage carrousel, for mounting of cartridges.

FIG. 36 shows one type of cartridge mounted in a storage carrousel wherein the protrusion for positioning of the cartridge is shown.

FIG. 37 shows an enlargement of the protrusion and its function in previous figure.

FIG. 43 shows a first embodiment of guiding slots.

FIG. 44 shows a second embodiment of guiding slots.

FIG. 45 shows a second embodiment of guiding slots.

FIG. 74a shows a scenario of applying fluid to a stick.

FIG. 74b shows an embodiment of applying milk onto a test stick.

FIG. 75 shows a valve and pump arrangement.

FIG. 107 shows the object field, view field and peak line (reaction line).

FIG. 108 shows a second embodiment of an optical reading housing comprising inner screening walls, a lens, lens tube, illumination sources, reflectors, image sensor and membrane.

FIG. 109 shows a side view of the housing shown in FIG. 108.

FIG. 119 shows the consumables room mounted to the beam.

FIG. 120 shows an exploded view of the mounting of the consumables room and the stickwaste system to the beam.

DETAILED DESCRIPTION OF PREFERRED EMBODIMENTS

In the following an embodiment of the present invention will be disclosed with reference to the accompanying drawings.

Functional diagram of the Analysis Instrument (AI).

Figure 1:
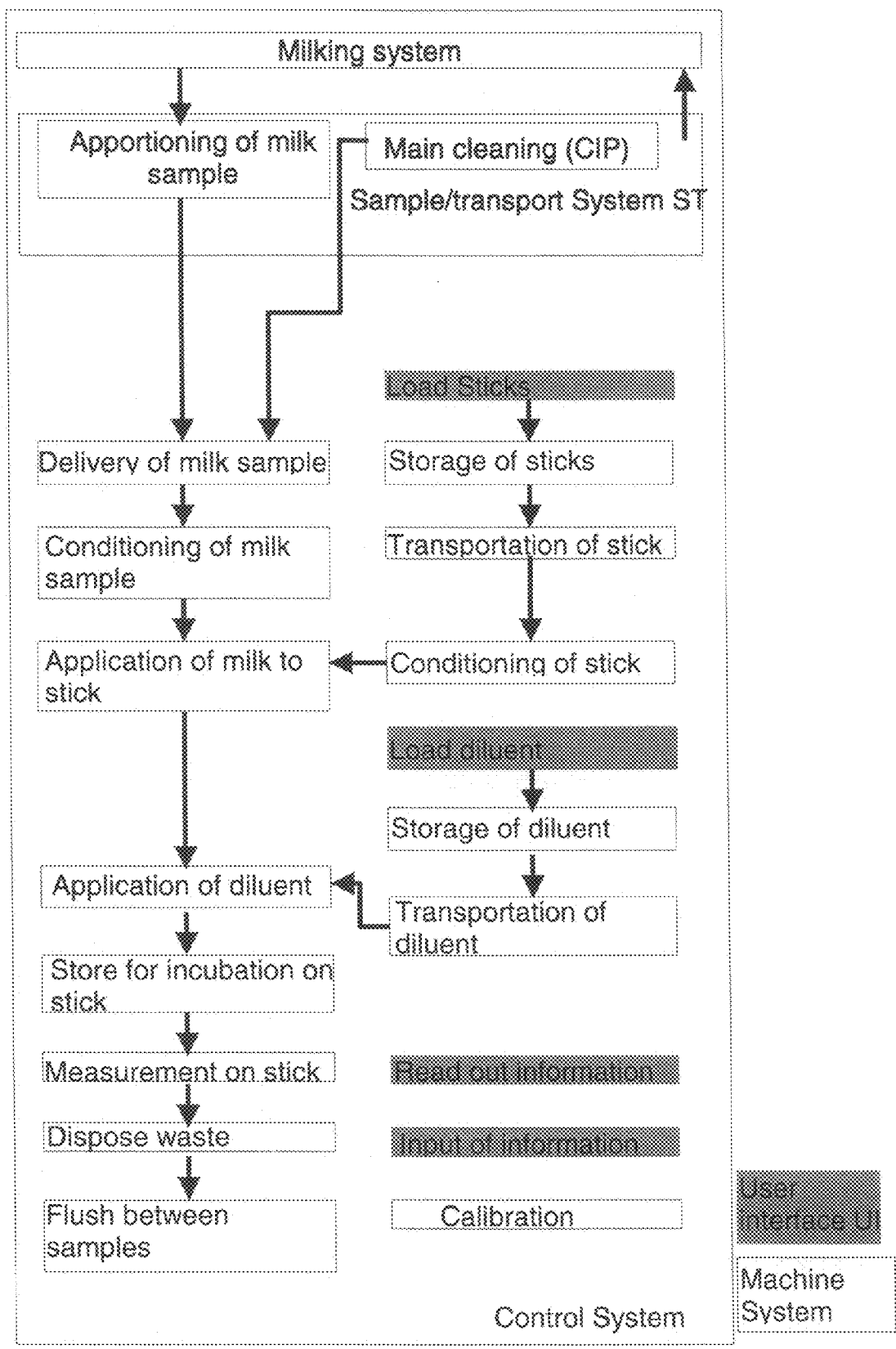
FIG. 1 shows a simplified functional diagram of the analysis apparatus.

A functional diagram of the analyser is shown in FIG. 1. The main functions are described by:

A milk sample is apportioned from the sample/transport system (ST) not shown, and delivered to the analyser. The sample is transported and applied to the sticks. For one stick type a diluent is applied to the stick preferably in the same sequence as the sample is applied. The sticks with the applied sample are incubated while the chemical reaction takes place, and the result is measured. Finally the stick with the sample is transferred to the stick waste container.

To realise these main functions some additional functions are preferably needed:

Magazines of sticks are loaded to a stick storage by the operator, sticks are transported to dosage. Flushing of the flow system with milk is preferably performed between each sample. It is possible to flush with other liquids, e.g. water, between samples (CIP between samples). Main cleaning (CIP) is performed between milking sessions. Diluent is loaded by the operator, stored, transported and added to the sample. Information is read out on a display and information can be entered by the operator into the system by using the user interface (UI) shown in FIG. 1.

Figure 2:
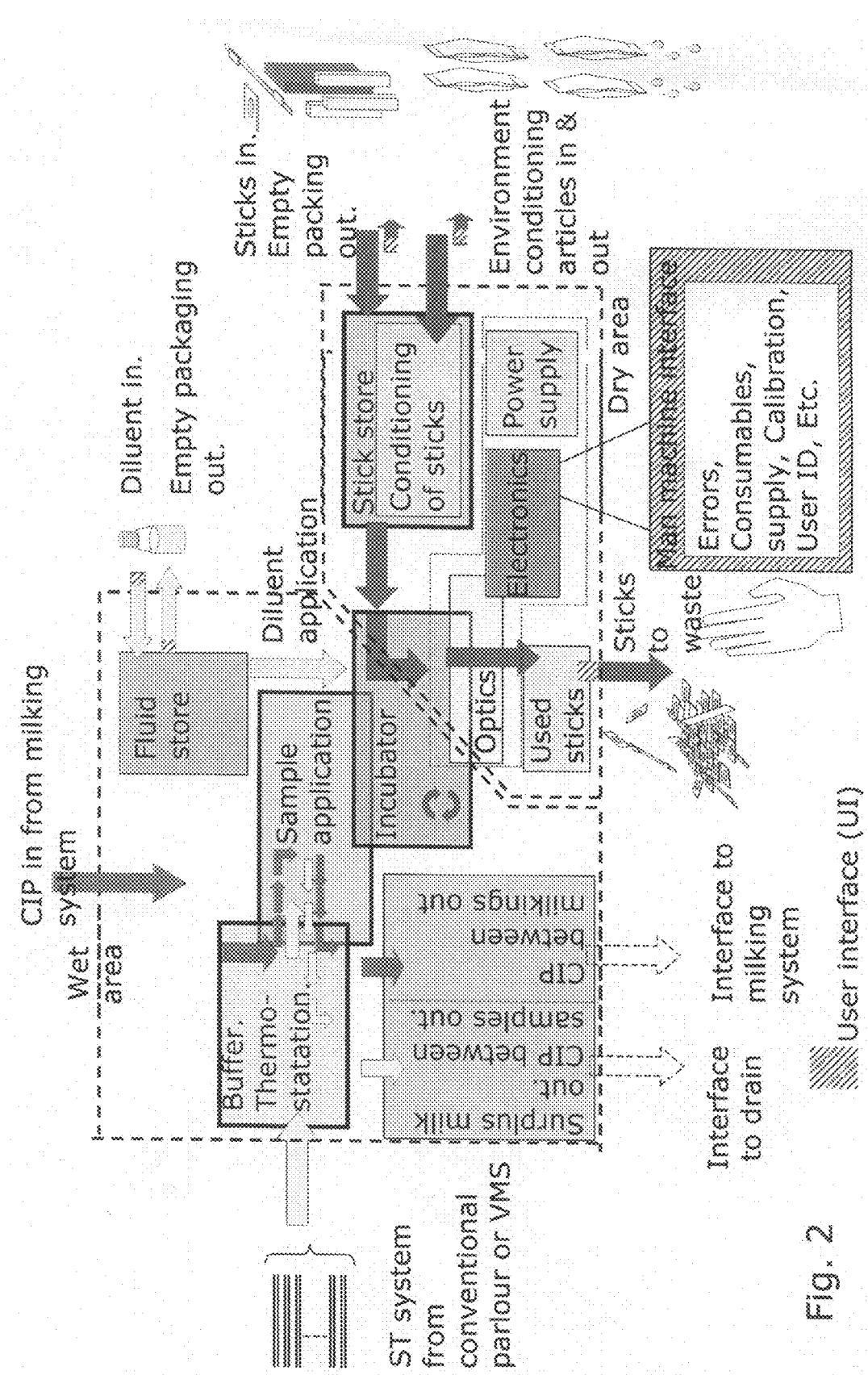
FIG. 2 shows an embodiment of a flow diagram of the analysis apparatus.
Figure 3:
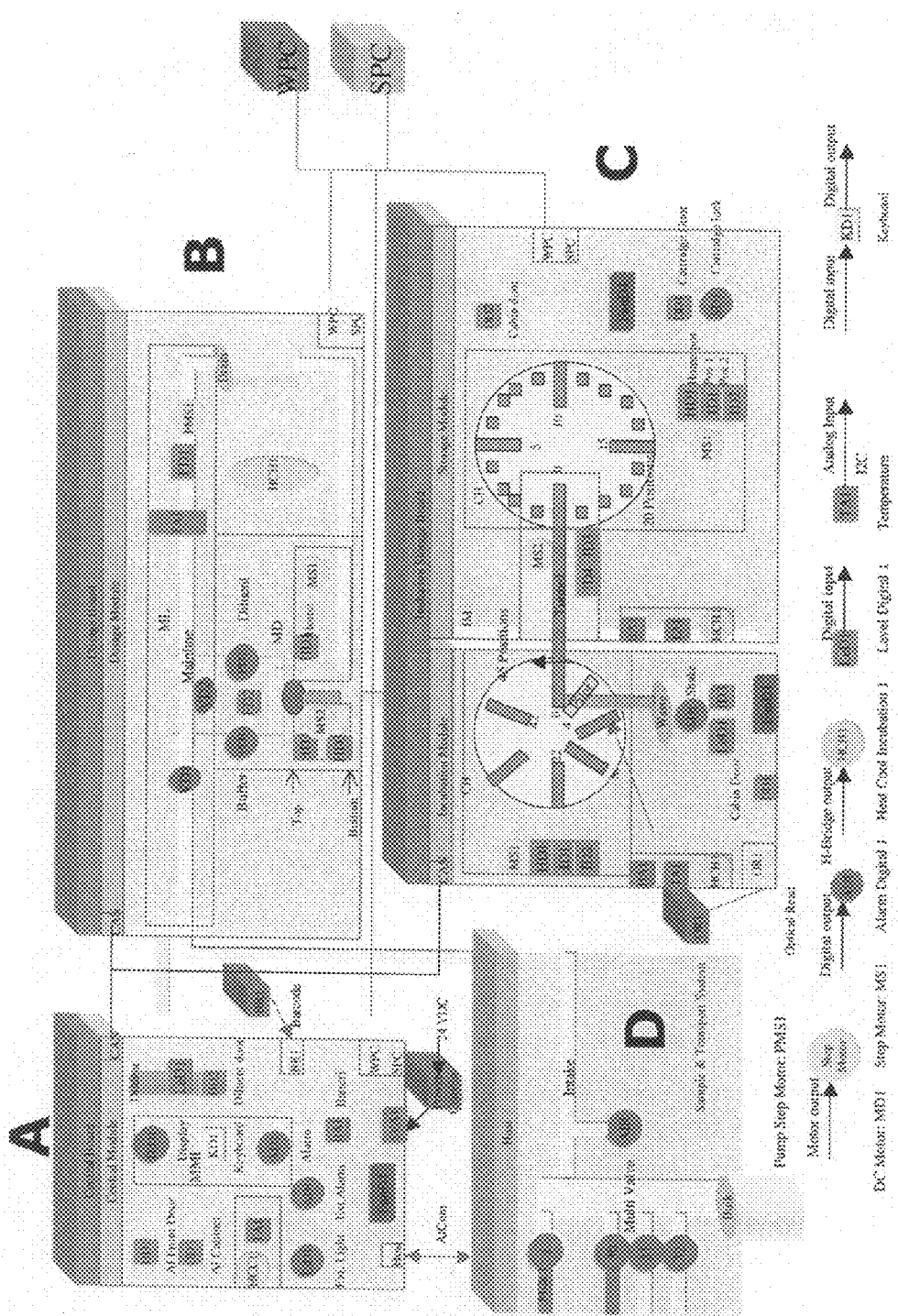
FIG. 3 shows a configuration diagram of the analysis apparatus.
Figure 3A:
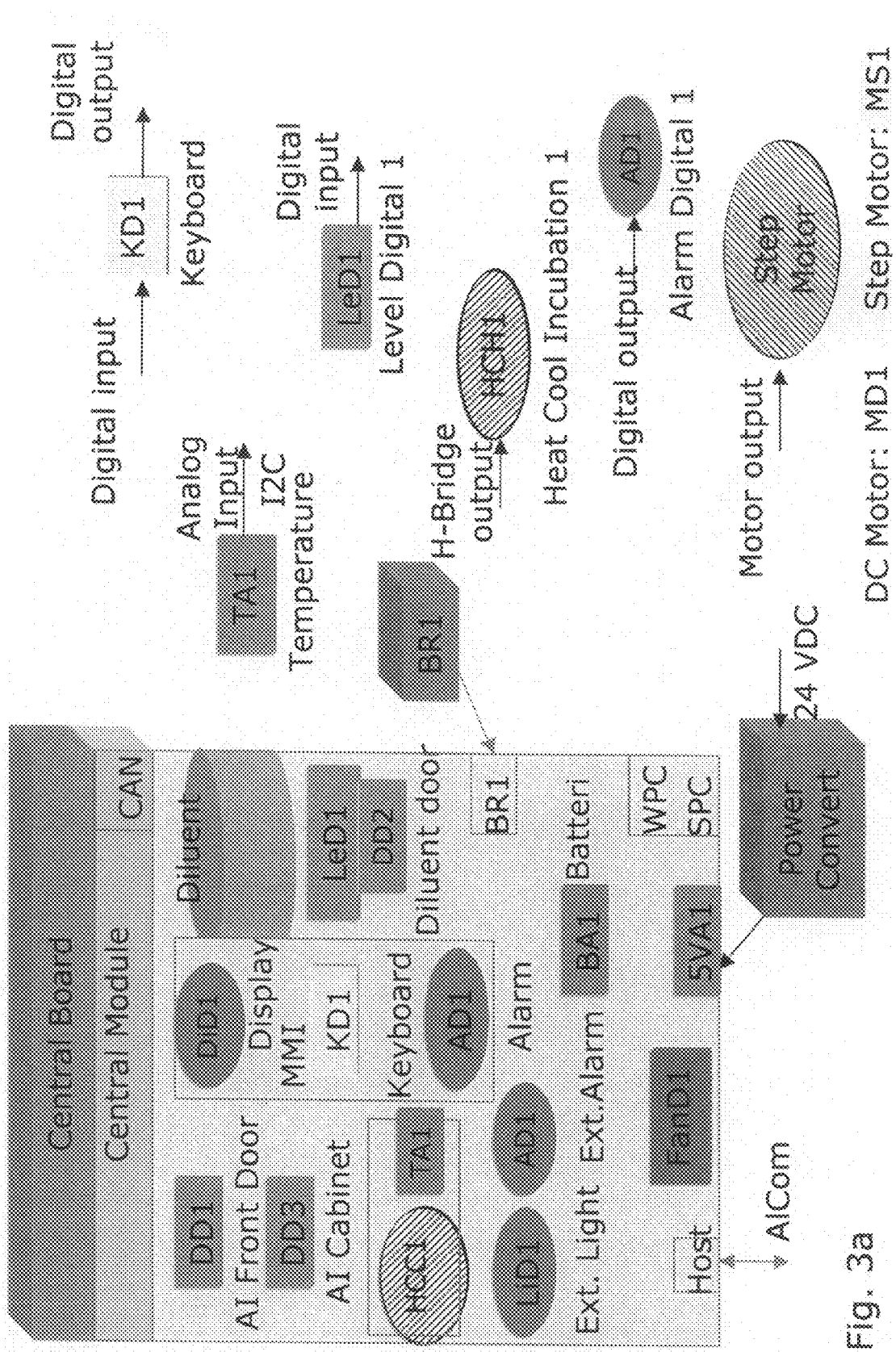
FIG. 3a shows a configuration diagram of the central module.
Figure 3B:
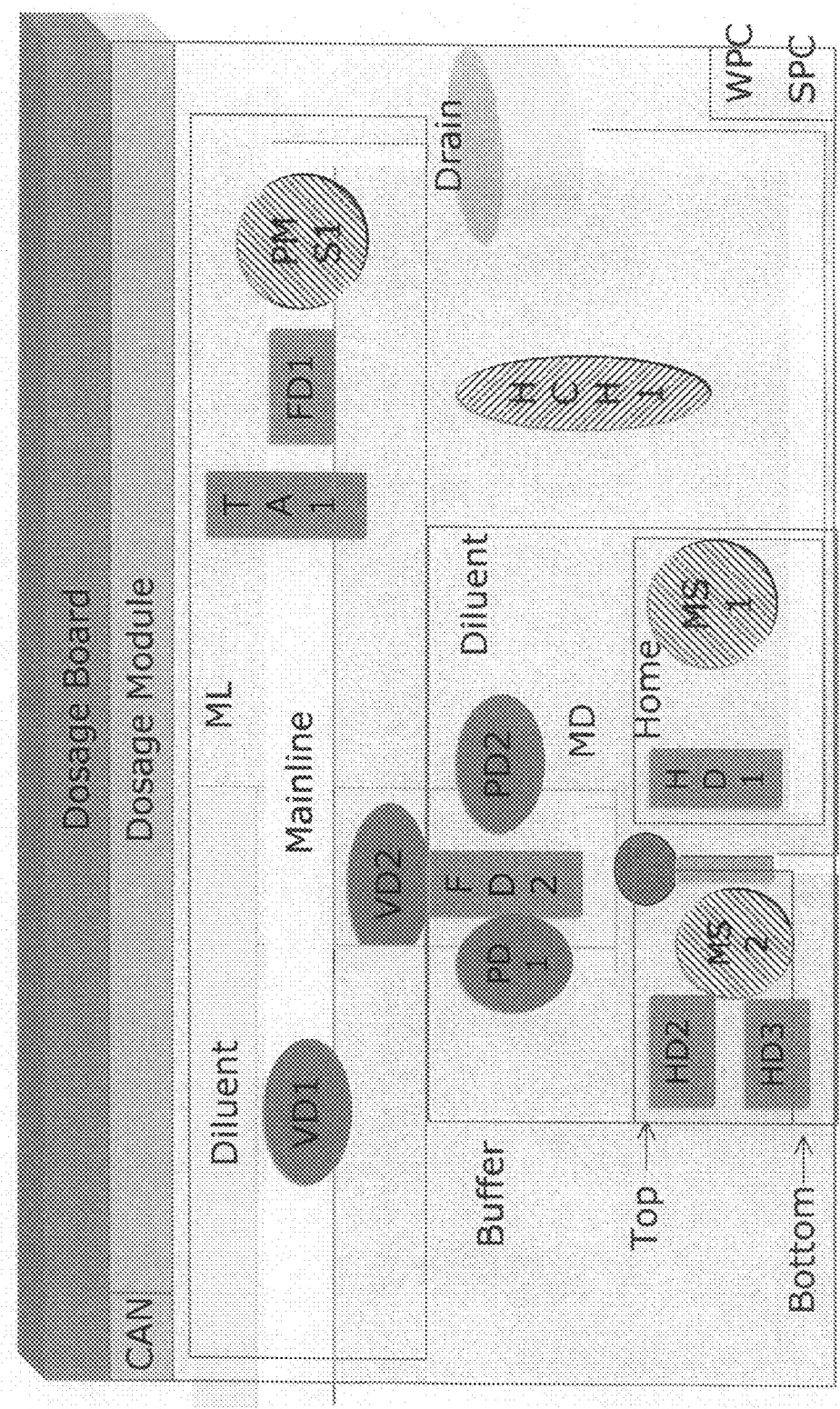
FIG. 3b shows a configuration diagram of the dosage module.
Figure 3C:
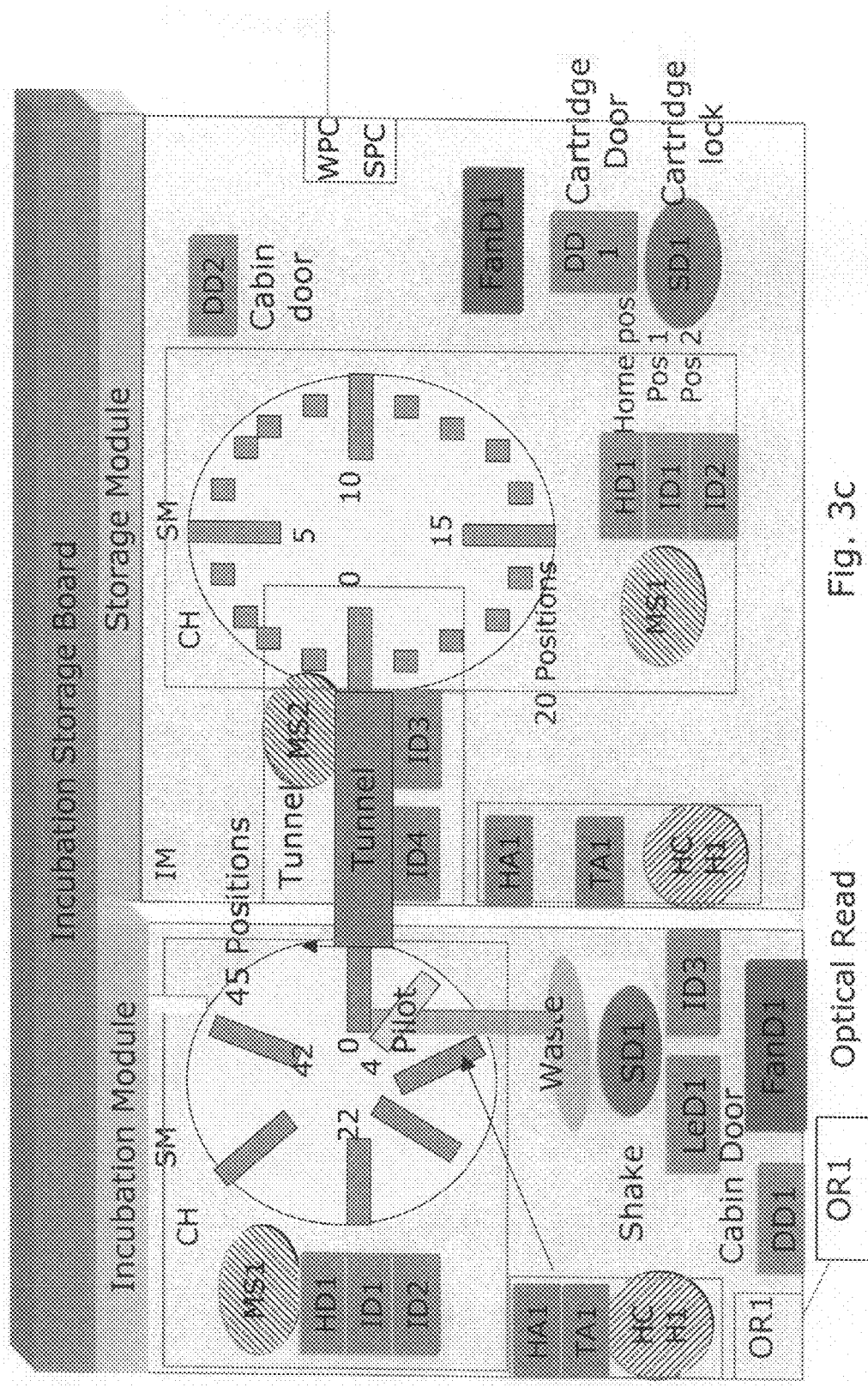
FIG. 3c shows a configuration diagram of the incubator and storage module.
Figure 3D:
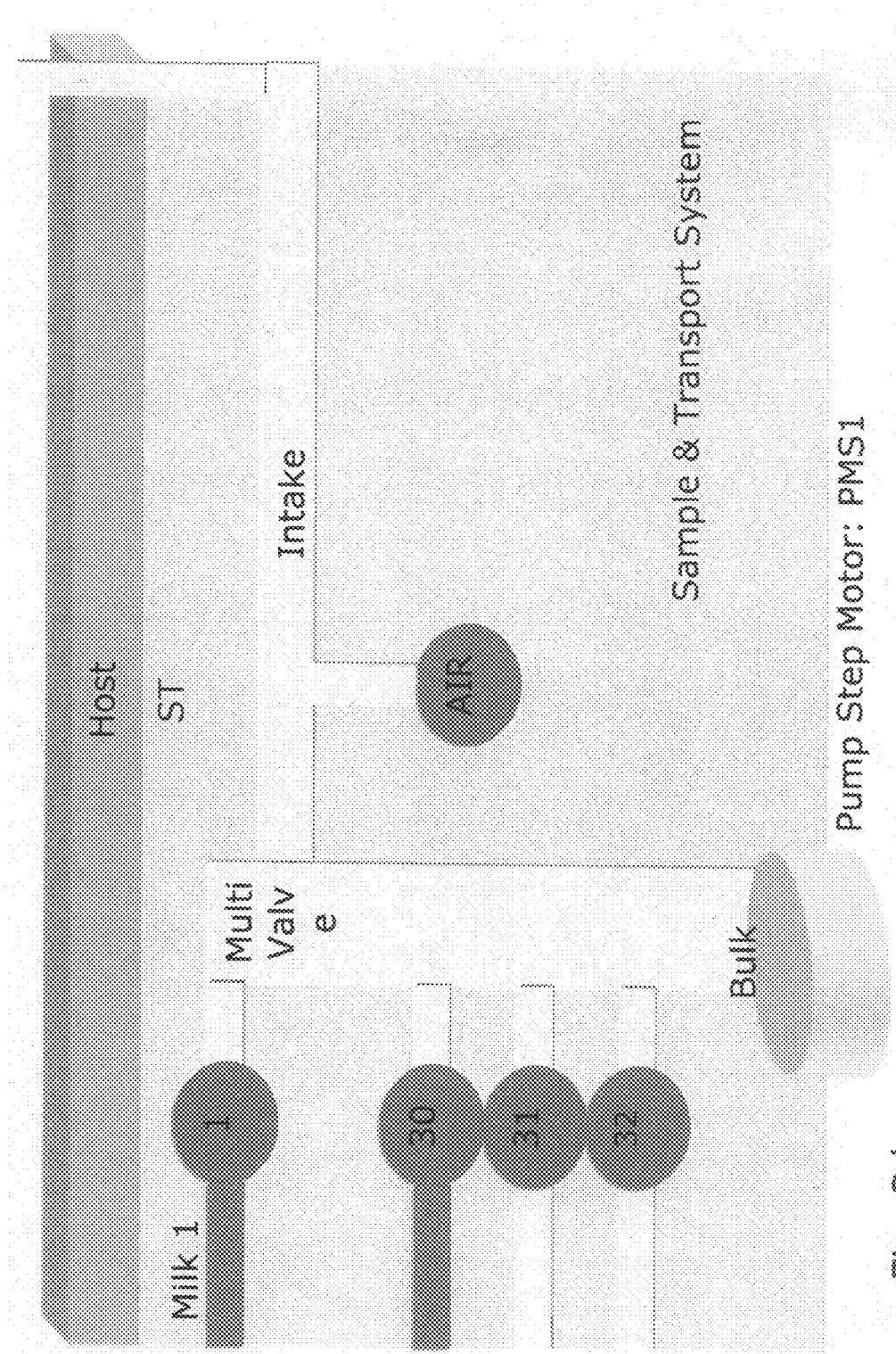
FIG. 3d shows a configuration diagram of the host module.
Figure 4:
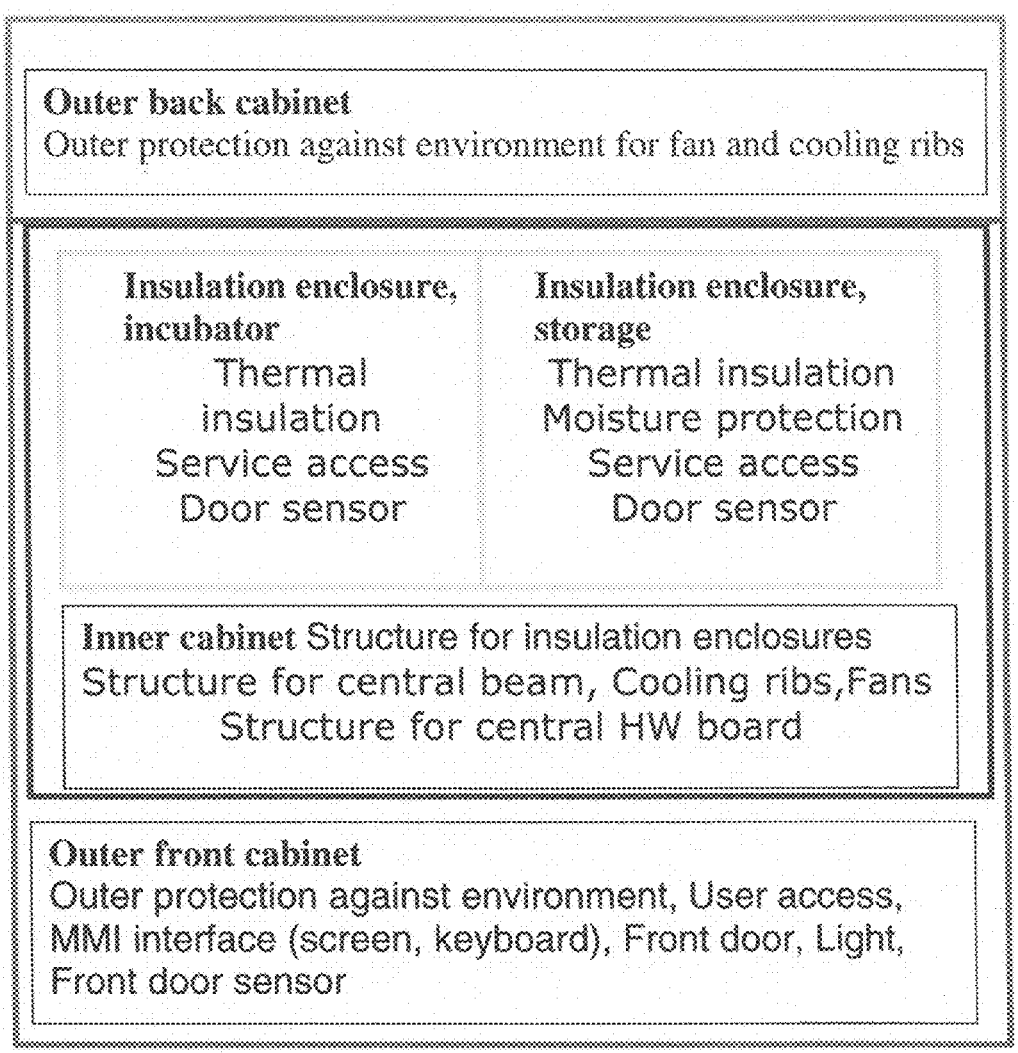
FIG. 4 shows a schematic view of the analysis apparatus.

In FIG. 2, a flow diagram of the system in which the analysis instrument is a part, is illustrated. A wet and a dry zone are shown, and an indication of the functional modules is illustrated. The functional modules in FIG. 2 comprises:

Man machine interface (MMI)
Stick storage with conditioning of sticks (temperature, humidity)
Incubator
Sample application
Optics
Storage for used sticks
Electronics
Power supply
Storage for fluids The configuration diagram in FIG. 3 illustrates the elements, which are subjected to functional entities for controlling the instruments.

The diagram is divided into four main components.
Host component: External component
Central component
Dosage component
Incubation and Storage Component Description of the Host Component (External Component) in FIG. 3.

The Host element represents the Sample Transport system, which shows up to 32 milking point pipelines connected to a multi valve. The milk sample will be transferred through the intake into the mainline in the AI. The communication between the Host and the AI can be done by a ALCOM bit protocol via an HSPI interface attached on the Central board.

Description of the Central Component in FIG. 3.

The central component comprises a central board which comprises a central module further comprising means for alarm function, means for light function, man machine interface, computing means, control means.

Description of the Dosage Component in FIG. 3.

The dosage component comprises a dosage board which comprises a dosage module further comprising pipes, a drain and diluent.

Description of the Incubation and Storage Component in FIG. 3.

The incubation and storage component comprises an Incubation Storage board further comprising an Incubation Module and a Storage module.

The overall physical realisation of an embodiment is shown in FIGS. 5-17, which illustrates an exploded view of the cabinet with the internal mechanical structure and devices as well as the outer design. The mechanical functions are realised in modules that can be assembled and exchanged with a minimum of adjustments. Most of these modules are mounted to a central beam 46, that gives precise tolerances between the modules.

The Operators User Interface

Figure 9:
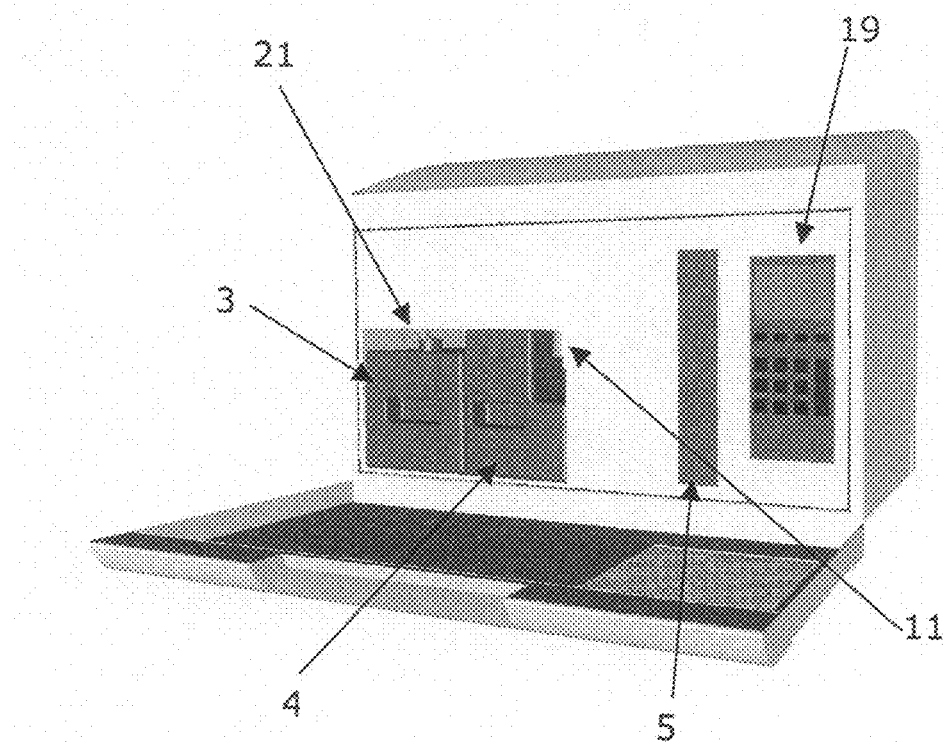
FIG. 9 shows the front of a second embodiment of the analysis apparatus.
Figure 10:
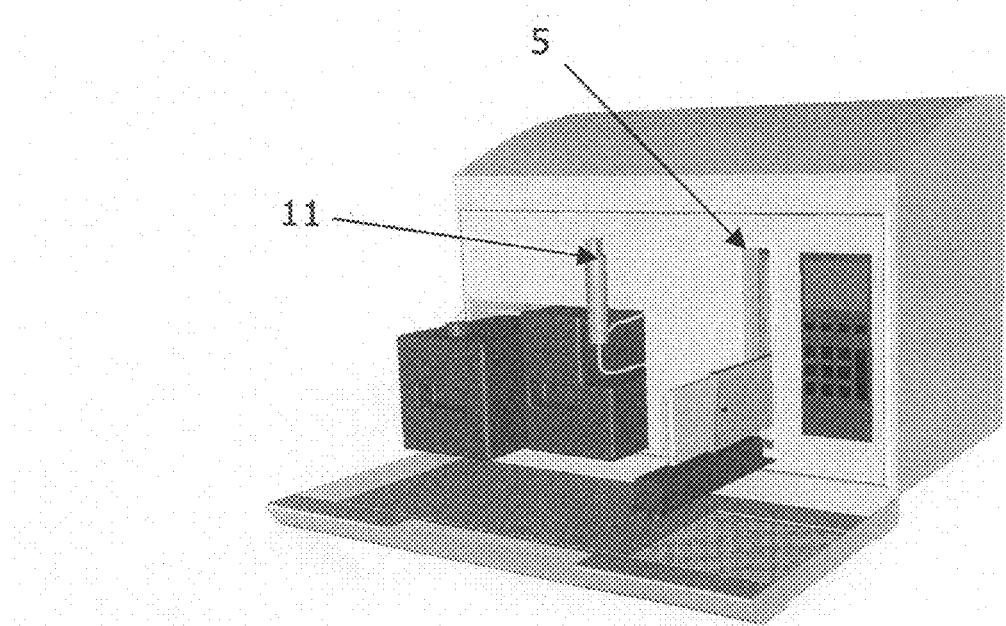
FIG. 10 shows the user interface of a second embodiment of the analysis apparatus.
Figure 16:
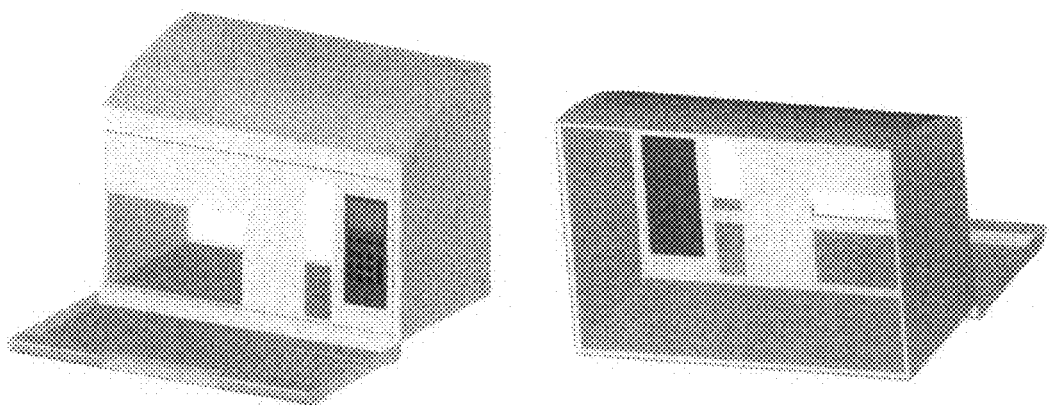
FIG. 16 shows an embodiment of an outer front cabinet.

The operator user interface 19 is shown in FIG. 9 which also shows the front of the AI with the front door open 20 and the exchangeable parts assembled in their positions. FIG. 10 shows the same view but with the exchangeable parts partly removed from their assembled position.

A First Embodiment of the Cabinet.

In a first embodiment, shown in FIGS. 21-28, the cabinet can be defined as:

The outer protection against the environment 32.

The structure for mounting a central beam 46 on which most of the modules are mounted. The structure for the central beam is preferably housed by the main cabinet 32.

Structure for mounting elements not mounted on the central beam. The structure for insulation enclosures: top insulation part 10, bottom insulation part 29, and the structure for central HW board can be housed by the main cabinet as well.

Environmental Protection

A central problem in the cabinet design is to prevent humidity and dust from entering the cabinet. This has been solved by closing the outer cabinet and the insulation enclosures as effectively as possible, creating a double enclosure.

In order to protect the internal parts, preferably a structure having a main cabinet as structure for insulation enclosures and the mechanical modules and the hardware (HW) is used. The internal devices and structures are protected towards the outer environment, by an outer top cover and insulation enclosures, creating a double sealing towards the environment. The only openings into the cabinet are preferably the inlet for cartridges, where a reload hatch can be opened, and the consumables room where diluent can be loaded and the stickwaste container removed. These two openings are carefully designed in order to avoid air penetration when closed.

User Interface

A front door 31 in the outer cabinet gives the user access to the user interface 19, preferably comprising a keyboard, screen/display, cartridge load 5, stickwaste container 4, diluent container 3, liquid waste funnel 11, filter for milk sample 21 etc.

In the following a first embodiment of the cabinet shown in FIGS. 21-28 is described.

Figure 28:
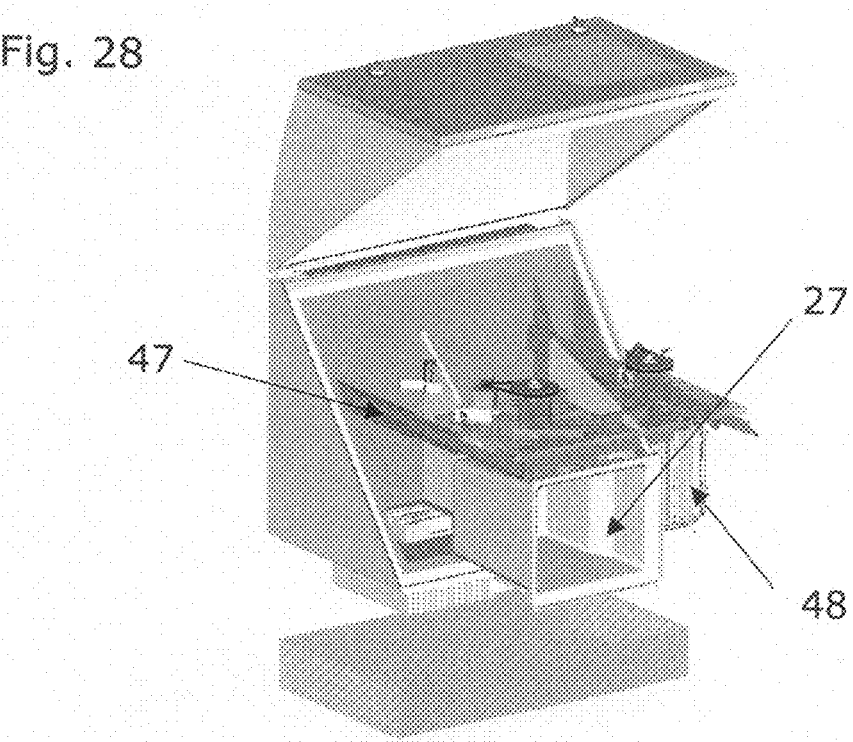
FIG. 28 shows a view wherein the top cabinet is open displaying the interior in service position.

To improve the serviceability, a beam mounting concept has been designed where the beam is mounted on two linear drawer slides 47 that allow the beam to be drawn out to a service position shown in FIG. 28.

In FIG. 28 the consumers room 27 and the storage carrousel is shown.

Figure 24:
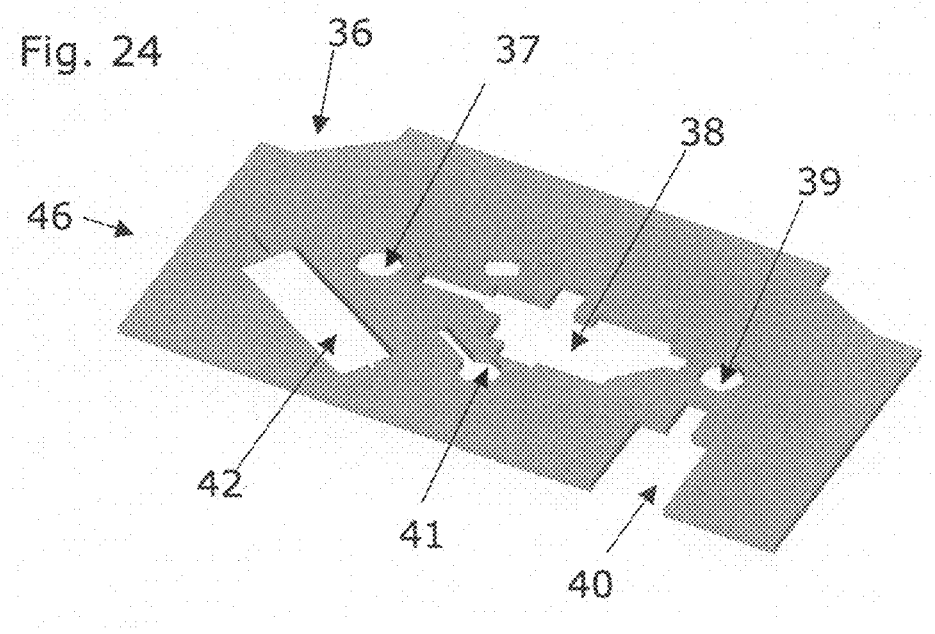
FIG. 24 shows an first embodiment of an internal central beam.

The main parts of the external cabinet is a front door 31, a top cover 30, a main cabinet 32, a cooling fin enclosure 34, a window 33, and a mounting frame, see FIG. 24. All the external parts are preferably made of stainless steel.

Figure 29:
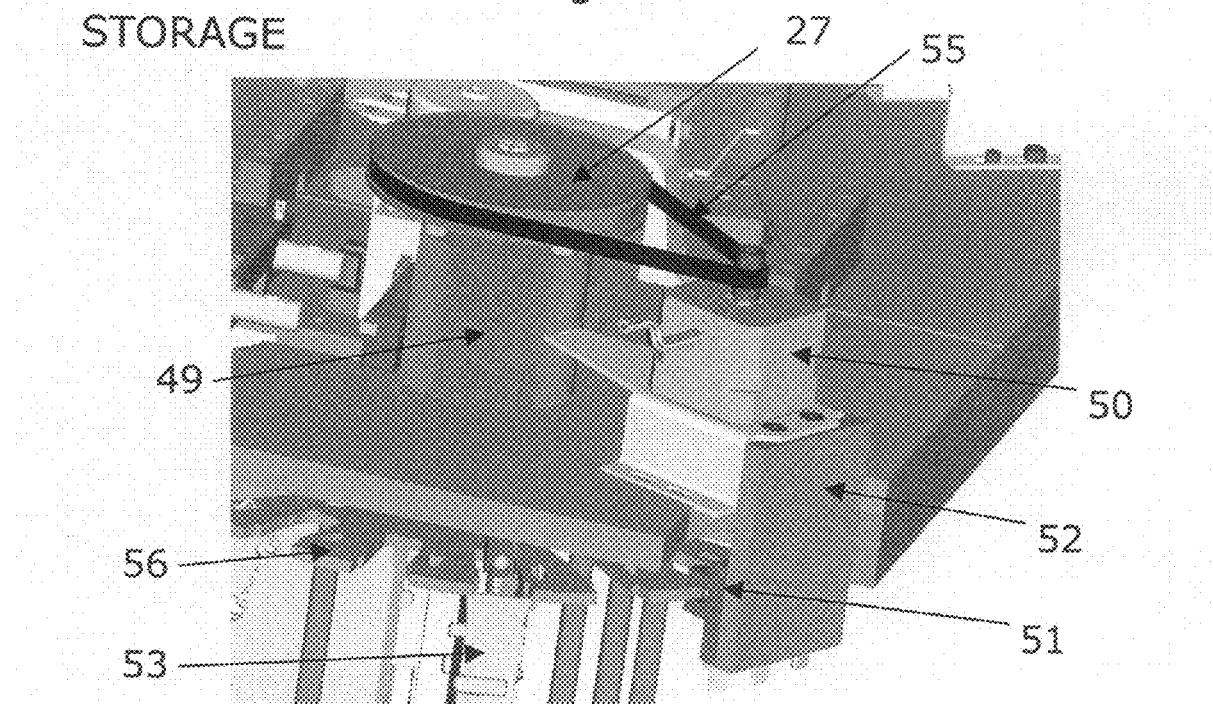
FIG. 29 shows the driving assembly for rotation of the storage carrousel.

The mounting frame or beam shown in FIG. 24 preferably comprises a cut out for mounting of a driver module comprising sensors shown in FIG. 29, a cut out for mounting of a bearing house for both the incubator and storage 37, 39, a cut out for mounting of a stickmover module, a cut out for a dosing needle 41 wherein the cut out preferably comprises a circular area and a slit, wherein the circular area is where the waste funnel, drain preferably is located and the slit is where the dosing needle moves to different positions for dosing a sample on to a test stick.

Furthermore the mounting frame preferably comprises a cut out for a hatch.

Figure 96:
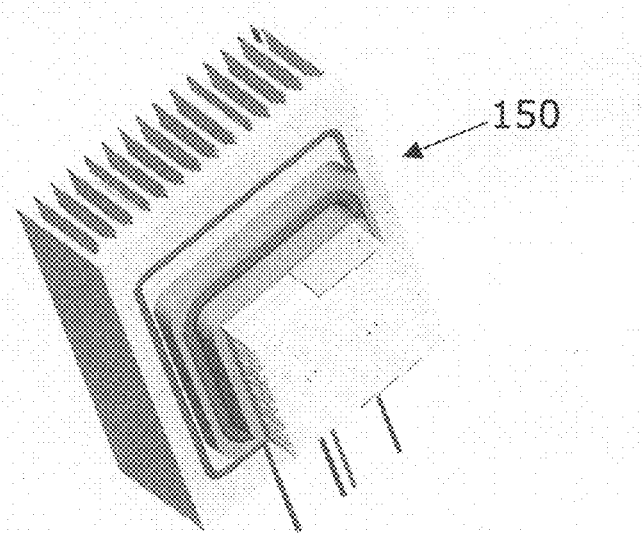
FIG. 96 shows cooling element of an analysis apparatus.
Figure 97:
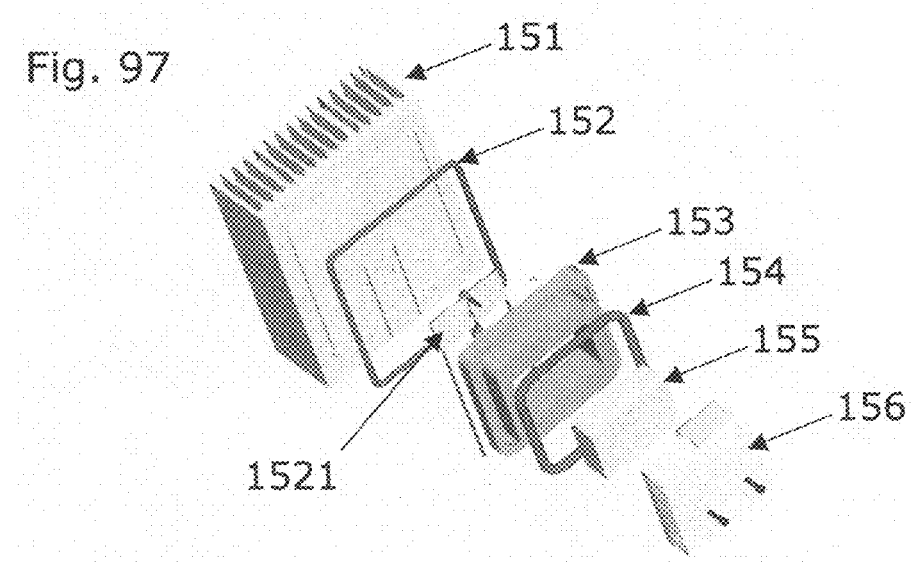
FIG. 97 shows an exploded view of the cooling element in FIG. 96.

The internal parts of the cabinet is the insulation enclosure that consist of the bottom insulation part 29, the top insulation part 10, the consumables room 27, the cooling modules 22, also shown in FIGS. 96 and 97, and the beam mounting system 47.

Figure 21:
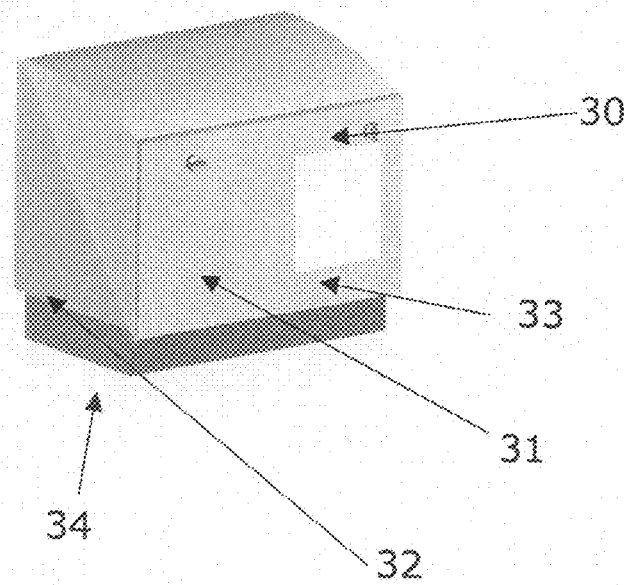
FIG. 21 shows a front view of a first embodiment of the analysis apparatus.

Front Door:

The front door 31, FIG. 21, gives access for the user to refill stick storage, refill diluents and empty the waste container. The front door is attached with hinges to the front cover. There are preferably two hinges in the bottom of the door, and preferably two locks at the top of the door.

The front door is sealed between the top cover with an extruded silicone gasket 35 (preferably Elsteel type). The front door preferably has a window 33 that allows the user to see the display, when the door is closed.

Figure 22:
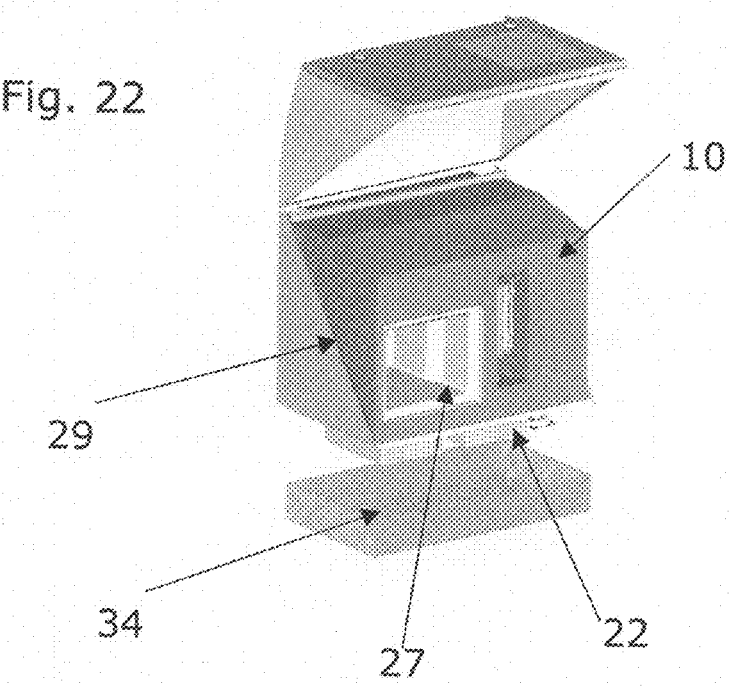
FIG. 22 shows an exploded view of a first embodiment of the analysis apparatus.
Figure 23:
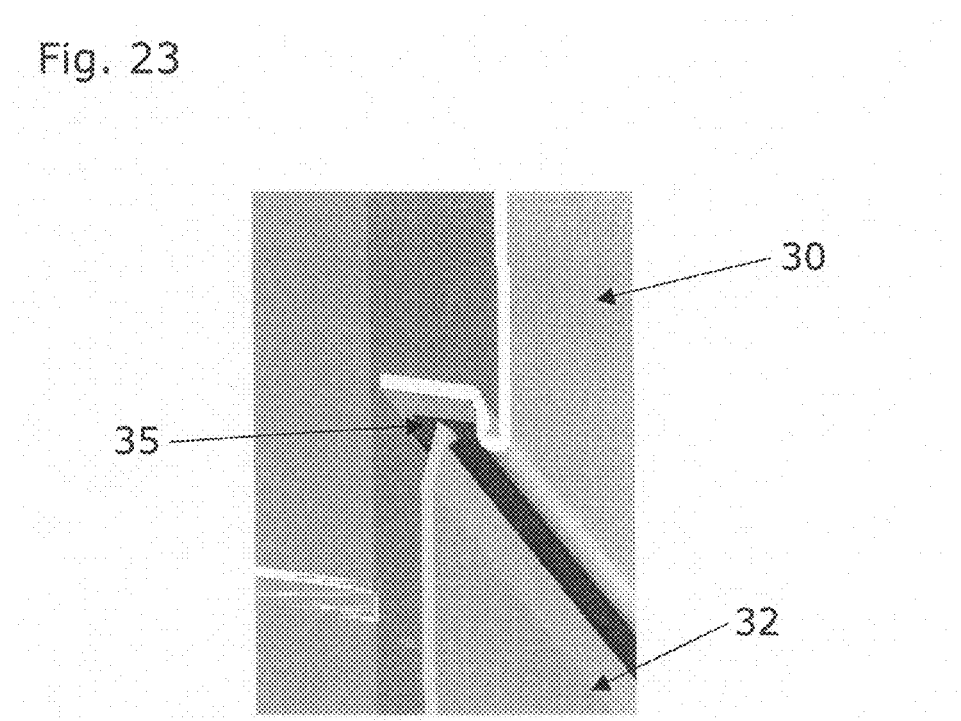
FIG. 23 shows details for sealing of the analysis apparatus.

Top Cover:

The top cover, FIG. 22, is hinged in the back/top of the main cabinet, with two adjustable hinges. The flange which seals to the main cabinet has an extruded silicone gasket (Elsteel type). The profile of the flange ensures a simple protection of the gasket, FIG. 23. The closed top cover is locked with a line of screws at the front/lower edge. The hinges can be adjusted in a way that when the locking screws are tightened the gasket will have an even pressure over the entire gasket surface.

When the top cover is opened, it will be held in open position with either a gas damper or a simple rod like on an automobile hood. Opening of the top cover gives access to remove the top insulation part.

Main Cabinet:

The main cabinet holds the insulation enclosure, see FIG. 22, the top cover and the cooling fin enclosure. The main cabinet and the top cover together form the primary sealing against the environment. The back of the main cabinet has brackets that mount on the mounting frame.

Cooling Fin Enclosure:

The cooling fin enclosure 34 prevents dust and water from entering the cooling fins 22 and protects the cooling fans and fins. The air intake for the fans is preferably provided with a filter mat that will keep the dust out. The filter mat can be replaced/cleaned.

The cooling fin enclosure is sealed against the main cabinet preferably with a rubber gasket, see FIGS. 22 and 97.

Mounting Frame:

The mounting frame is the interface between the AI and the wall/floor or wherever the AI has to be mounted. A standard range of mounting frames has to be considered.

The mounting frame is preferably equipped with vibration dampers.

Insulation Enclosure:

The insulation Enclosure consists of a top 10 and a bottom 29 insulation part. The material is preferably either Expanded polystyrene (EPS) or Polyurethane (PUR). To reduce the diffusion of humidity from the environment air, the insulation enclosures has to be either coated or provided with a lining of thermoformed plastic. The insulation enclosure preferably has three separate compartments that are sealed from each other.

Figure 25:
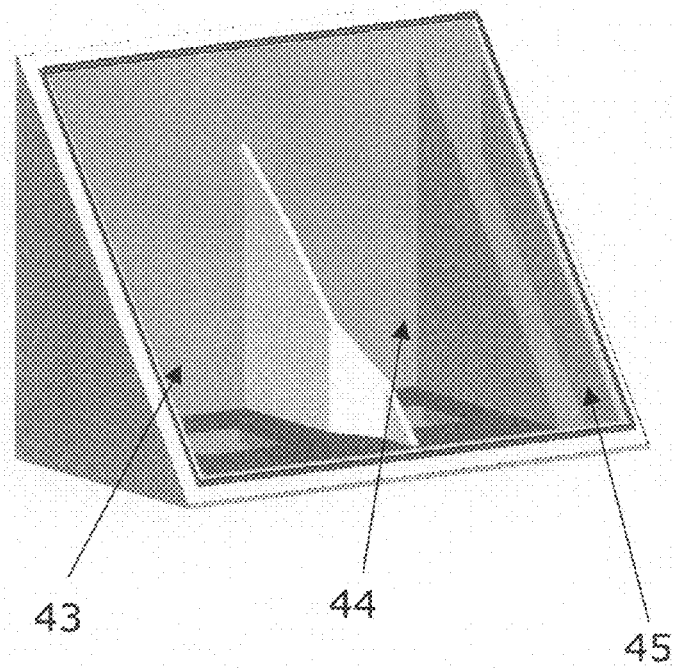
FIG. 25 shows a first embodiment of a back cabinet comprising the different compartments.
Figure 26:
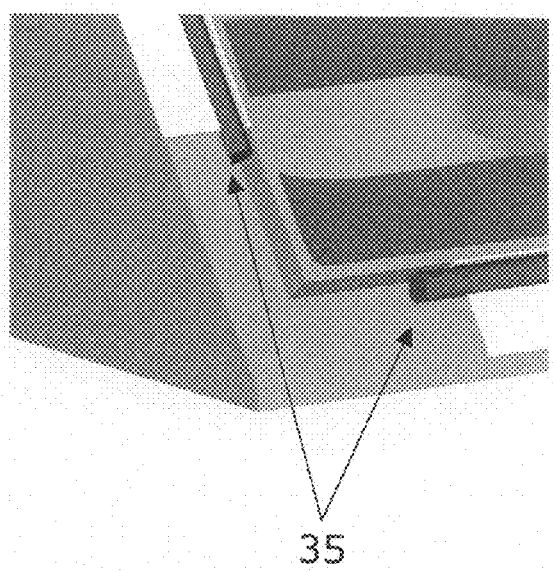
FIG. 26 shows details for sealing between the main cabinet and top cabinet.
Figure 27:
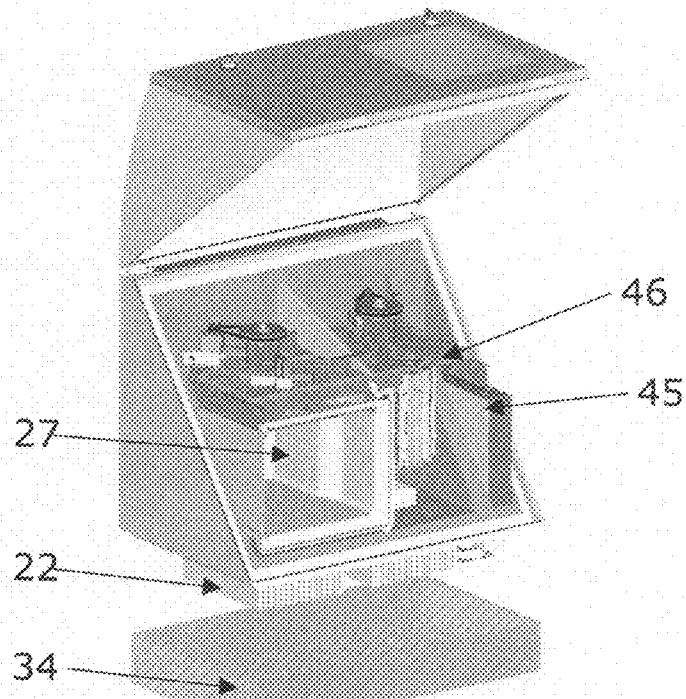
FIG. 27 shows a view wherein the top cabinet is open displaying the interior in assembled position.

The three compartments are the IM compartment 43 (Incubator Module), the SM (Storage Module) compartment 44, and the ICM (Integrated Control Module, containing all electronic boards) compartment 45, se FIG. 25.

The separation between the IM and SM compartment consist of a wall partly attached to the beam and to the top/bottom insulation parts. The top and bottom insulation parts are provided with an aluminium profile on the flange surfaces. The aluminium profile has a grove for the silicone gasket. The two aluminium profiles are tightened against each other with a number of screws to ensure the sealing of the 3 compartments.

To protect the PC boards in the ICM a dessicant or molecular sieve bag is preferably placed in the ICM compartment. This bag may be replaced at regular intervals.

Consumables Room:

The consumables room 27, see FIG. 28, is preferably made of thermoformed ABS. The consumables room is preferably attached to the bottom of the beam, and thus follow the beam when the beam is drawn to service position.

The openings in the consumable room 27 for the tubes and the sample waste funnel will be kept as sealed as possible, this is to reduce the air exchange when the consumables room is opened for daily operation.

Beam Mounting System:

The beam mounting system 47 consists off two linear slides that holds the beam in position, and allows the beam to be drawn forwards to the service position with improved service access, see FIG. 28. The beam mounting system is attached to the main cabinet with a bracket through the bottom insulation. When the beam is in the service position the storage carrousel is clear from the insulation bottom, and can be dismounted and removed downwards. A locking system will secure that the beam is kept in the right position when in home position.

Before the beam can be drawn out, the cables from the ICM preferably has to be dismounted and extension cables may be mounted to operate the beam in the service position.

Cooling Modules/Peltier Sandwich

The cooling modules 22, 150, see FIGS. 96 and 97, is preferably placed at the bottom of the cabinet. This allows the outside part of the cooling modules to be serviced from bottom of the AI when the cooling fin enclosure is removed. The fans for the external cooling fins have to be protected against the humidity in the stable environment. This could be either individual fans for each cooling fin, or a common fan with a distribution air pipe to the cooling fins.

A Second Embodiment of the Cabinet

In a second embodiment the cabinet, shown in FIGS. 5-17, may be defined as:

The outer protection against the environment.

The structure for mounting a central beam on which most of the modules are mounted. The structure for the central beam is housed by the inner cabinet.

Structure for mounting elements not mounted on the central beam. The structure for insulation enclosures and the structure for central HW board can be housed by the inner cabinet as well.

Overall description of the casing in the second embodiment.

FIG. 11 and FIG. 12 illustrates an exploded view of the overall description of the casing. In FIG. 11 the front door 20, the outer front cabinet 18, the inner cabinet 17 and the outer back cabinet 16 can be seen, as well as some of the insulation enclosure. FIG. 12 shows the same parts but from a different view angle, this time from behind with the outer back cabinet removed so that the cooling ribs on the inner cabinet backside can be seen.

Environmental Protection

In order to prevent humidity and dust from entering the cabinet and at the same time allowing airpassage when temperatures are changing. The cabinet is closed as effectively as possible and pressure release is done through a valve where humidity and dust can be controlled.

Figure 5:
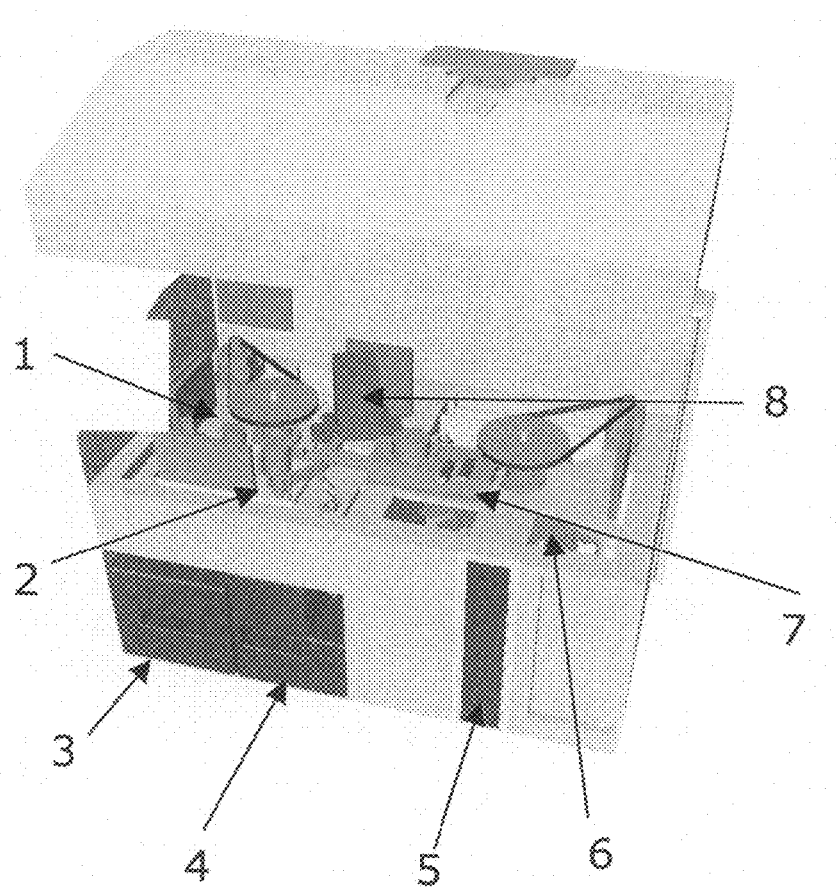
FIG. 5 shows an exploded view of a second embodiment of the analysis apparatus, comprising a wet system 1, an incubator 2, diluent 3, stick waste 4, stick load 5, storage 6, stick mover 7, optical reader 8.
Figure 7:
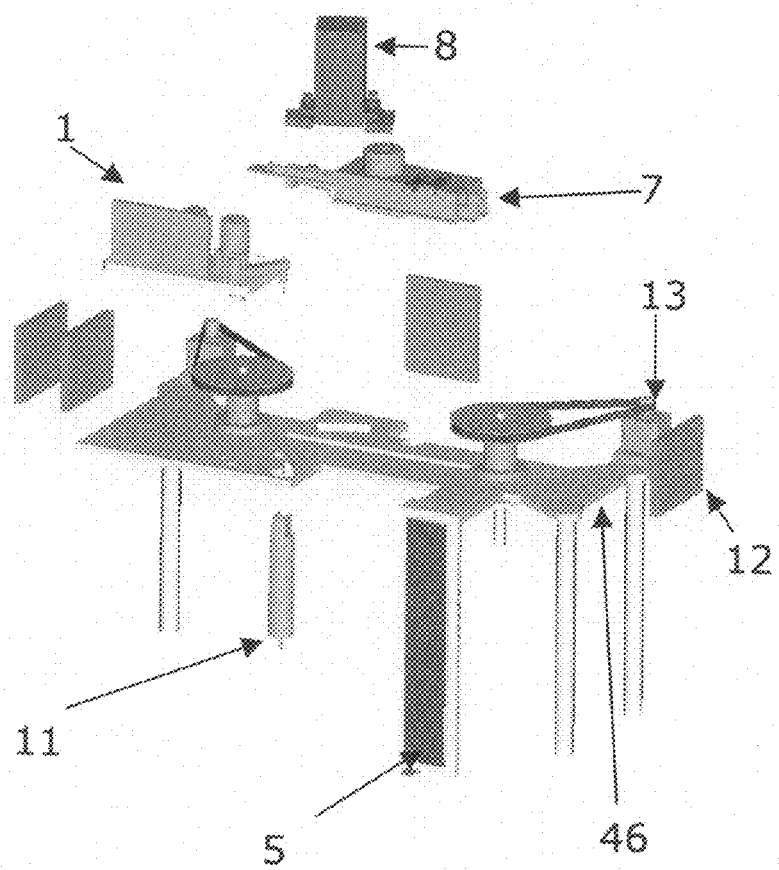
FIG. 7 shows an exploded view of some of the internal parts in the analysis apparatus.

In order to protect the internal parts, preferably a structure having an inner cabinet as structure for the mechanical modules and the hardware (HW) is used, see FIGS. 5 and 7. The internal devices and structures are protected towards the outer environment, by an outer front cabinet shown in FIG. 8. The only openings into the inner cabinet are preferably at the inlet for cartridges 5, where a hatch can be opened. The hatch can be a part of the storage/central beam structure, at the stick waste container 4 and at the liquid waste funnel 11 shown in FIGS. 9 and 10. These three openings are carefully designed in order to avoid air penetration when closed.

The outer back cabinet shown in FIG. 12 serves to protect the outer cooling fins and a fan shown in FIG. 12 or 15. Air can flow through this part of the cabinet.

Figure 18:
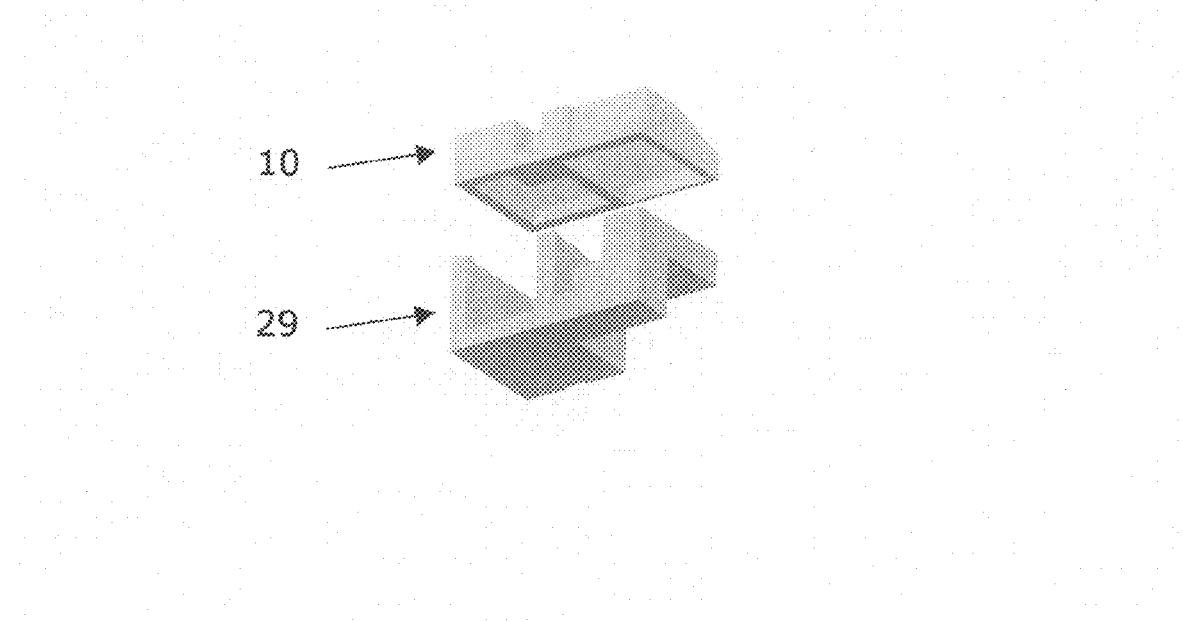
FIG. 18 shows a second embodiment of insulation enclosures.
Figure 19:
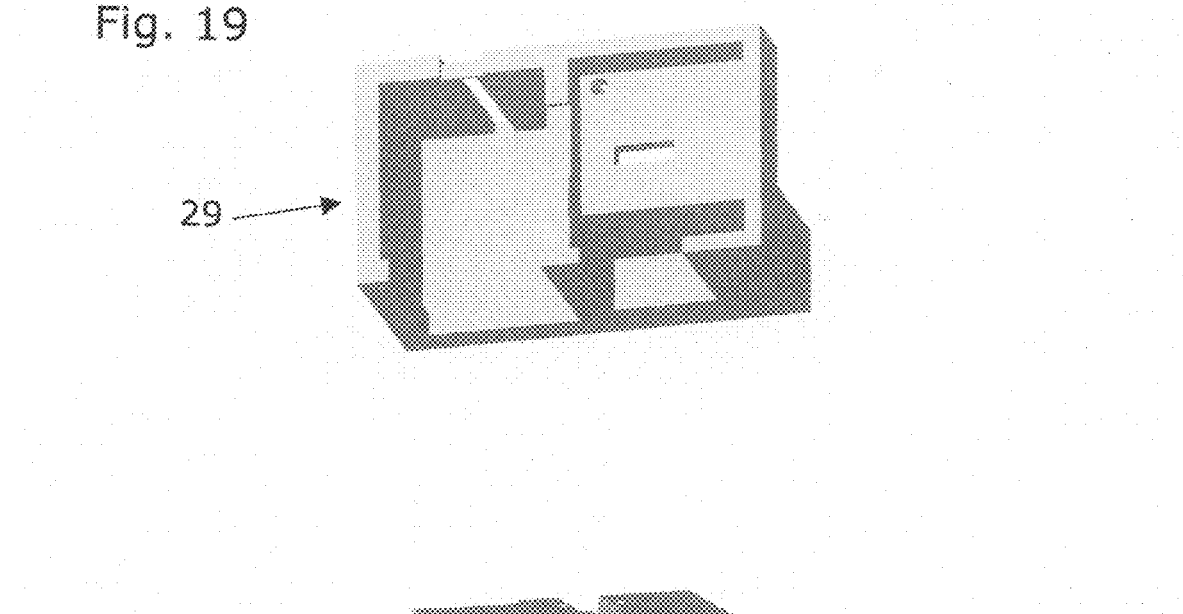
FIG. 19 shows a second embodiment of insulation enclosures.
Figure 20:
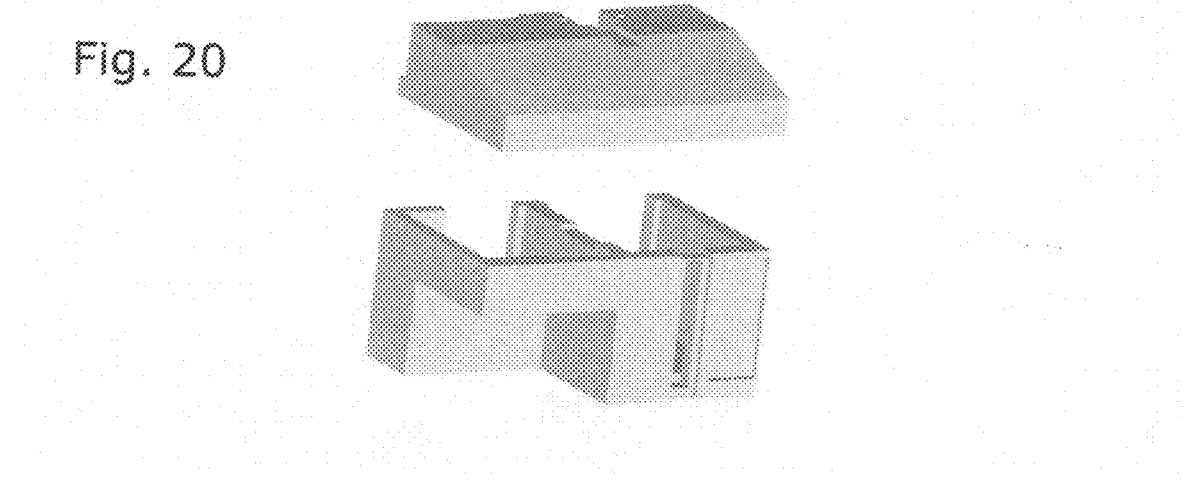
FIG. 20 shows a second embodiment of insulation enclosures.

The insulation enclosures shown in FIGS. 18-20 secure a stable temperature and minimal power consumption for cooling and heating to desired temperatures. They also serve as a moisture barrier together with the outer cabinet.

User Interface

A front door gives the user access to the user interface 19, shown in FIGS. 9 and 10 (keyboard, screen, cartridge load, stickwaste container, diluent container, liquid waste funnel, wet system filter). Furthermore the front door also serves as a double protection for the inner cabinet.

Production and Material

The plate parts of the cabinet are preferably made of stainless steel plates welded together. However other sorts of metals can be used. Other alternative material could e.g. be polymers.

Inner Cabinet

Figure 8:
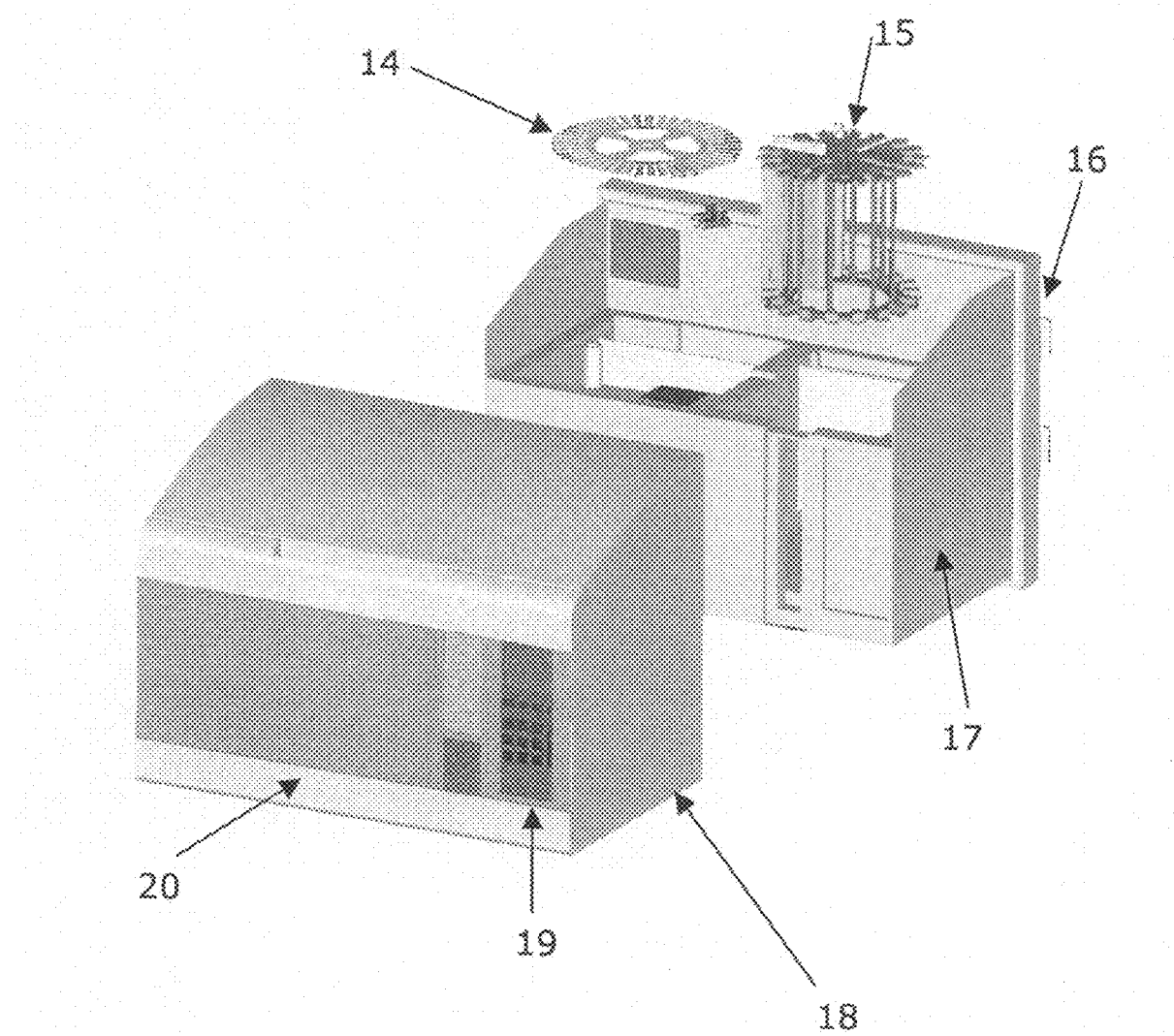
FIG. 8 shows an exploded view of a second embodiment of the analysis apparatus and internal parts.

The inner cabinet shown in FIGS. 8, 13 and 14, is preferably welded of stainless steel plates. It serves as structure for the insulation enclosures, the upper beam, internal and external fans 28, cooling ribs 22 and peltier elements.

A room in the cabinet is reserved for the diluent- and stickwastecontainer, shown in FIG. 14. This room also gives access to the liquid waste funnel and the wet system 1 filter 21.

Peltier Elements and Cooling Ribs

The conditioning or thermostatation of storage and incubator is done with at least one peltier element for each room, see FIG. 14.

A peltier element or thermoelectric heat pump is a solid-state active heat pump which transfers heat from one side of a device to the other.

The outer cooling ribs are placed in a separate cabinet FIGS. 13-15. They could alternatively be placed inside the inner cabinet. A surface treatment of the outer cooling ribs could be necessary to withstand the environment.

The peltier elements, the cooling ribs and insulation between the cooling ribs can be assembled as a sandwich, in order to be removable as a whole or partly from the cabinet. Gaskets between the outer cooling ribs and the cabinet secure the tightness of the cabinet. The peltier elements are placed in connection with the outer cooling ribs in order to provide a more effective heat transfer from the elements. An aluminium bridge can be used to connect the peltier elements and the inner cooling ribs.

The cooling ribs may be placed vertical in the back of the inner cabinet, see FIGS. 13-15, in order to get a short direct transfer of heat from inside to outside. Additional the vertical orientation secures that eventual condensation can be assembled in the bottom of the cabinet and removed.

Furthermore FIGS. 13 and 14 shows the passage for used sticks 23, the passage for liquid waste funnel 24, structure for mounting of beam 25, internal fans 26 and room for diluent and stickwaste 27.

Fans

Preferably a fan for each room 26 and one or two external fans 28 removes the heat energy from the cooling ribs see FIGS. 14 and 15. The fans are preferably constantly running during operation.

Air Guide Plates

Plates for guiding the heated/cooled air are mounted to the inner cabinet or the insulation. Heat guide elements is a possibility for distributing heat/cold correctly in the rooms.

Consumables Room

A room in the left front, see FIG. 9, contains the diluent container 3 and the stickwaste container 4. The room gives access for removing and cleaning the wet system funnel 11 and the filter 21. There are openings from the incubator room for used sticks, funnel, sample tube, diluent tube. The tightness of these openings is secured. Gaskets secure the tightness between the consumables room and the outer front cabinet.

Structure for Central Beam

A structure serves for mounting the central beam to the cabinet. See FIG. 7, 13 number 25.

Central HW (Hard Ware) Board

The central HW board in FIG. 3, and the two RIO (Remote input/output) boards 12, FIG. 7, may be mounted to the inner cabinet or to the beam.

Pressure Release Valve

A pressure release valve compensating for changing temperatures may preferably be used.

Connections

A connection box is placed on the back or the bottom of the main cabinet. The box preferably has connections for milk sample inlet tubes, signal cable, power cable etc.

Milk sample waste could be connected in the same box or in the bottom of the cabinet. Also the connections for external light and alarm preferably passes this connection box. All connections pass the cabinet in IP65 and airtight cable passage components.

Preferably all cables are sealed in order to avoid air movements between inner cables and outer cable protection.

Outer Front Cabinet

The outer front cabinet, shown in FIGS. 9-10, has openings for the reload hatch where cartridges are loaded and for the consumables room.

The display and keyboard are preferably mounted directly to the front plate in order to obtain tightness, see FIG. 9.

The outer front cabinet has IP65 tightening against the inner cabinet backplate and tightening against the consumables room and the frame for the reload hatch.

The outer cabinet can be removed from the inner by releasing locks or nuts in the front plate and pull it towards the operator.

A sensor checks whether the front cabinet is mounted to the inner cabinet.

A thin insulation can be applied by gluing it to the inside of the inner cabinet in order to improve the insulation capacity even further.

Front Door

The front door in FIG. 11, preferably has sensors for ensuring that the door is closed, if the front door is not properly shut preferably a light and/or sound signal will alert the operator.

Preferably the hinges, lock and handle are mounted outside gaskets.

Outer Back Cabinet

Figure 17:
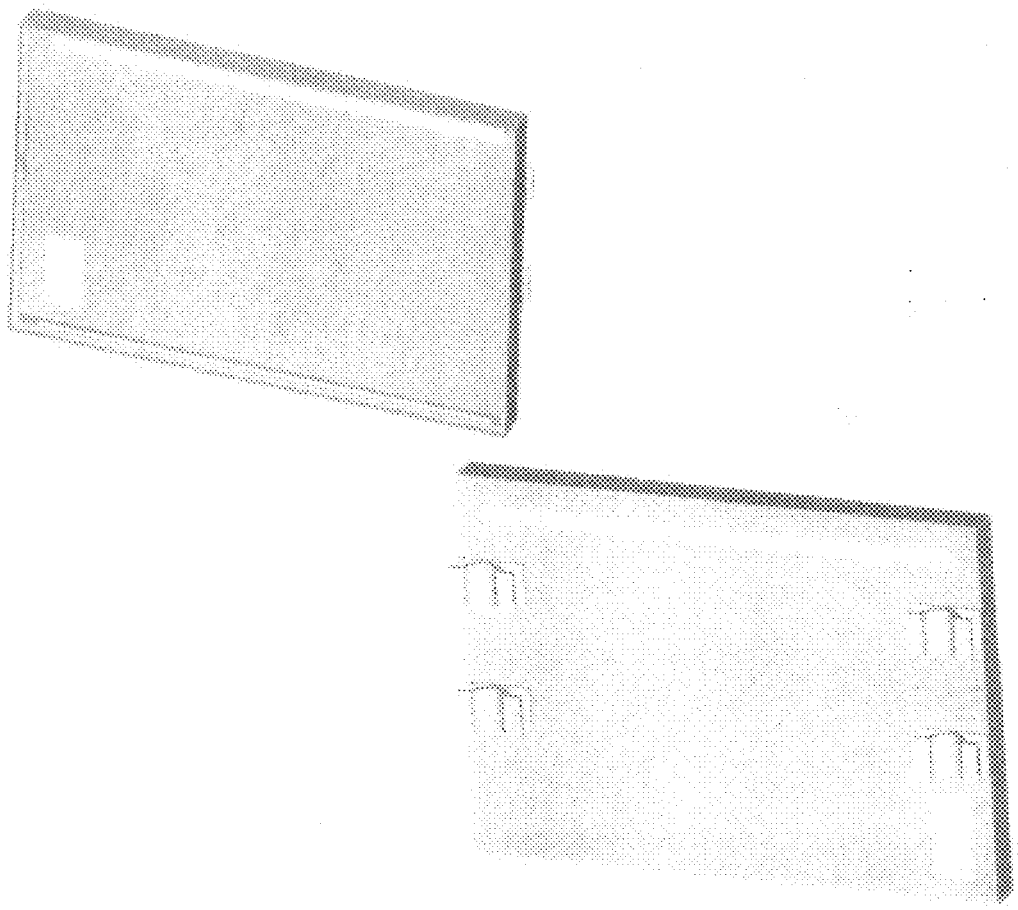
FIG. 17 shows an embodiment of an outer back cabinet.

The outer back cabinet serves as protection for the outer fan and the cooling ribs, and for mounting the AI on to a wall or another suitable surface. The outer back cabinet is shown in FIG. 17. A hole in the outer back cabinet serves as passage for the connection box.

Gaskets secure tightness to inner cabinet. Openings in the bottom and top of the outer back cabinet secures airflow over the cooling ribs FIG. 15. Damping elements between the mounting brackets and the outer back cabinet can be used in order to lower the impact of possible mechanical vibrations from the surface on which the AI is mounted to.

Insulation Enclosures

FIGS. 18-20 shows an embodiment of the different insulation enclosures inside the AI, which are necessary to keep the temperature stable.

The temperature in the storage should preferably be kept at 20° C.+−3° C., and the temperature in the incubator preferably at 25° C.+−3° C. The humidity in the storage should preferably be below 30% RH. The insulation serves to obtain this.

Preferably Expanded polystyrene (EPS) or Polyurethane (PUR) is used as insulation, EPS being easier to obtain UL approval of, with acceptable insulation values.

If EPS are chosen the cabinet will be manufactured by injecting EPS pellets into a mould and applying steam. This will give an insulation house that should be mounted to the inner cabinet.

PUR could be injected between two shells, the outer shell could be the inner cabinet. Obtainable insulation value for EPS is 0.033 W/mK (type F495). This gives insulation thickness of approximately 35 mm for storage. For the incubator the temperature used to be 37° C. For this temperature 20 mm were sufficient. 30-35 mm will probably be necessary for 25° C.

Gaskets between the peltier/cooling ribs sandwich and the insulation are preferably used. Also gasket between the reload hatch frame and the insulation.

Figure 6:
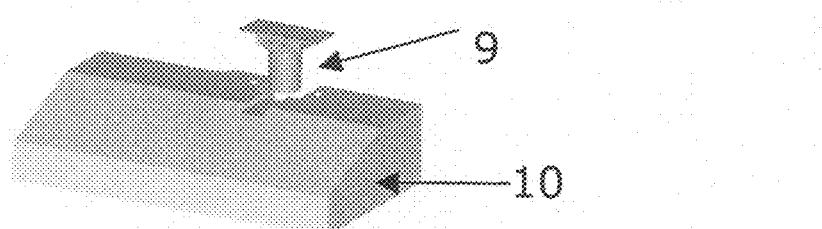
FIG. 6 shows an embodiment of top insulation 10, comprising a tube pump 9.

The top insulation shown in FIG. 6 can be lifted to give access to the dry and wet system. A gasket between the top insulation and the insulation enclosure is preferably used. The top insulation could alternatively be made of two parts allowing separate access to incubator and storage.

A lock system between the top insulation and the insulation enclosures is preferably used.

A sensor will detect whether the top insulation is present or if it has been removed. If it has been removed and not put back into place a signal will alert the operator.

Beam

The beam shown in FIG. 24, serves as structure for mounting storage disc 48, incubator disc 72 and their drives and sensors, stickmover 7, wet system 1, optical reader 8 and frame for reload hatch 5. The idea with the beam, is to mount the elements with precise tolerance demands to a rigid structure as close as possible to their interacting areas. The beam is preferably manufactured of stainless steel. However aluminium may also be used. The beam is preferably mounted to the cabinet with slides enabling a retraction of the beam from the cabinet.

Storage/Incubator Drives

The function is to index the incubator and storage turntables in order for both to be positioned correctly, and thereby allowing a stick to be transferred from storage to incubator. Both drives are nearly identical, except for the fixture for the sensors.

Applied Solution

Figure 30:
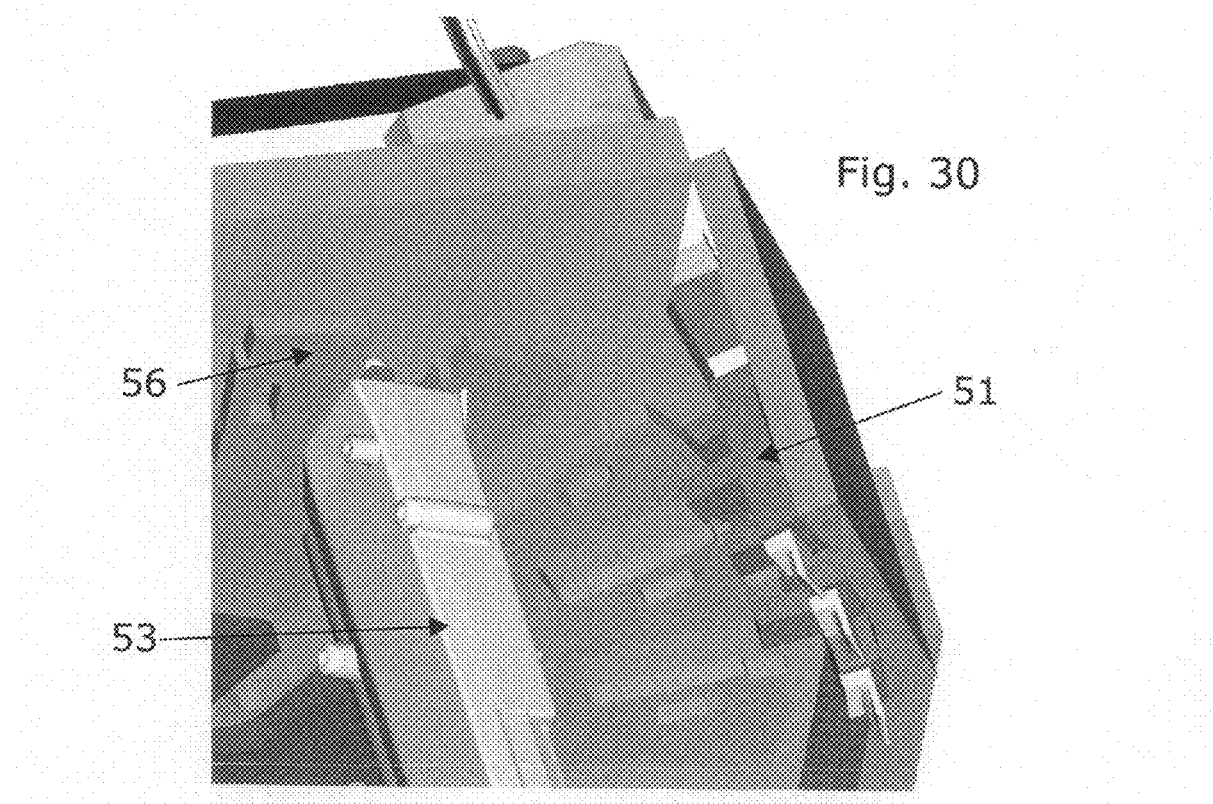
FIG. 30 shows the sensors for positioning of the storage carrousel.
Figure 31:
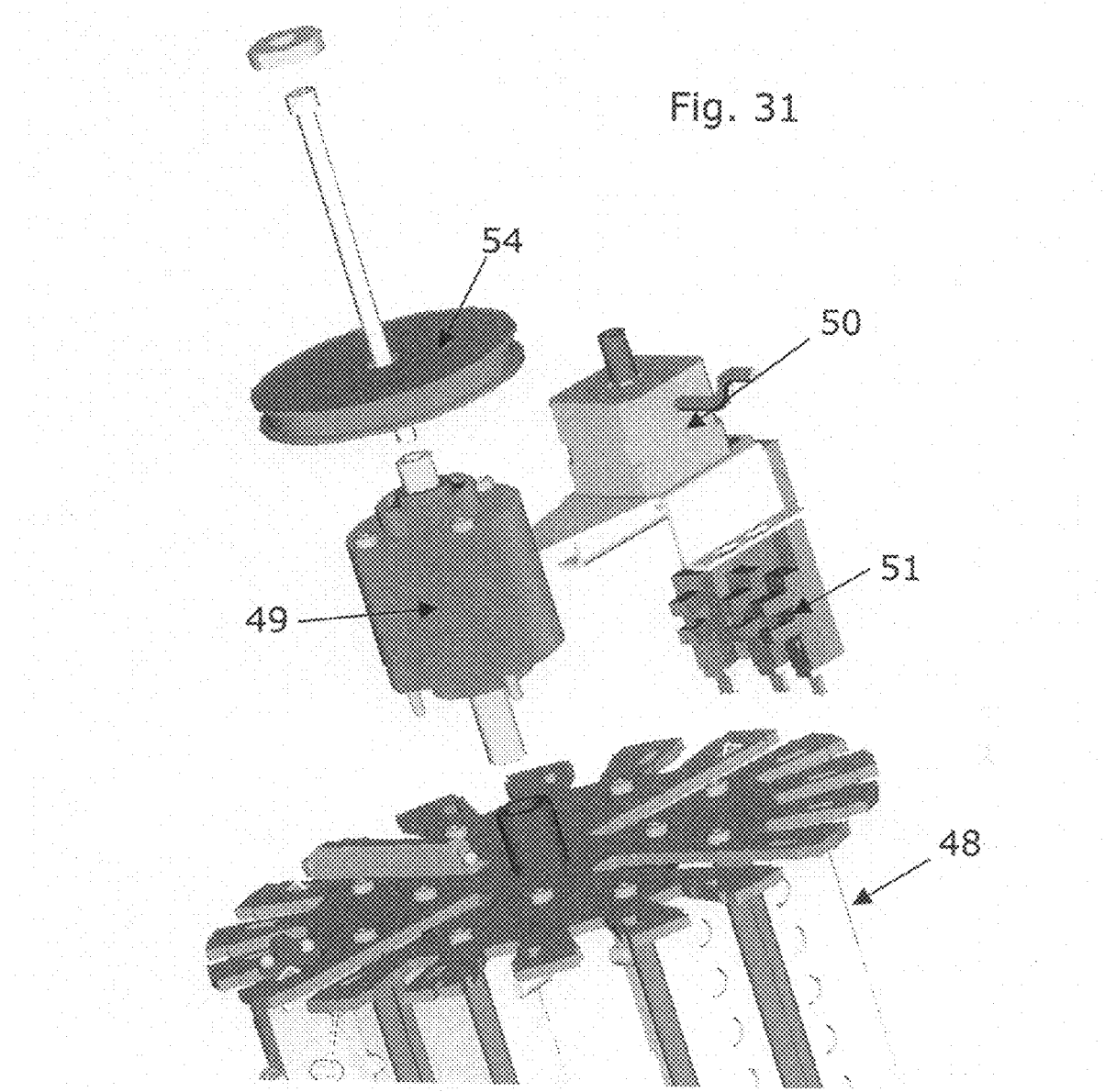
FIG. 31 shows an exploded view of the driving assembly for the storage carrousel.

FIGS. 29-31 shows a view over a first embodiment of the driving assembly. The drive preferably consists of a 200 increment stepper motor 50 with a press fit pulley, a toothed belt 55 and a bearing assembly comprising shaft with pulley 54, two sealed ball bearings and a machined bearing house 49 secured to the beam. The stepper motor and sensors 51 are bolted to a mounting plate that is oriented towards the bearing center by a long hole in the plate and a positioning dowel pin in the beam. The mounting of bearings, motor and sensors in one unit, enables the SW calibration values for the positioning of the IM/SM discs, to be measured before mounting the drive to the AI beam. This is an advantage for the production and field service. The storage/incubator carrousels 48, 72 can be dismantled by loosening the screws mounting the mounting plate to the beam, removing the timing belt 55 and sliding the mounting plate 52 to a bigger radii. By doing this the sensors are free of the carrousel. See FIG. 30.

The nut is removed for dismantling of the timing pulley 54, see FIG. 31. The screw head has external thread for the nut. After the nut has been removed the screw can be removed for dismantling of the Storage Module/Incubator Module carrousel. The screw and the screw-head have opposite threads.

The preferred Data and specifications is presented below

| | |
|---|---|
| Drive power needed: | max. 2 W |
| Ratio: | 9:1 |
| Motor pulley: | 15 teeth |
| Timing pulley: | 135 teeth |
| Belt pitch: | 2 mm |
| Belt profile: | MR2 × 6 mm(width) |
| Resolution: | 0.04°(~0.1 mm on the incubator disc/storage outer perimeter) |
| Intended indexing angle: | incubator 8° storage 18° |
| Intended time for 180° index: | Storage 4.5 s |

An Embodiment of Operation Mode of Turntables
Function of the Drives

Figure 42:
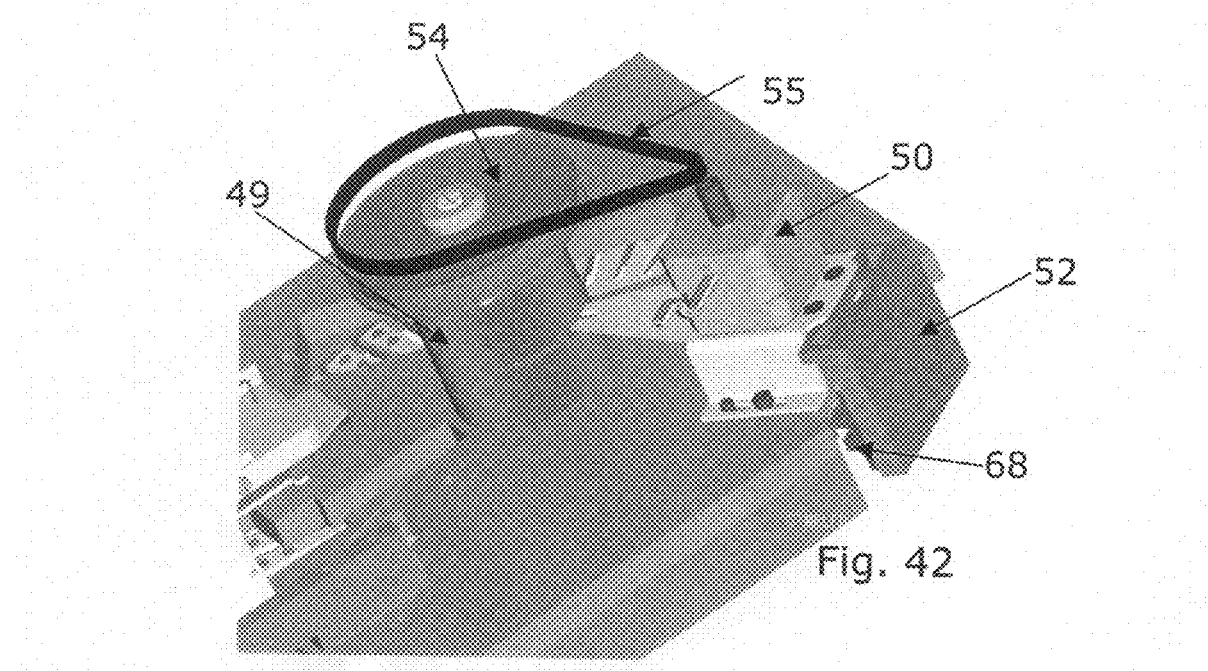
FIG. 42 shows an embodiment of driving assembly for the incubator disc.

To index the incubator and storage turntables in order for both to be positioned correctly, and thereby allowing a stick to be transferred from storage to incubator.
An Embodiment of Applied Solution FIG. 42 shows a view over the driving assembly. The drive preferably consists of a 200 increment stepper motor 50 with a press fit pulley, a toothed belt 55 and a bearing assembly comprising shaft with pulley, two sealed ball bearings and a machined bearing house secured to the upper beam. The stepper motor 50 is bolted to a mounting plate.
Storage Module
Storage Turntable
Function The storage turntable 48 stores the cartridges, loaded by the operator, and presents them to the stick-mover that sweeps out the DS from the top of the cartridge, see FIG. 33.
Storage Preferably:

Have 14 CS-cartridges.
Have 3 LS-cartridges.
Have 1 desiccant-cartridge.
Enable renewal of cartridge through reload hatch.
Enable thermal and humidity conditioning of sticks.
Enable reading of cartridge bar-code label.
Present cartridge for stick-mover.
Enable "dry-run" of stick-mover, so that it can empty incubator without the need of inserting a fresh DS.
Applied Solution It has been decided that the storage preferably is a turntable carrousel 48 shown in FIG. 28.

In the carrousel each stick cartridge is stored in a keeper 53, which is a box open in the top. The keeper is hinged in the bottom so that it can be swung out to present the cartridge to the operator in a horizontal position, illustrated in FIG. 33. In the upright position the keeper is preferably locked in place by a keeper spring 58, 59 or 64, showing two embodiments of locking arrangement, see FIGS. 32 and 35. The keeper is forced outwards by a spring placed at its hinge 61. When the reload hatch is opened the keeper spring is actuated to release the keeper.

The carrousel is preferably a squirrel cage construction—two discs interconnected by spacer rods 60, illustrated in FIG. 33. The upper disc is equipped with a flange, which is bolted onto the shaft of the drive. Upper disc is cut out in a pattern forming places for the cartridges that stick out of the top of the keepers. Each cut-out is flanked with a cut-out for the keeper springs that are locking each keeper in the vertical position, see FIG. 35. The bottom disc is ring-shaped and supports the hinges and springs for the keepers.

Please refer to section "Cartridge" for the interaction between Cartridge and keeper/storage.

At each keeper the upper disc have a detection blade providing optional feedback when interacting with photo-interrupters. One detection blade is preferably prolonged to provide a "per revolution" sensing.

Alternatively a slit is used for the revolution sensing. Sensor and prolonged detection blade could be omitted if the Bar-code reader is integrated in the storage, as it identifies the cartridges.
Function Sequence
Removing Used Cartridge and Loading Full Cartridge:

When the reload-hatch illustrated in FIG. 9, is open a cartridge keeper is presented through the hatch opening. The operator pulls the used cartridge out of the keeper and insets a new one.
Closing Hatch and Locking Keeper in Carrousel:

The operator closes the reload-hatch that is hinged in the bottom. The reload-hatch pushes the keeper that also swings up.

Figure 100:
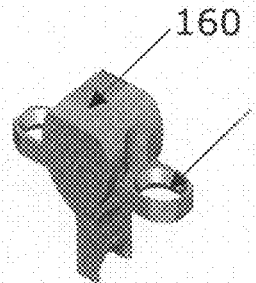
FIG. 100 illustrates a perspective view of how a cartridge comprising sticks, movable bottom and a plunger preferably is mounted into a cartridge keeper.

During the closing, a depressor arm 116 in the reload hatch, driven by a coulisse 117, pushes the cartridge further down into the keeper, against the force of the pusher spring 166 placed in the bottom of the keeper, see FIG. 100.

The coulisse 117 is a part that is pushed by the reload hatch, when the reload hatch is closed. Furthermore the coulisse is provided with a track that guides a pin in the depressor, making the depressor rotate, see FIG. 79.

This allows a protrusion 65 on the back of the cartridge to pass under the upper disc 56, illustrated in FIGS. 36 and 37. When this has occurred the depressor 116 arm retracts, cartridge jumps up until the mentioned protrusion rests against the underside of the upper disc—making the chain of tolerances as short as possible, ensuring that each cartridge is levelled in respect to the stick-mover and tunnel.

When the reload-hatch is almost closed, the flipper 123 pushes the keeper the rest of the way. The flipper is then retracted from the keeper by the retractor arm 122 in the reload hatch. This leaves clearance between the reload-hatch and keeper, approximately 2±1 mm. The backside of the cartridge rests against the edge of the cut out in the upper disc—keeping the position tolerances low.
Opening the Reload-Hatch and Releasing Keeper:

The AI opens the reload-hatch as it releases a pawl locking the reload-hatch in the closed position.

Figure 79:
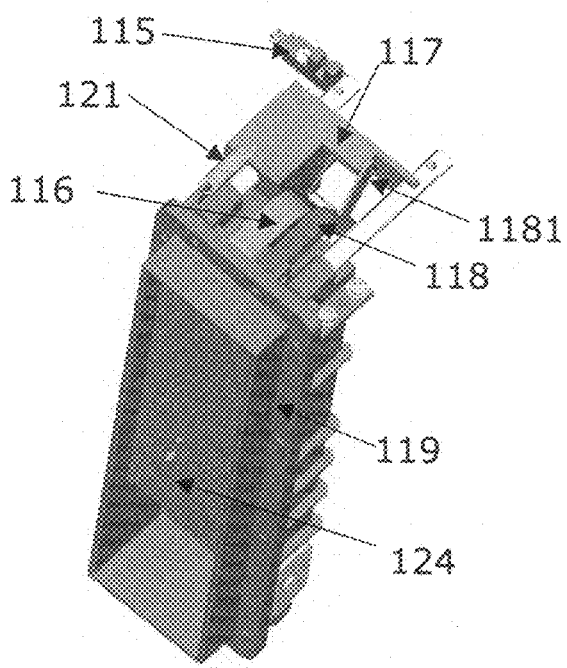
FIG. 79 shows an embodiment of a reload hatch comprising a coulisse, depressor arm, release arm, reload hatch frame.
Figure 80:
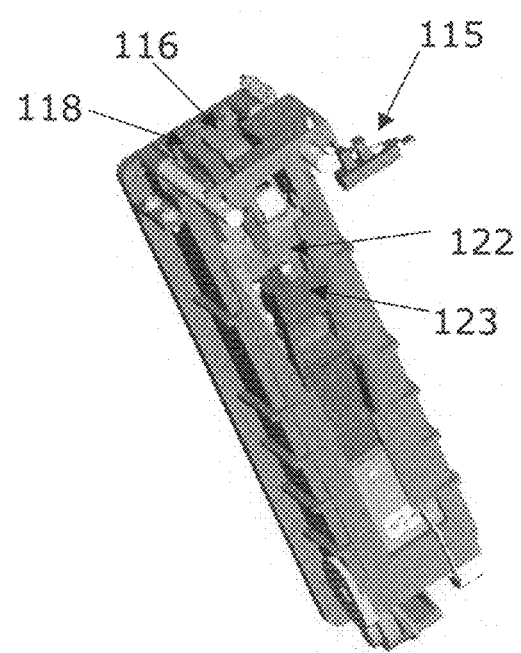
FIG. 80 shows the reload hatch above from a different angle exposing a sensor the retractor and the flipper.
Figure 81:
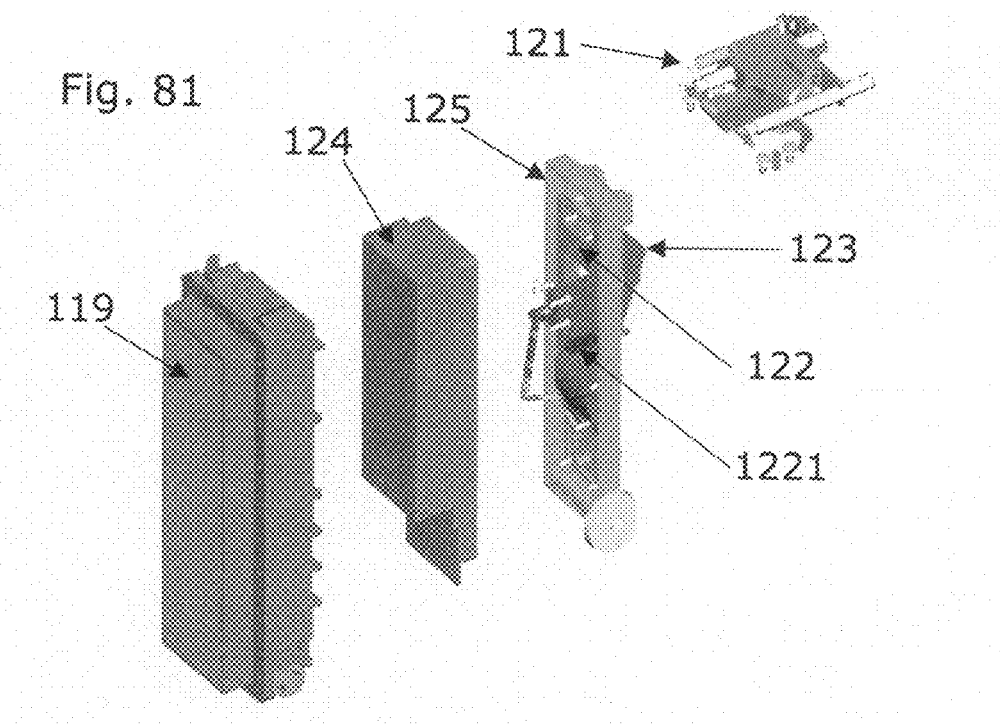
FIG. 81 shows an exploded view of the reload hatch.
Figure 90:
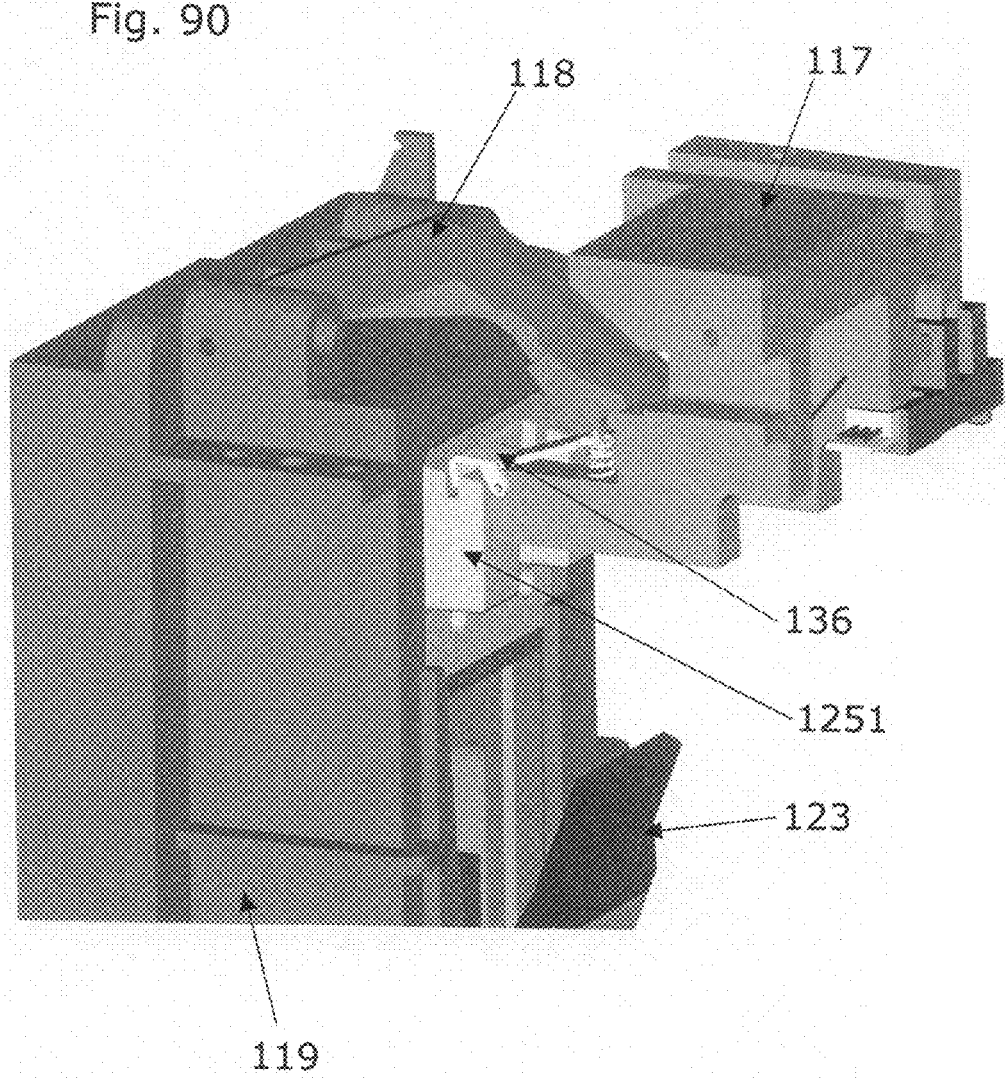
FIG. 90 shows the assembly shown in FIGS. 88 and 89 from the other side and with a few devices removed, illustrating the spring loaded catching devices for catching the hatch.

The reload-hatch contains a release arm 118 driven by a coulisse 117 that actuates the keeper spring 121, releasing the keeper when the AI opens the reload-hatch, see FIGS. 79 and 90.

Figure 88:
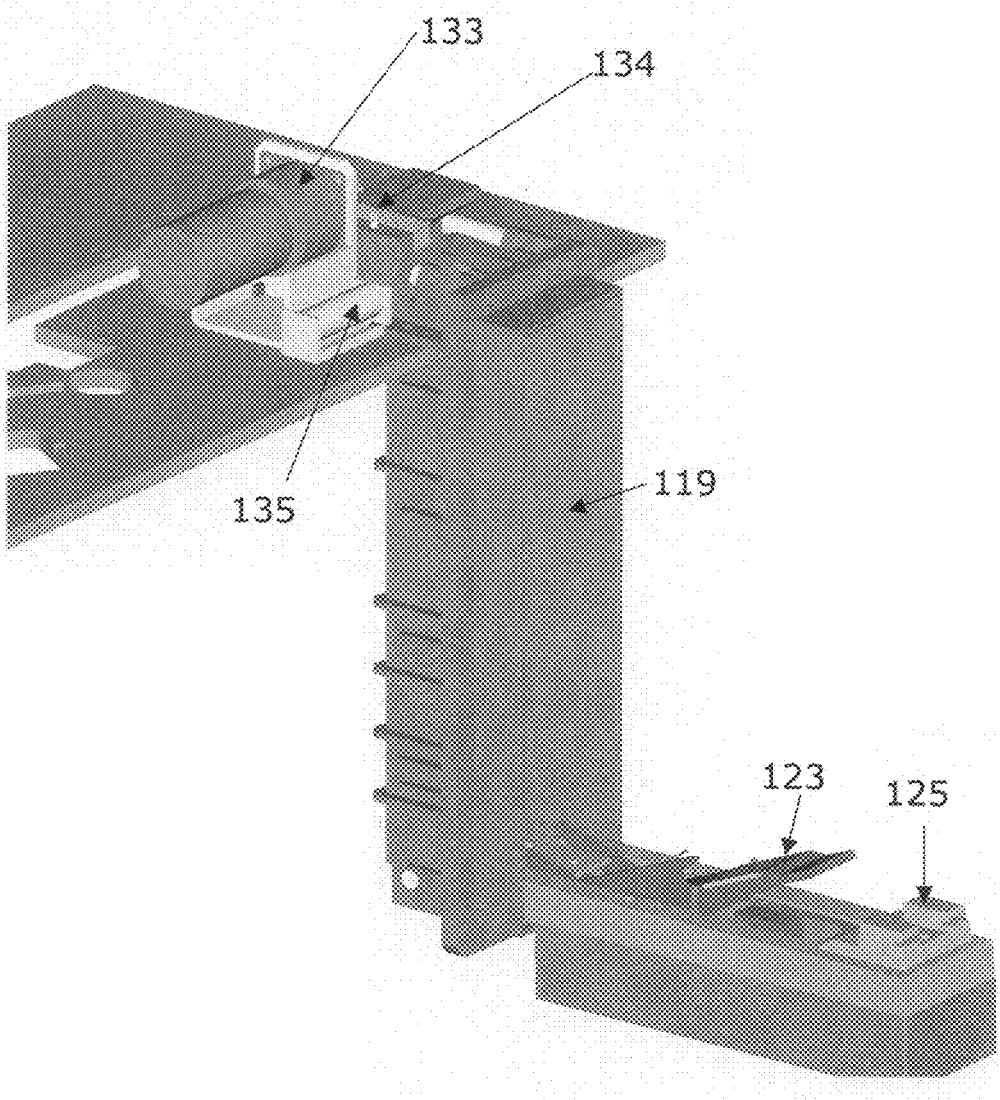
FIG. 88 shows an embodiment for closing the hatch comprising a motor, teethrack and a solenoide mounted on top of the central beam.
Figure 89:
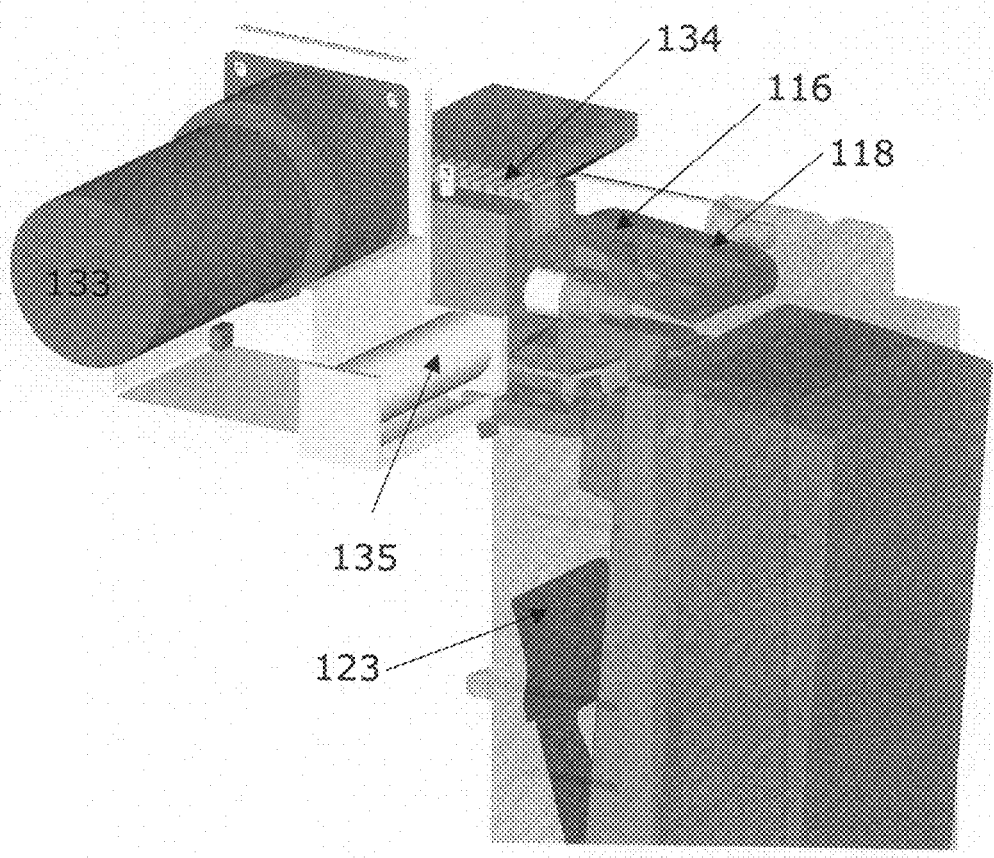
FIG. 89 shows an enlargement of the assembly shown in FIG. 88.

When the keeper is released, it swings out and rests against the partly opened reload-hatch. The operator swings the reload-hatch down, while the keeper follows its motion, until the reload-hatch rests against a stop in a horizontal position, see FIGS. 10 and 88.
Data and Specifications
Upper and Lower Disc Preferably made in stainless steel—3.5 mm thick however also seawater resistant aluminium may be used.

The discs are preferably manufactured by using laser cutting, but could be stamped at very high volumes.
Flange The flanges in the functioning models are turned and milled in aluminium. However composite injection moulding could be more profitable for high volume production. The flange may be redesign since the drive also can be placed on the upper beam, instead of on a lower base plate Spacer Rod The spacer rods 60 in the functioning models are turned in aluminium. For higher volume manufacturing they may be turned in glass fibre or reinforced composite.

Screws

All screws can be of the thread forming type, reducing the cost of parts as simple drilled or stamped holes are used. The formed thread is the Metric-standard, meaning that standard M-screws can be used in the need of replacement.

Springs

Springs are preferably made of stainless steel.

Storage Keeper

Function

The function of the keeper shown in FIG. 33, 34, 35, 100 is to maintain and position the cartridge in the storage. The positioning has to be adjusted to the height of the stick mover. Also the cartridge has to be oriented radially, so that the stick can be guided in a direct and straight line to the incubator.

Applied Solution

The keeper itself has been made as an item in POM. In the keeper the guide pins 164 for the plunger 160 has been mounted by means of circlips. Furthermore, a spring loaded bottom stop 163 has been mounted to secure that the cartridge is being guided towards the upper storage disk. This is shown in FIG. 100. Internal lead-in in the keeper and the cartridge and external lead-ins in the plunger ensure easy mounting of the cartridge, see FIGS. 100, 101 and 102.

Figure 101:
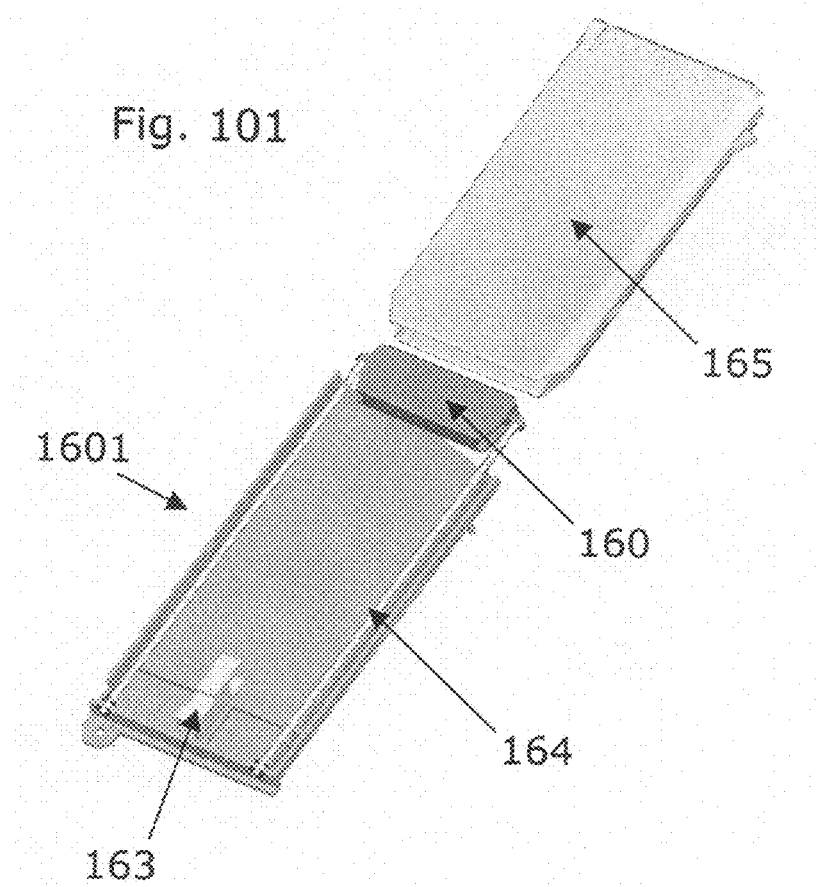
FIG. 101 shows a cartridge and cartridge keeper.
Figure 102:
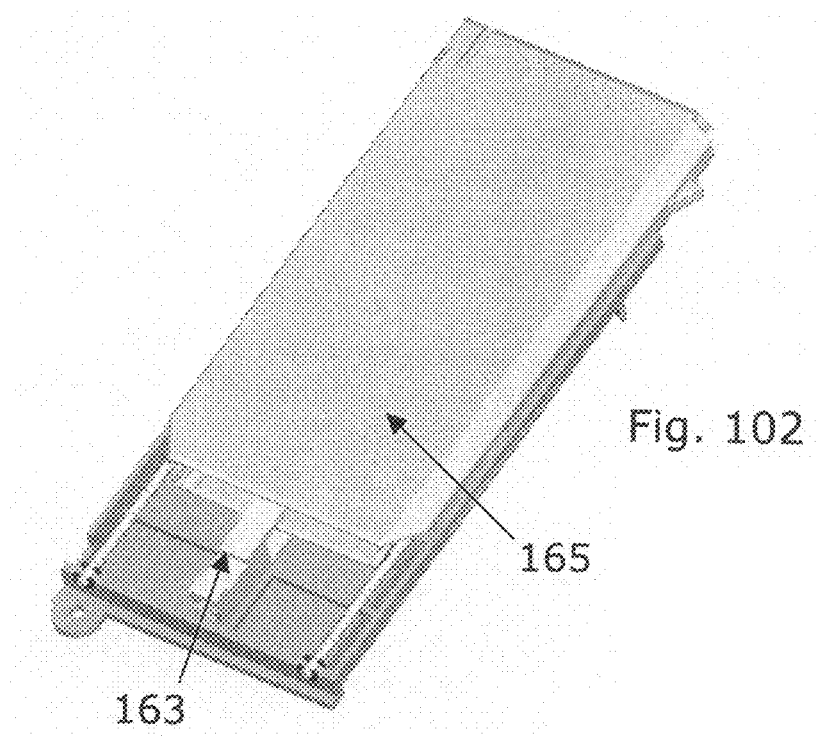
FIG. 102 shows a cartridge loaded into a cartridge keeper.

When the cartridge has come approximately ¾ way down the keeper, it preferably meets a snap-lock, which locks the cartridge in proportion to the keeper, see FIG. 101. In the snap-lock there is approx. 5 mm free space, which is used for the movement when positioning towards the upper storage disc.

Radially the cartridge is oriented partly by minimal air between the front of the cartridge and the upper storage disc, and partly by two projections on the cartridge, which have minimal air for the periphery of the disk. When the cartridge is being mounted by means of the reload hatch, it is being pressed down to the bottom stop of the keeper shown in FIGS. 100 and 101. When the cartridge is in storage, the reload hatch depressor loosens up, and the cartridge is being positioned in a given height, which has been adjusted by the tap on the cartridge. In this way, it will have the smallest possible tolerance chain in relation to the stick mover.

Preferred Data and Specifications

Injection moulded in POM as two items screwed together.

Physical Data, LC Keeper:

Main dimensions (L×W×D): 180×21×85 mm

Physical Data, CC Keeper:

Main dimensions (L×W×D): 180×21×30 mm

Plunger

Function

Figure 98:
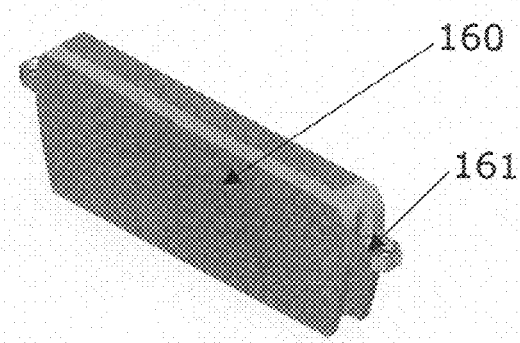
FIG. 98 shows a plunger for long sticks.
Figure 99:
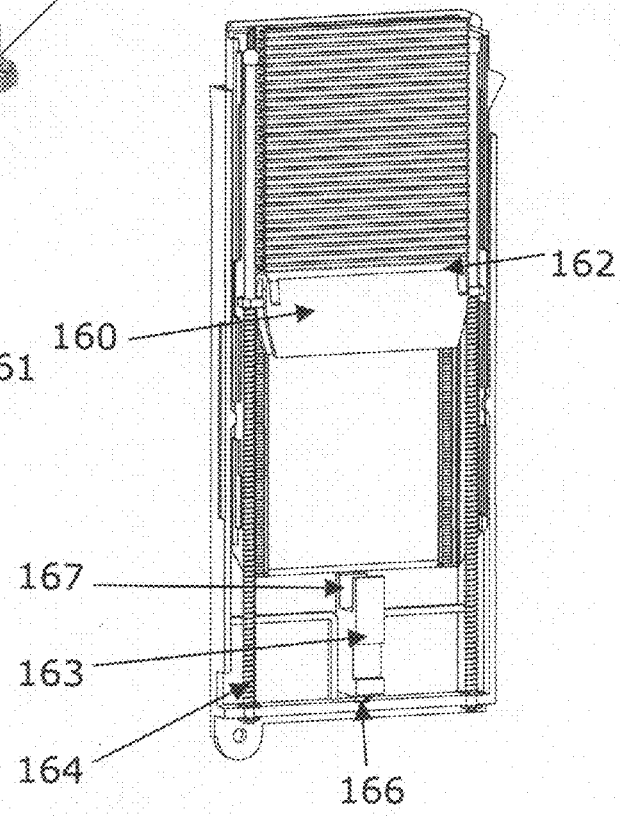
FIG. 99 shows a plunger for short sticks.

The plunger 160, shown in FIGS. 98 and 99, exerts an upward force on the sticks in the cartridge to move the stack of sticks up when a stick is removed, presenting next stick for the stick-mover. The plunger is forced upwards by two springs.

The plunger preferably constantly supplies the bottom with an upright force to secure its functions.

Applied Solution

The plunger has preferably been designed in a way that it smoothly fits into the keeper, see FIGS. 98 and 99.

The only integration for the plunger is the vertical guide way in cartridge 164. Thus the plunger is preferably unlocked as much as possible at all other integrations, see FIG. 100.

The plunger preferably gets its power from the two springs, which have been placed in the sides and are guided on Ø 3 mm stainless stiffeners shown in FIGS. 100 and 101.

Figure 54:
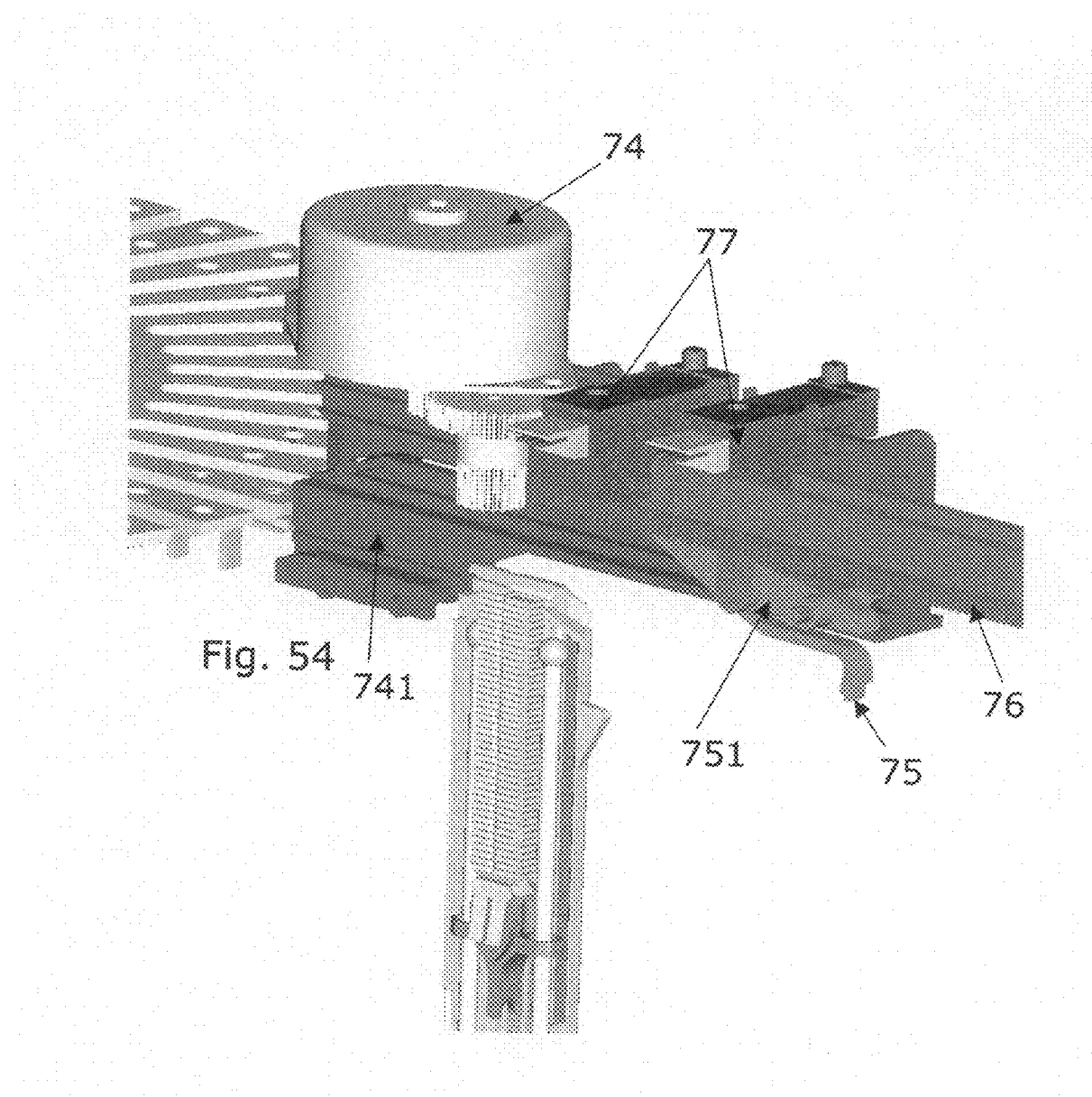
FIG. 54 shows a cross-section of the stickmover assembly and cartridge comprising sticks of the shorter kind.
Figure 55:
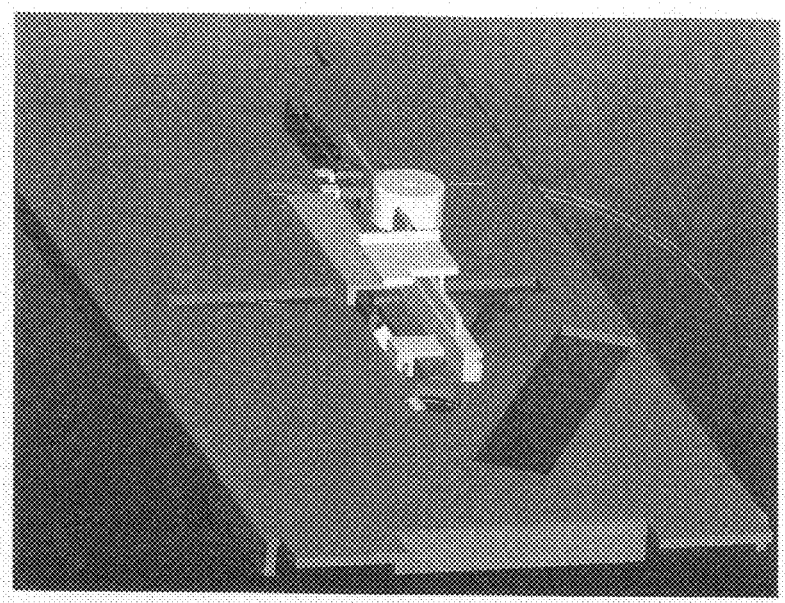
FIG. 55 shows a view of the stickmover from above.
Figure 56:
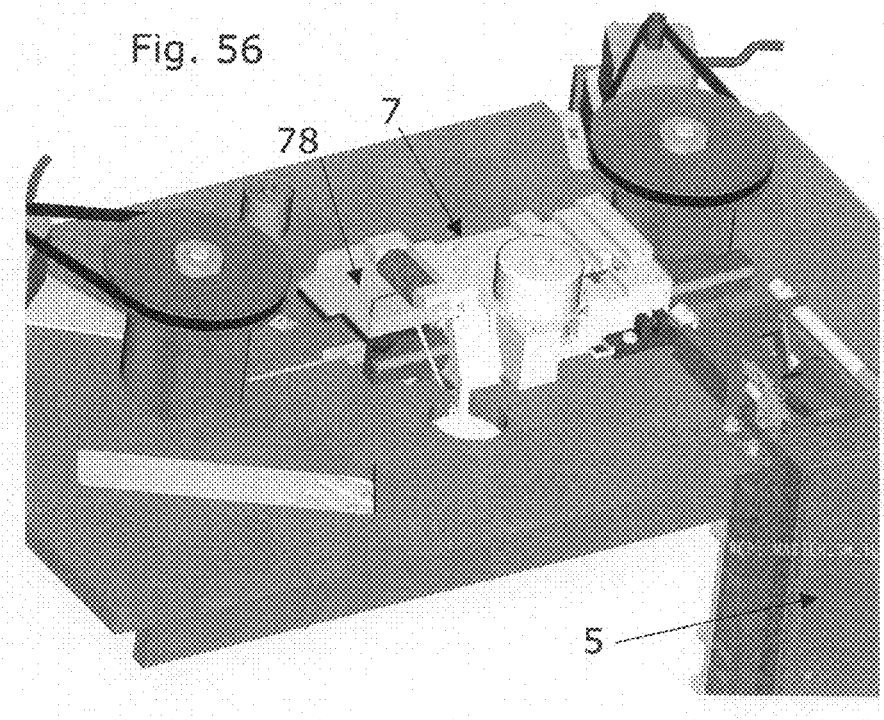
FIG. 56 shows the stickmover device mounted between the storage drive assembly and incubator drive assembly.
Figure 57:
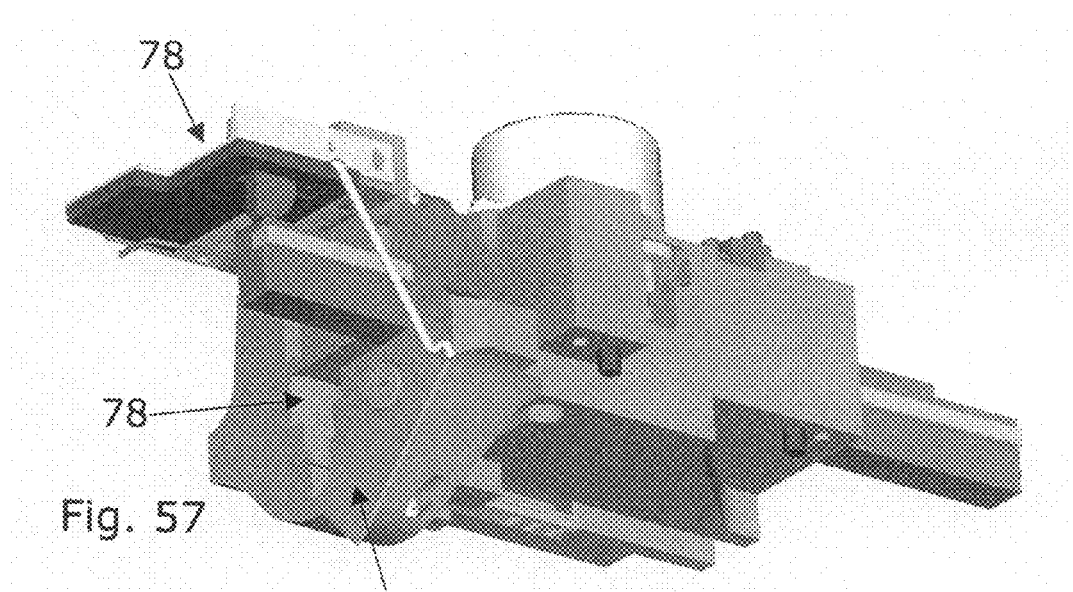
FIG. 57 shows a side view of the stickmover device wherein the opening/closing hatch is shown in open position.
Figure 58:
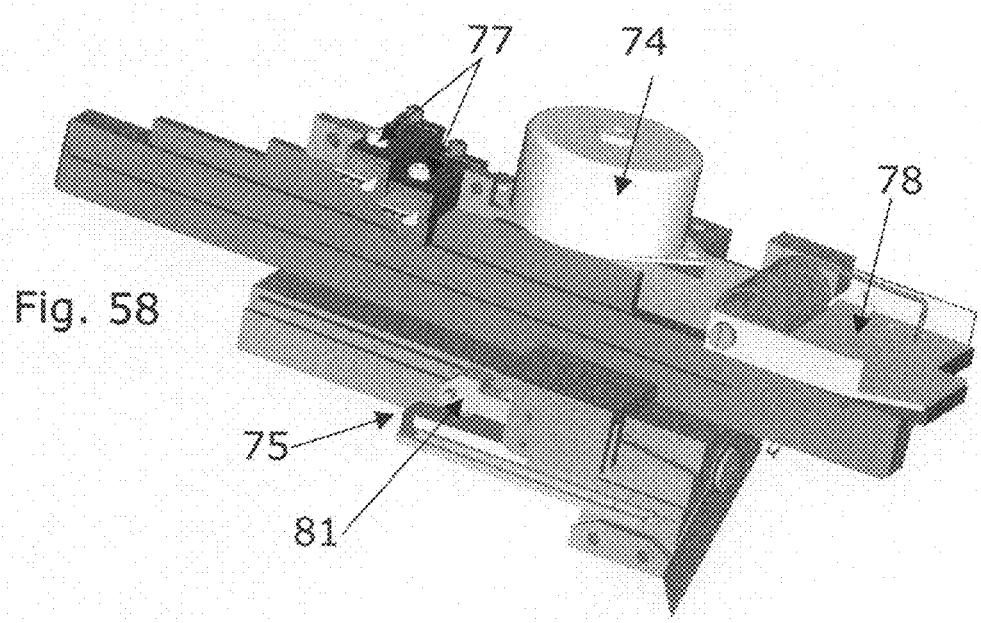
FIG. 58 shows a view from the other side of the stickmover device wherein the stickmover pawl is pushing a stick of the longer type and wherein the opening/closing hatch is open.

The springs in the Lateral Cartridge (LC) shown in FIG. 101, are heavier than in the Colorimetric Cartridge (CC) shown in FIG. 54, due to a larger need for force for increased friction and weight. The heavy springs has a built-in length which is slightly larger, and which is possible due to the fact that the 50 sticks in the LC take up less space compared to the 100 sticks in the CC.

The LC plunger 160 shown in FIG. 98, has been made by milling POM due to very good friction properties. The CC plunger also shown in FIG. 99, has preferably been injection moulded in POM.

Conditioning Humidity and Ammonia Content in Storage Chamber

Function of the Conditioning

The chemistry in the sticks is sensitive to humidity ($H_2O$) and ammonia ($NH_3$), both represented in a stable environment. When the operator changes cartridges, a certain amount of air exchange to the ambient surroundings will take place, and chemistry will therefore be exposed to the above-mentioned components. The preferred levels are that relative humidity is to be kept below 30%, and ammonia is to be kept below 3 ppm. Stable environment in particular can be up to 100% RH and 20 ppm $NH_3$ at 45° C.

Applied Solution

Figure 114:
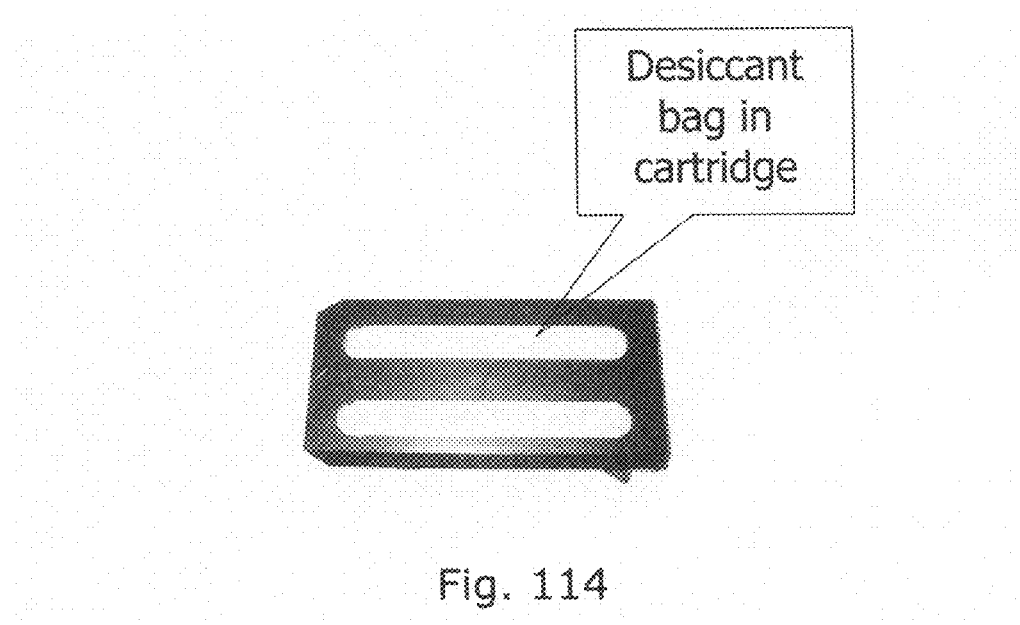
FIG. 114 shows a second embodiment of a cartridge for storage of desiccant bags.
Figure 115:
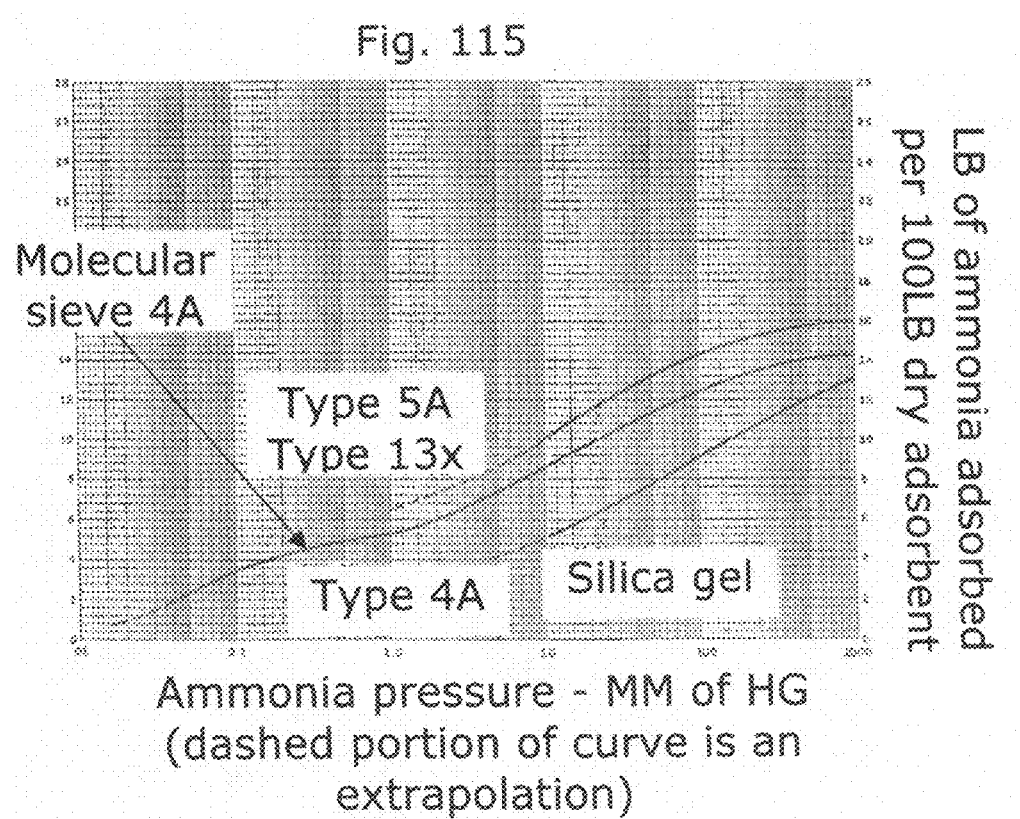
FIG. 115 shows a diagram illustrating LB. of ammonia adsorbed per LB dry adsorbent in relation to ammonia pressure—MM of HG
Figure 116:
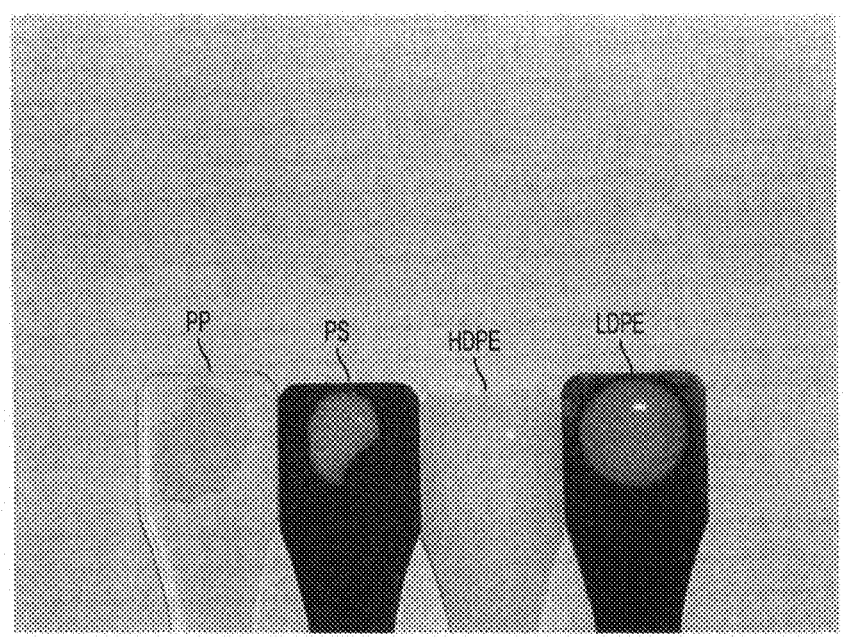
FIG. 116 shows different types of material (PP, PS, HDPE, LDPE) for use in manufacturing of sticks and how fluid behaves when it gets in contact with the material.

A 4A molecular sieve, see FIG. 114, with the ability to adsorb both ammonia and water gives the best overall solution, since it retains its ability to adsorb water molecules over a much wider spectrum of temperature than other desiccants. The preferred way to gain access to the desiccant is through the reload hatch, and the preferred overall solution is therefore to allocate a place in the storage turntable to a desiccant cartridge. The physical dimensions of this "desiccant cartridge" are the same as the lateral stick cartridge, as it gives the largest volume (=high capacity) and surface (=fast response). A desiccant cartridge would consist of a perforated lateral stick cartridge with an app. 50 g. of desiccant in pellet size 1-1.6 mm. As with the 'stick' cartridges, desiccant cartridges are delivered individually in sealed bags. Change of a desiccant cartridge is similar to the change of a lateral cartridge. Airflow through the desiccant is achieved by letting the storage carrousel slowly rotate, when no sticks are required.

Control Strategy, Humidity and Ammonia:

The humidity level is monitored in the AI, and exchange of desiccant will be based upon a time/humidity profile: as the operator is notified about the need to change a lateral or calorimetric cartridge, the AI checks two parameters:

Actual humidity level: should it exceed 25% (Assuming a total exchange of air to an environment with 100% RH and 20 ppm $NH_3$ at 45° C.) for instance, the desiccant cartridge must be changed.

Time elapsed since last change: should it exceed 45 days (Assuming a total exchange of air to an environment with 100% RH and 20 ppm $NH_3$ at 45° C.) for instance, the desiccant cartridge must be changed.

Preferred data and specifications:

| | |
|---|---|
| Nominal pore diameter: | 4 angstroms(0.4 nm) |
| Type of crystal structure: | cubic |

| | |
|---|---|
| Amount of desiccant: | ~50 g |
| Bulk density: | |
| Nominal consumption (estimated): | 1 cartridge/week |
| Worst case consumption (estimated): | 3 cartridge/week* |
| Ammonia capacity: | see next slide |
| Water capacity (at 55% RH@20°): | 22% wt |
| Water content (as shipped): | 1.5% wt. (max) |

One set-up, is a lateral cartridge with stamped or drilled holes and loaded with desiccant, see FIG. 114, in a permeable (Gore-Tex) bag. The moulded cartridge will be bigger and perforated with small holes. This may at least give 2 benefits:

Higher capacity as a result of higher volume of desiccant, therefore longer exchange rates.

Faster response as the water and ammonia molecules would not have to pass the primary barrier, namely the material of the bag, and thereby minimising the exposure to the chemistry.

Positioning of Storage Module Carousel

Figure 38:
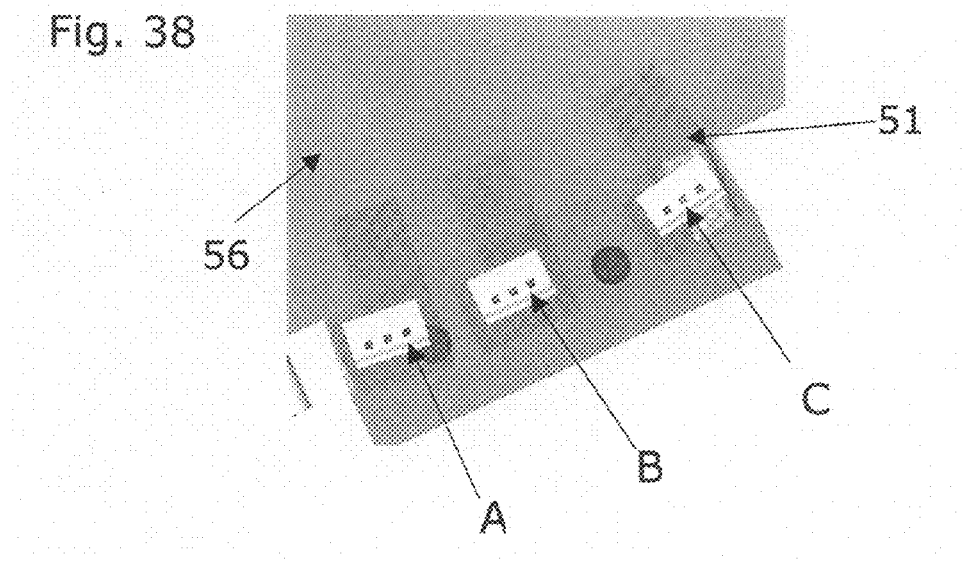
FIG. 38 shows the sensors in the storage for positioning of the storage carrousel, wherein the carrousel is in a first position.

Registration of 360°: 360° when A0/B0/C1 is registered, see FIG. 38.

Registration for tunnel positioning during operation: Sensor C is used for counting steps from interrupt from sensor to tunnel position. (C may also be used during initialisation. A is preferably only used for the 360° signal, B is preferably only used during power up).

360°: A0, B0, C1 (0: sensor is free, 1: sensor is interrupted)

A second embodiment for obtaining a pr revolution signal is using a hall-effect sensor placed at the periphery of the storage and a magnet placed at the storage disc.

A third embodiment for obtaining pr revolution signal is using a blade that protrudes further than the rest of the blades on the storage disc and a photo sensor.

At power up: Storage in tunnel position (sticktransfer is possible) is registered by A1/B0/C0, illustrated in FIG. 38.

FIG. 38 illustrates 360° seen from the bottom of AI.

Figure 39:
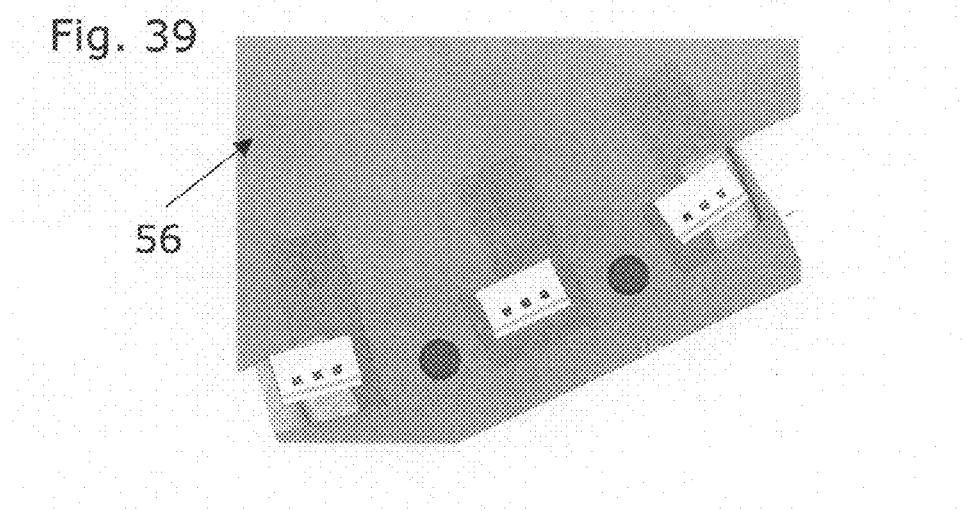
FIG. 39 shows the sensors in the storage for positioning of the storage carrousel, wherein the carrousel is in a second position.

FIG. 39 illustrates Power up.

Figure 40:
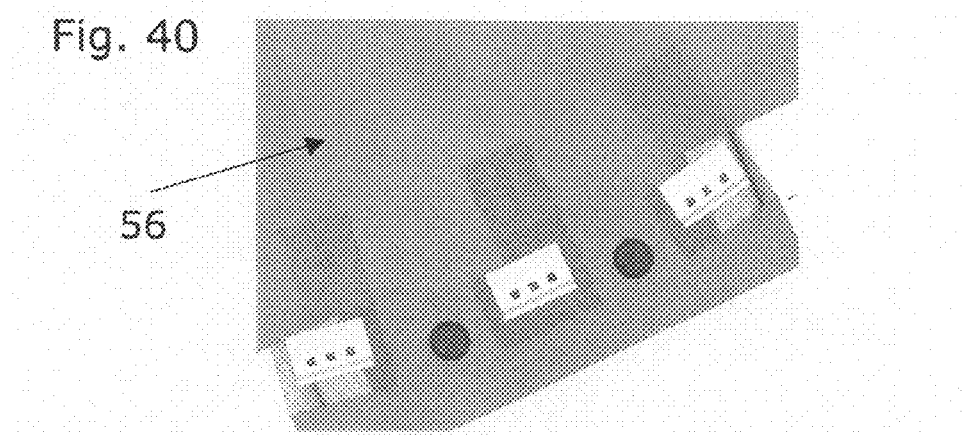
FIG. 40 shows the sensors in the storage for positioning of the storage carrousel, wherein the carrousel is in a third position.
Figure 41:
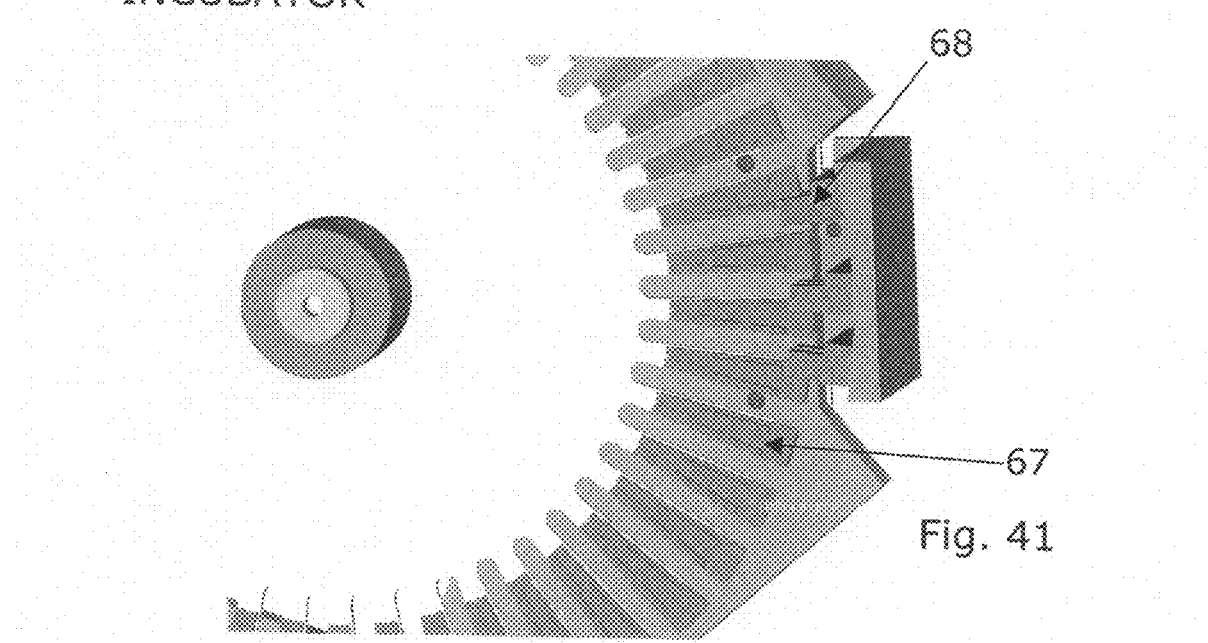
FIG. 41 shows an embodiment of an incubator disc comprising slots.

FIG. 40 illustrates why use of signal from 3 sensors is preferred:

It is possible to obtain a 360° error signal on A and B.

It is possible to obtain a power up error signal on B and C.

The above mentioned FIGS. 38-40, shows two possibilities of signals that could be erroneous interpreted as 360° or power-up signal. By preferably using three sensors it is possible to filter the erroneous signals and thus avoid misinterpretation of the position.

Stick Mover—Mover Module (MM)

Figure 59:
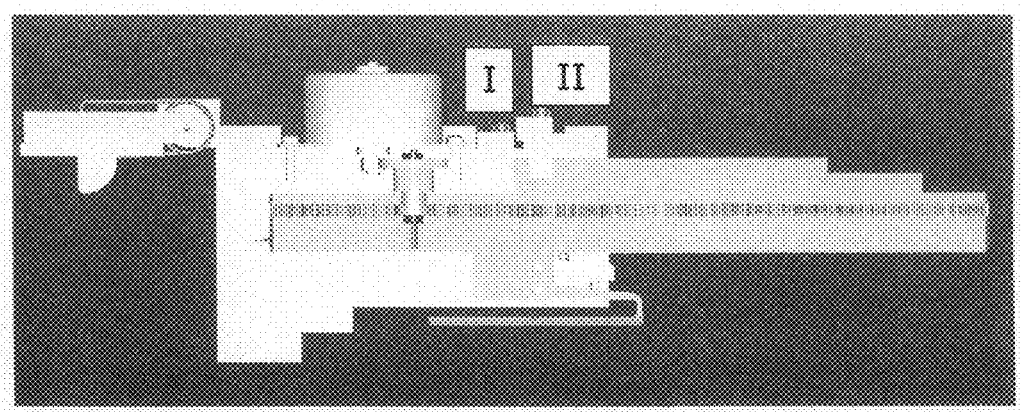
FIG. 59 shows the sensors in the stickmover device for positioning of the stickmover, wherein the stickmover is in a first position

FIG. 59 illustrates the starting position with detection blade behind sensor I. sensor I shows 0 and sensor II shows 1. Both the Storage Module carousel and Incubator Module carousel is able to rotate.

Figure 60:
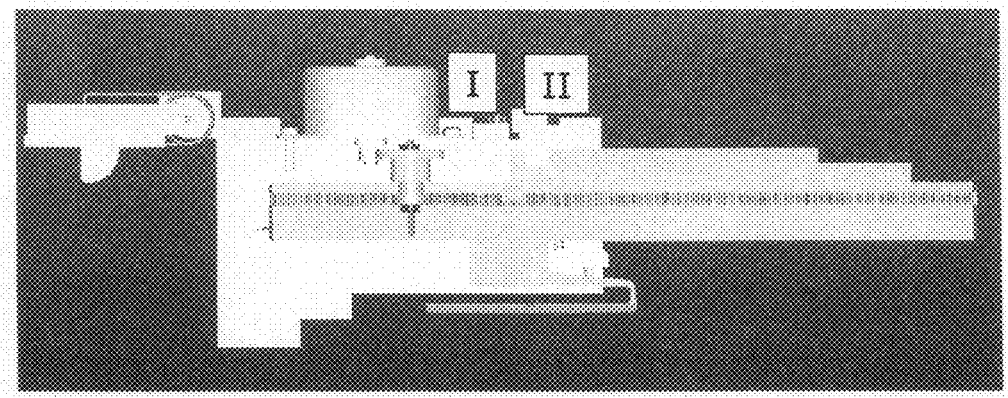
FIG. 60 shows the sensors in the stickmover device for positioning of the stickmover, wherein the stickmover is in a second position and transferring a stick of a first type.

FIG. 60 illustrates home position where home position preferably is registered by sensor I shows 1, (sensor II shows 1). Stop at the delivery position for Lateral Stick, Colour Stick and waste, is preferably registered by counting the steps from home position or from the position shown in FIG. 61.

The Incubator Module carousel may rotate until e.g. a Lateral Stick front passes the tunnel entrance. Preferably this position is identified by counting the number of steps from home position.

Figure 61:
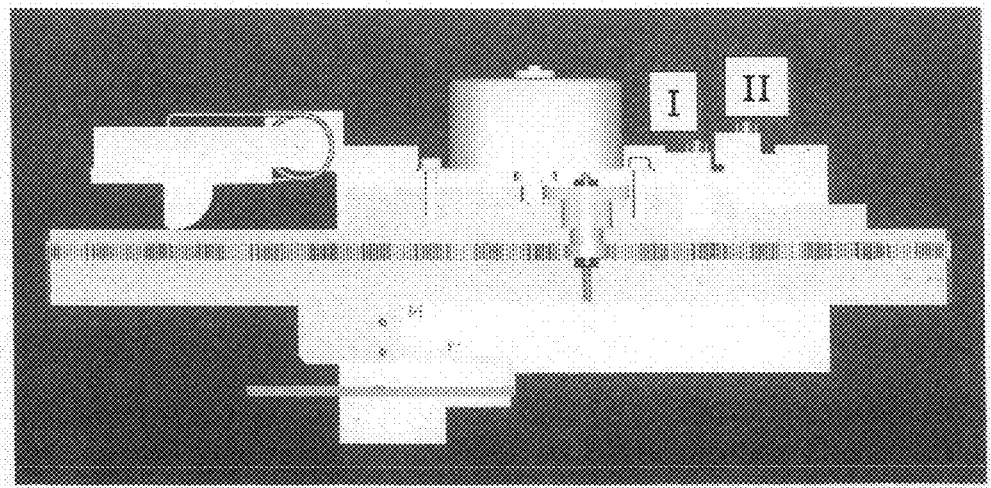
FIG. 61 shows the sensors in the stickmover device for positioning of the stickmover, wherein the stickmover is in a third position

FIG. 61 illustrates pawl inside tunnel, sensor I shows 1, sensor II shows 0. The Storage Module carousel may rotate.

Figure 62:
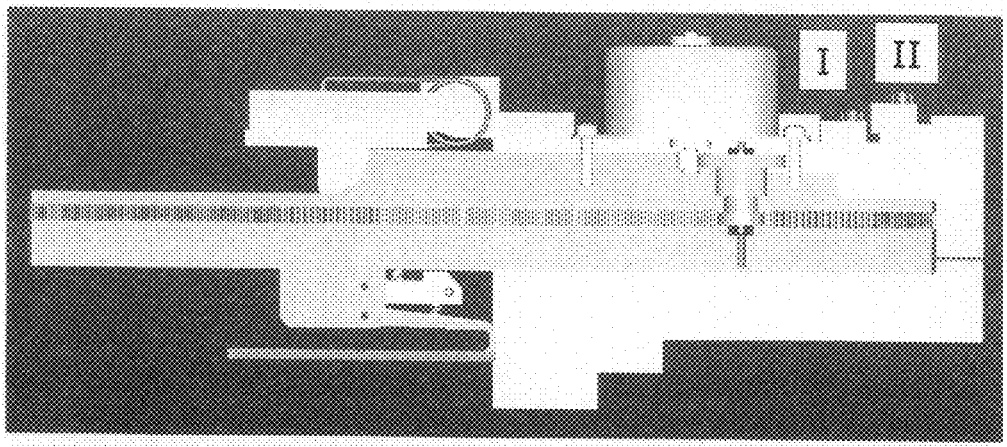
FIG. 62 shows the sensors in the stickmover device for positioning of the stickmover, wherein the stickmover is in a fourth position
Figure 63:
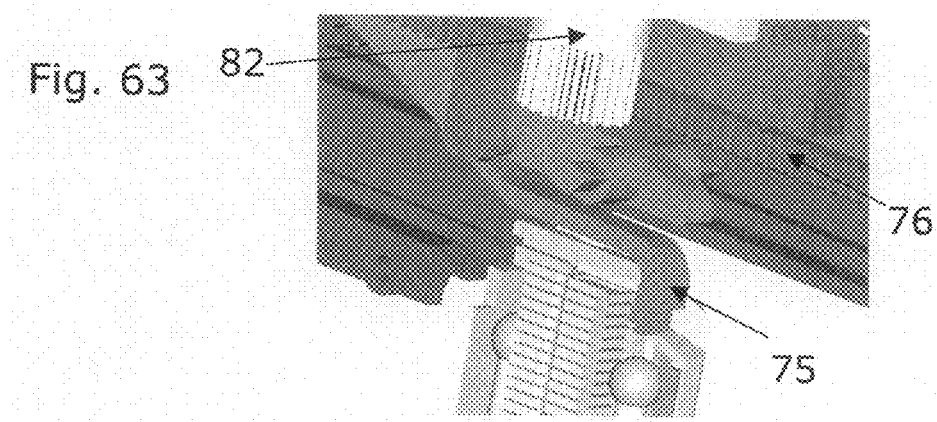
FIG. 63 shows the stickmover pawl catch a stick of a second type from the cartridge.
Figure 64:
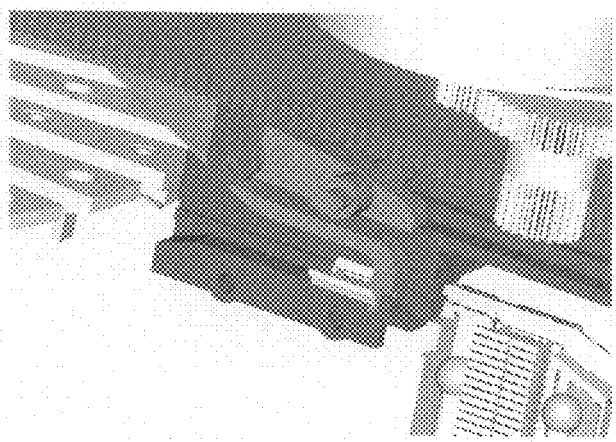
FIG. 64 shows the stickmover pawl transfer a stick through the stickmover channel towards the incubator.
Figure 65:
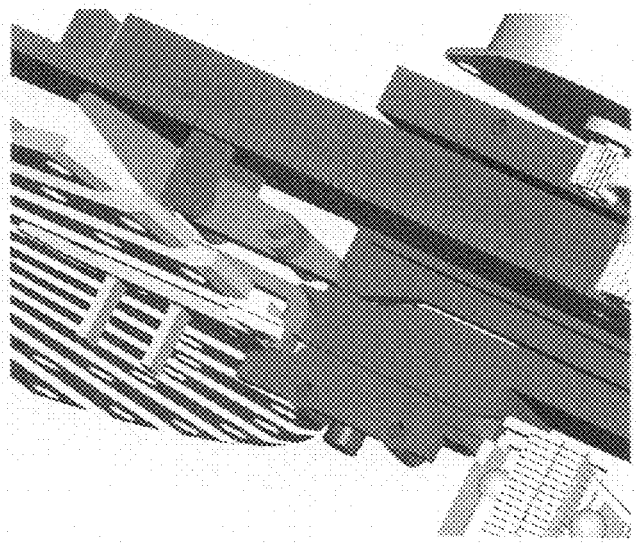
FIG. 65 shows the stickmover pawl transfer a stick into an incubator slot.
Figure 66:
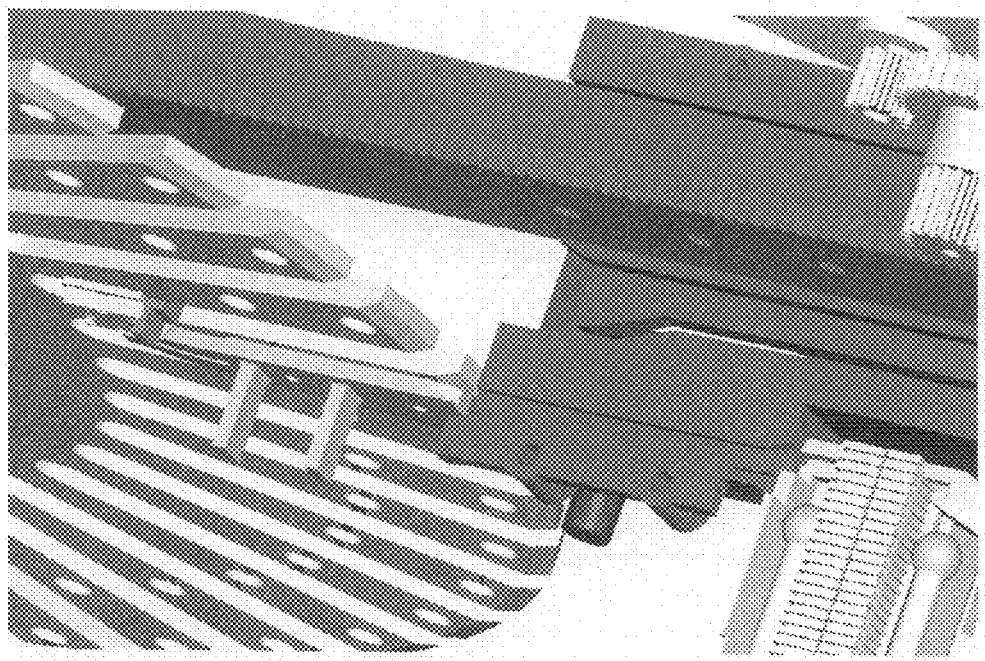
FIG. 66 shows the stickmover pawl transfer a stick into position in the incubator slot.
Figure 67:
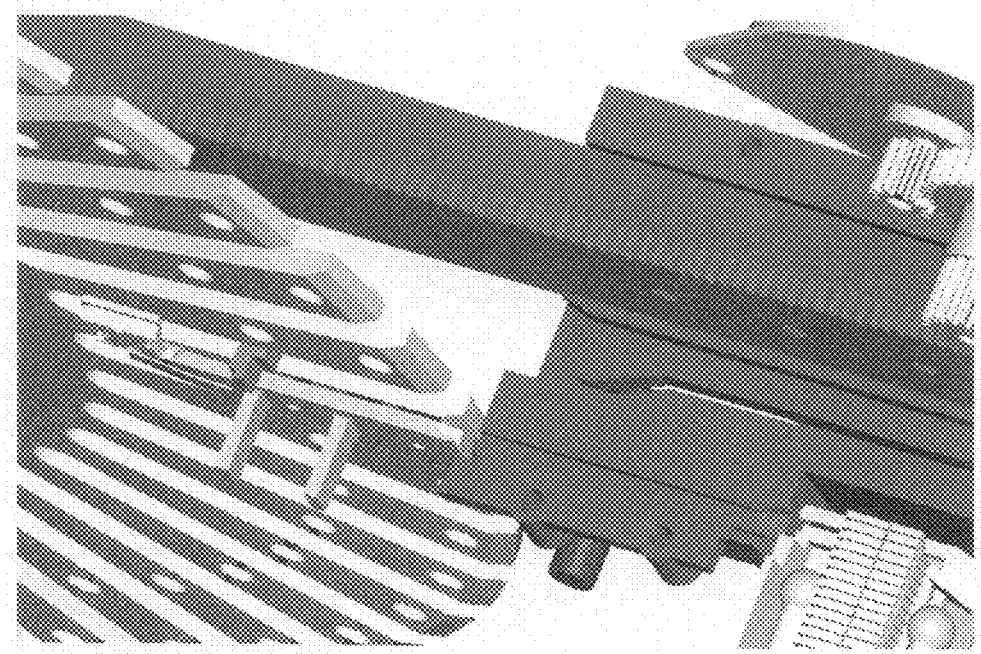
FIG. 67 shows the stickmover pawl retracts from the incubator slot.

FIG. 62 illustrates when the pawl is outside tunnel, sensor I shows 0, sensor II shows 0. The Storage Module carousel may rotate.

Dry: Power-up procedure

1: at detection blade; 0: no detection blade

| | | A first embodiment of Stick-mover feed-back | | | |
|---|---|---|---|---|---|
| Sensor I | Sensor II | Position of stick-mover pawl | Storage at tunnel ? | Incubator at tunnel ? | Action |
| 0 | 1 | Behind homesensor | True and false | True and false | 1. Initialize Storage. 2. Initilize incubator |
| 1 | 1 | Maybe in a cartridge | True | True | 1. stick-mover forward until in incubator. 2. Reverse stick-mover to home. 3. Init. Storage. 4. Init. Incubator. |
| | | | True | False** | 1. Init. Incubator. 2. stick-mover forward until in incubator. 3. Reverse stick-mover to home. 4. Init. Storage. |
| | | | False* | True and false** | A. 1. Move step by step towards the other sensor until this is not interrupted (max number of steps corresponding to the play between MM pawl and cartridge 2. Procedure as storage at tunnel true. If B0/C0 can not be obtained: B: 1. Reverse stick-mover to home. 2. Init incubator. 3. Init storage. |
| 1 | 0 | In tunnel | True | True | 1. Stick-mover forward until |

A first embodiment of Stick-mover feed-back

| Sensor I | Sensor II | Position of stick-mover pawl | Storage at tunnel? | Incubator at tunnel? | Action |
|---|---|---|---|---|---|
| | | | and false | | in incubator. 2. Reverse stick-mover to home. 3. Init. Storage. 4. Init. Incubator. |
| | | | True and false | False** | 1. Init. Incubator. 2. stick-mover forward until in incubator. 3. Reverse stick-mover to home. 4. Init. Storage.** |
| 0 | 0 | In incubator | True and false | True and false | 1. Stick-mover reverse to home. 2. Init. Storage. 3. Init. Incubator. |

*The stickmover pawl is too narrow to prevent a possibility of pawl in cartridge true and storage at tunnel false.
**Are the sticks able to prevent the situation incubator at tunnel false, and stick in tunnel and IM disc? If not, the same procedure A and B as for SM will be used.

A second embodiment of Stick-mover feed-back

| Sensor I | Sensor II | Position of stick-mover pawl | Storage "near right position"? | Incubator "near right position"? | Action |
|---|---|---|---|---|---|
| 1 | 0 | At home | True and false | True and false | 1. Initialise Storage. 2. Initialise incubator |
| 1 | 1 | Maybe in a cartridge | True | True | 1. Stick-mover forward until in incubator. 2. Reverse stick-mover to home. 3. Init. Storage. 4. Init. Incubator. |
| | | | True | False | 1. Init. Incubator. 2. Stick-mover forward until in incubator. 3. Reverse stick-mover to home. 4. Init. Storage. |
| | | | False | True and false | 1. Reverse stick-mover to home. 2. Init. Incubator. 3. Init. Storage. |
| 0 | 1 | In guide-way | True and false | True | 1. Stick-mover forward until in incubator. 2. Reverse stick-mover to home. 3. Init. Storage. 4. Init. Incubator. |
| | | | True and false | False | 1. Init. Incubator. 2. Stick-mover forward until in incubator. 3. Reverse stick-mover to home. 4. Init. Storage. |
| 0 | 0 | In incubator | True and false | True and false | 1. Stick-mover |

| | | A second embodiment of Stick-mover feed-back | | | |
|---|---|---|---|---|---|
| Sensor I | Sensor II | Position of stick-mover pawl | Storage "near right position"? | Incubator "near right position"? | Action |
| | | | | | reverse to home. 2. Init. Storage. 3. Init. Incubator. |

Strategy of position-sensing for turntables and stickmover.

The position-sensing enables the synchronisation of the virtual position in software (SW) and the physical position of turntable. The turntables are divided into positions, FIGS. 46 and 33, the incubator (FIG. 45) has stick slots and the storage has cartridge slots (FIG. 33). Each position is provided with a detection blade that interacts with a photo interrupter by interrupting the light beam. The flank of any detection blade is used for zero-setting the position counter. The flank is received a number of steps before the correct positioning, the so-called offset. The offset parameter can, if needed, be adjusted during assembly and test, to take up manufacturing tolerances.

The power-up and hard-restart strategy, described in the table "Strategy at power-up and hard restart" above, states the need of "near right position"-sensing. This is because the start-up sequence of synchronisation does not allow the rotation of turntables before it is ensured that the stick-mover is not engaged with a turntable. An additional photo interrupter is used together with the home-flank sensing photo interrupter. Each photo interrupter is positioned at a detection blade, their mutual distance being bigger than the mutual distance between the outer flanks of the two detection blades, see FIGS. 51-53. The condition that both light beams are not interrupted is therefore only at "near right position". The denomination "near right position" is used, as the precision of the position is much poorer than when a flank is used.

Figure 46:
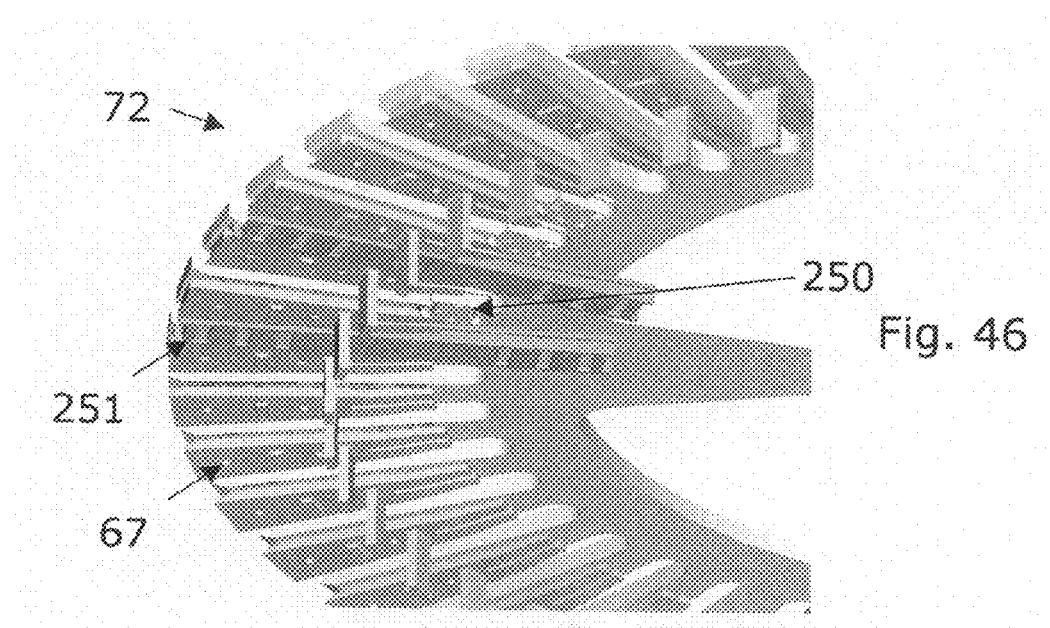
FIG. 46 shows an embodiment of an incubator disc comprising slots and sticks of the longer type.
Figure 47:
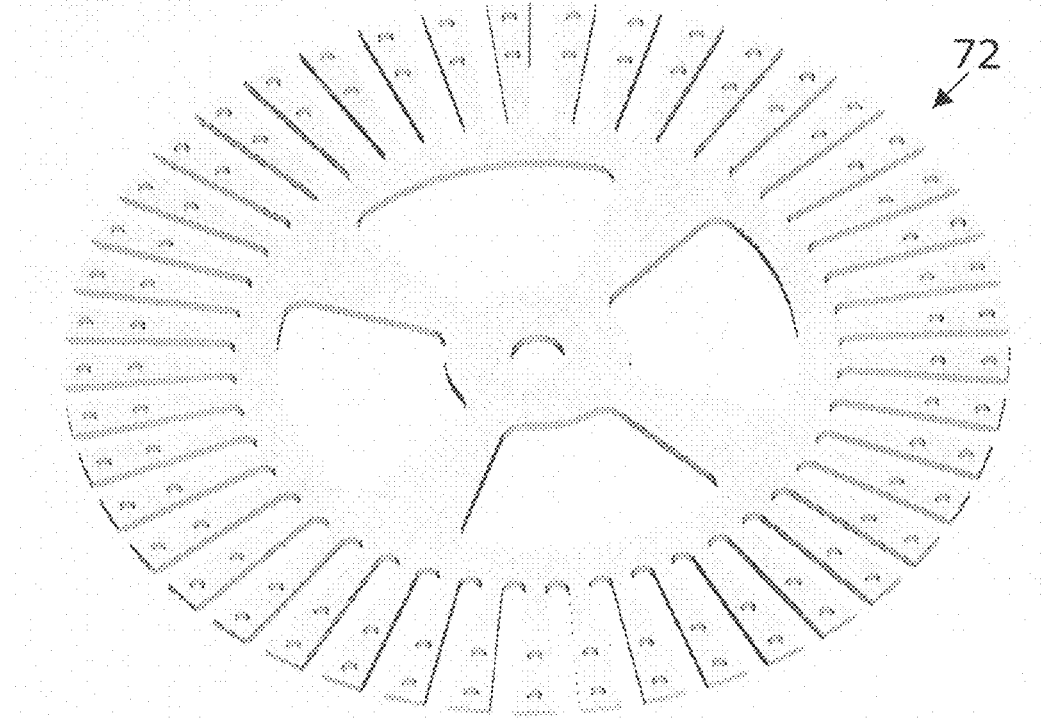
FIG. 47 shows an embodiment of an incubator disc.

The slots of the incubator are genderless/anonymous, see FIGS. 46-47. Any detection blade can be used for home.

The cartridge positions of the storage turntable are unique, see FIGS. 34-35, since there is calorimetric, lateral flow and desiccant cartridges.

A First Embodiment of the Reload Hatch
Function

The reload hatch, FIGS. 79-90 enables the renewal of cartridges by the operator. Together with the storage turntable it presents used cartridges to the operator who will renew the cartridge.

It enables secure and easy renewal of cartridges in co-operation with the storage turntable.

Furthermore it is preferably equipped with a gasket towards the storage insulation, a gasket internally between hatch and frame and also a gasket towards the top cabinet, in order to minimise entry of ambient air into the storage chamber.

The reload hatch also comprises sensing means in order to be able to secure that the hatch has been correctly closed and that it is in the closed position.

The reload hatch is equipped with a lock arrangement that closes the last 5-10 mm of the hatch movement. The lock can for example be a pawl driven by a linear stepmotor or a teethrack engaging with a gearwheel on a stepmotor or a dc motor, see FIGS. 83 and 84.
Function Sequence
Renewing Cartridge When the reload-hatch, shown in FIGS. 9 and 10, is open a keeper is presented through the hatch opening.

The operator pulls the used cartridge out of the keeper and inserts a new one. The reload-hatch is preventing the keeper to swing up during the insertion. This is done with the means of protrusions on the keeper that has entered a hook on the reload hatch flipper during the opening of the reload-hatch.

The leading in of the cartridge and prevention of accidental twisting of the keeper plunger may be assisted by arms that are swung up on both sides of the top of the keeper during the opening of the reload-hatch.

Closing Hatch and Locking Keeper in Turntable

The operator closes the reload-hatch that is preferably hinged in the bottom. The reload-hatch pushes the keeper that also swings up.

During the closing, a depressor arm 116 in the reload hatch, driven by a coulisse 117 (see FIGS. 79 and 80), pushes the cartridge further down into the keeper, see FIG. 100, against the force of the pusher spring 166 placed in the bottom of the keeper. This allows a protrusion 65 on the back of the cartridge to pass under the upper disc 56, illustrated in FIG. 37. When this has occurred the depressor arm 116 retracts, cartridge jumps up until the mentioned protrusion rests against the underside of the upper disc—making the chain of tolerances as short as possible, ensuring that each cartridge is leveled in respect to the stick-mover 7 and tunnel 78.

Figure 86:
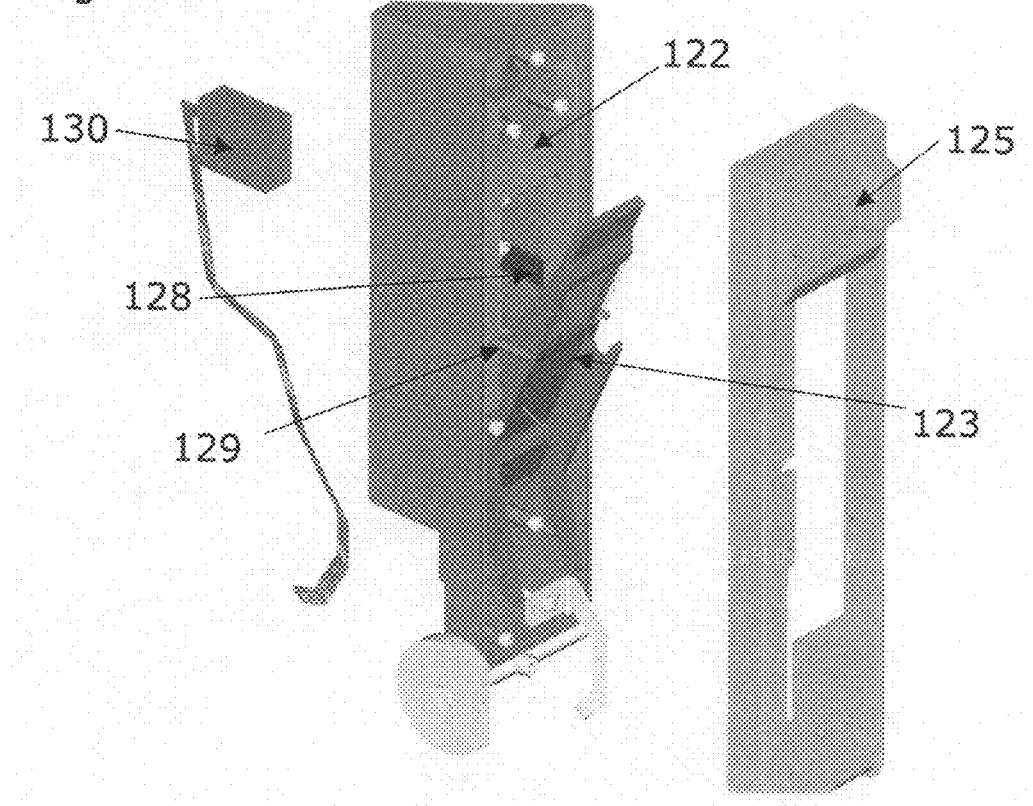
FIG. 86 shows exploded view showing the retractor, retractor springs, retractor pins and bar code reader.
Figure 87:
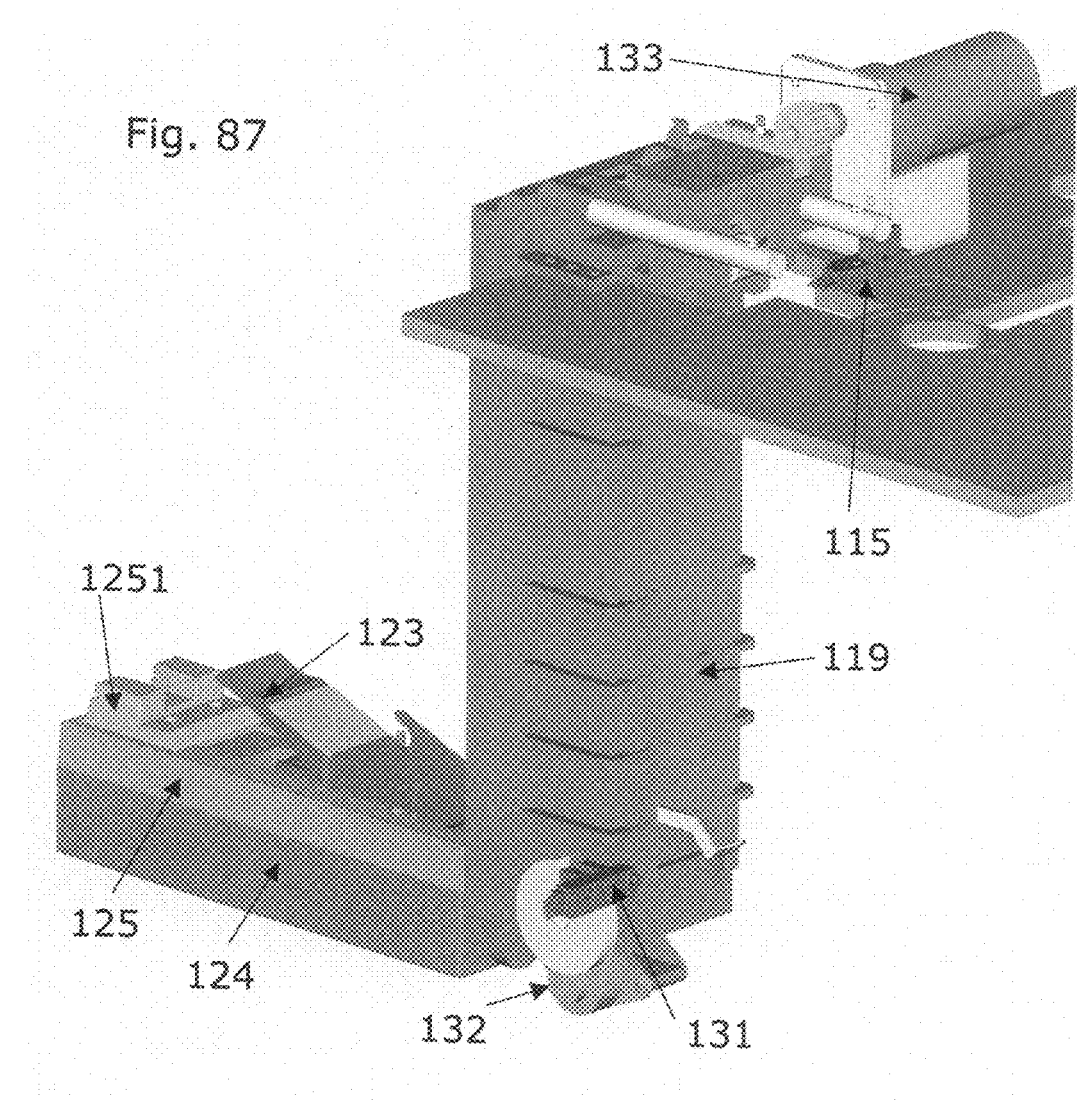
FIG. 87 shows the reload hatch mounted to the central beam wherein the hatch is opened. Furthermore the sensors for open and closed position is shown as well as the damper.

When the reload-hatch 124 is almost closed, the flipper 123, see FIG. 86, pushes the keeper in a swinging motion the rest of the way. The flippers motion is initiated by arms 1231 on the bottom of the flipper reaching the reload hatch frame, see FIG. 82, 85, 86. The flipper tilts and the top of the flipper pushes the keeper towards the center of the storage, see FIG. 86. The flipper 123 is then retracted from the keeper by the retractor arm 125 in the reload hatch 124. The retractor 125 is equipped with two pins 129. When the pins meet the reload hatch frame 119, the retractor 122 is pushed backwards against its springs 1221. The flipper 123 follow the retractor away from the storage. This leaves clearance between the reload-hatch flipper and keeper 1601, 2±1 mm. The backside of the cartridge rests against the edge of the cut out in the upper disc—keeping the position tolerances low. A photointerrupter sense that the reload-hatch is closed and the turntable is allowed to rotate.

Figure 82:
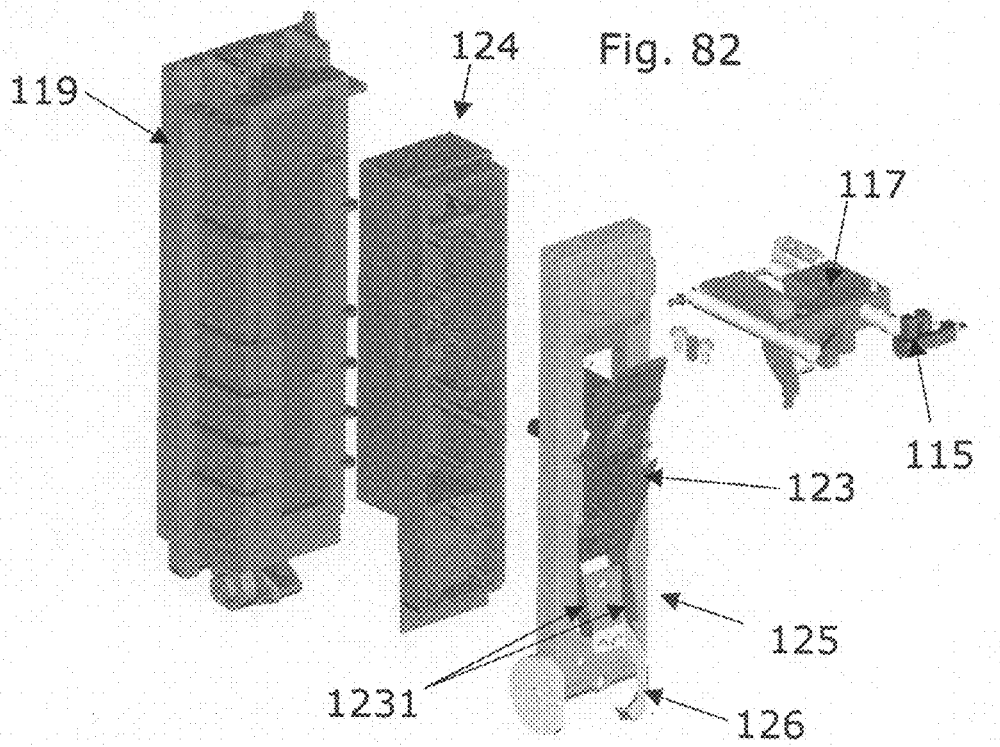
FIG. 82 shows an exploded view of the reload hatch from a different angle.
Figure 83:
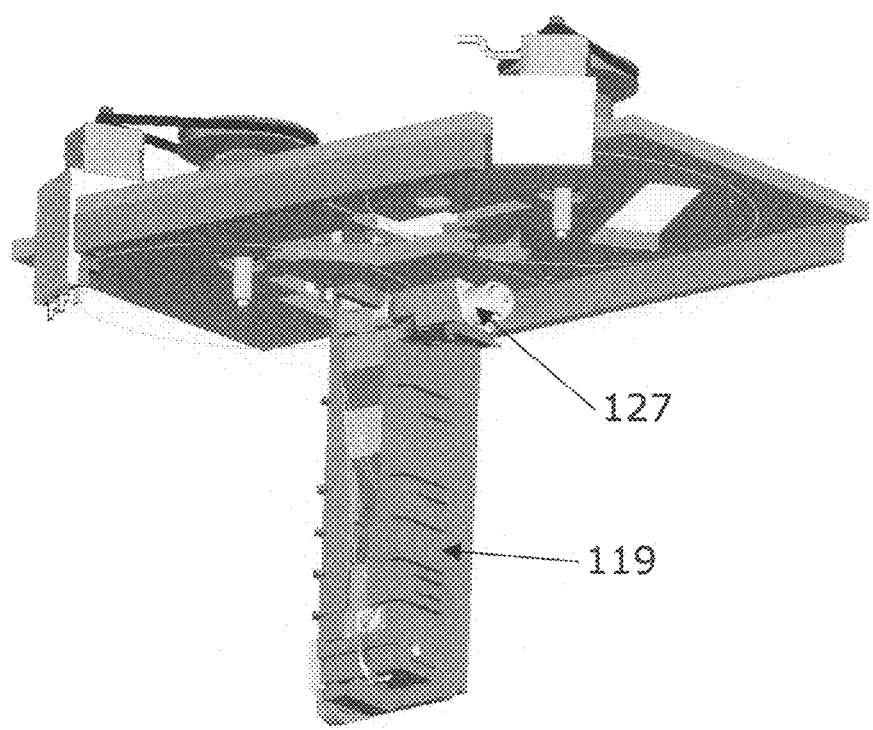
FIG. 83 shows the reload hatch mounted to the central beam.
Figure 84:
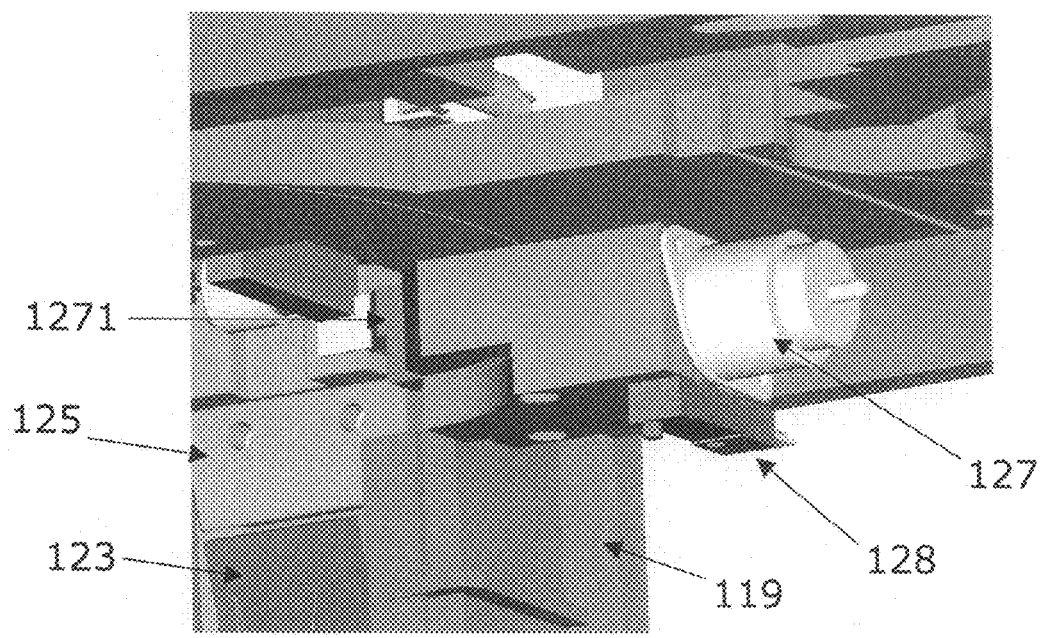
FIG. 84 shows details of the driving assembly for the closing hatch.
Figure 85:
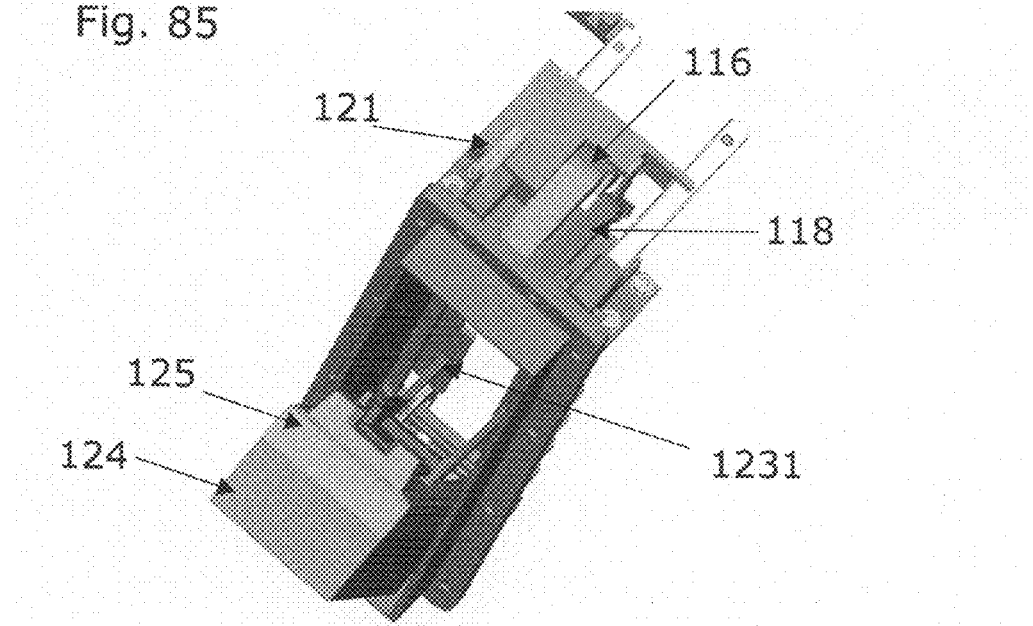
FIG. 85 shows the interaction of the flipper arms interacting with the reload hatch frame.

The arm 126 shown in FIG. 82 is preferably for the purpose of leading wires in a safe way in the embodiment wherein the bar code reader is mounted in the hatch.

When the reload-hatch is almost closed, the spring loaded keeper-pawl pulls the keeper the rest of the way. This leaves a clearance between hatch and keeper, 2±1 mm. The backside of the cartridge rests against the edge of the cut-out in the upper disc—keeping the position tolerances low.

Finally a pawl 136 locks the reload-hatch and a gasket seals against the reload-hatch casing. The part of the retractor 125 wherein the pawl 136 interacts is preferably made of metal as shown in FIG. 90.

During the closing the reload-hatch that pushed the arm, that released the keeper pawl when the reload-hatch was opened, is returned to normal position to allow the pawl 136 to lock the keeper.

Preferably a photointerrupter sense that the reload-hatch is closed and the turntable is allowed to rotate.

Figure 117:
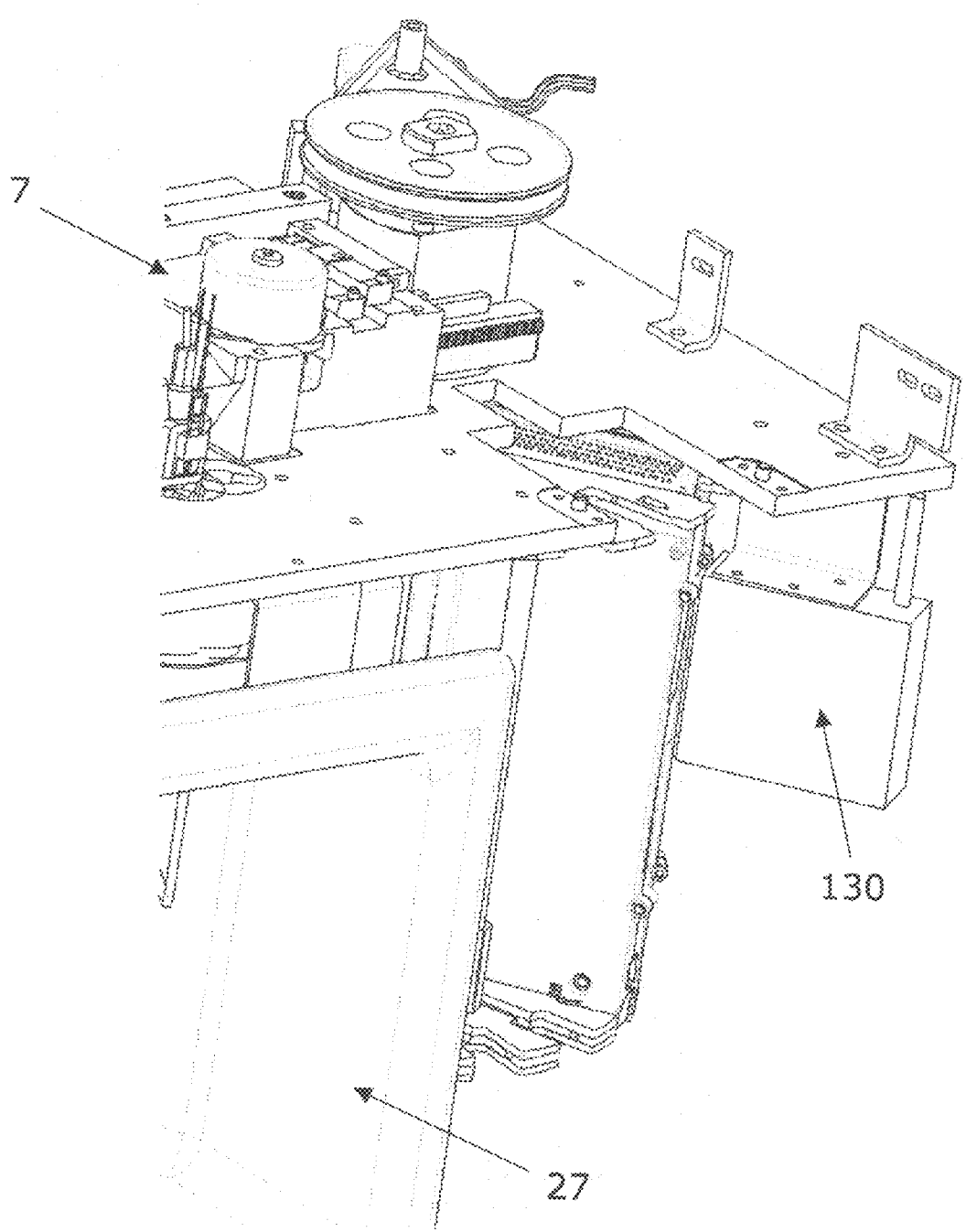
FIG. 117 shows an embodiment of placement of the bar code reader inside the storage.
Figure 118:
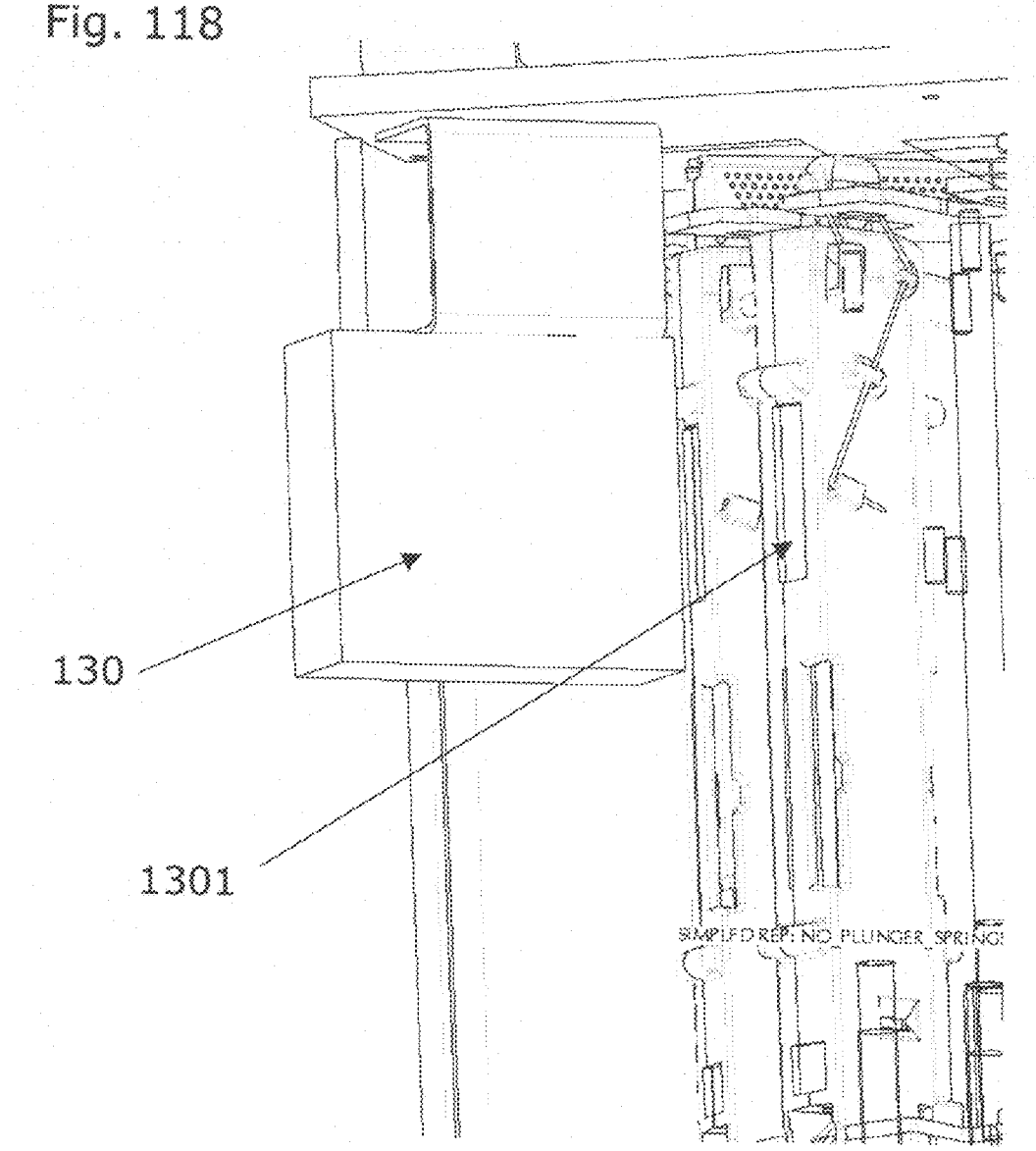
FIG. 118 shows the barcode reader and a slit in cartridge keepers for enabling reading of the bar code labels on the cartridges.

Furthermore the hatch may comprise a bar code reader 130 for reading bar codes on cartridges. However and preferably the bar code reader is mounted inside the storage in order to protect it from the outer environment. The bar code reader may be of laser type or preferably of a CCD type wherein the whole bar code is read and analyses in a computer system. Thus the barcode may preferably be positioned inside the storage in a position so it is able to read bar codes on cartridges, see FIGS. 117 and 118.

Preferably the cartridge keeper comprises a hole or slit 1301 so that a bar code reader 130 is able to read the bar code on a cartridge when the keeper is rotated in the storage carrousel.

Opening Reload-Hatch and Releasing Keeper

The AI opens the Reload-hatch as it releases a pawl 136 or other means 1271 locking the reload-hatch in the closed position. The reload-hatch contains a release arm 118, FIG. 79, driven by a coulisse 117 that actuates the keeper spring 121, releasing this from its position in the storage upper disc.

The pawl is actuated by a dc-motor 133 equipped with a gear wheel. To release the pawl the motor is energized to turn an eccentric pushing the spring loaded pawl. The motor is stopped when it returns to home sensed by a detection blade 115 on the eccentric and a photointerruper.

The reload-hatch interacts with a spring-loaded arm 118 that actuates the keeper pawl 136, releasing the keeper when the AI opens the hatch.

When the keeper is released, it swings out and rests against the partly opened reload-hatch. The operator swings down the hatch, while the keeper follows its motion, until the hatch rests against a stop in a horizontal position. The hatch can be equipped with a damper 132 to dampen its opening motion.

During the motion the keeper and hatch are locked together and a gate is swung up at the top of the keeper as previously mentioned.

To facilitate opening of the reload-hatch during repair and service the pawl can be released by sticking a small rod through a hole.

Control Strategy.

HW integrates to two photointerrupters and one dc-motor. The motor is used unidirectional e.g. no shift of polarity needed.

One photointerrupter monitors if the reload-hatch is closed. The light beam is interrupted when the reload-hatch is closed. The storage turntable is allowed to rotate when the reload-hatch is closed.

To open the reload-hatch the dc-motor 133 is energized. The motor is turned off when it returns to home sensed by a detection plate and a photointerrupter. At home the light beam is interrupted by the detection plate.

A Second Embodiment of the Reload Hatch

A second embodiment of the locking mechanism for the reload hatch comprises a motor, two sensors, a teethrack 134 and a pawl mounted on the coulisse, and a solenoide 135, see FIGS. 87-90.

Function Close:

The user preferably closes the hatch to a position app. 15 mm before closed position. At this position a pawl 136 mounted to the coulisse engages with the hatch. At the same position sensor 131 is broken and the motor 133 moves the coulisse 117. The hatch closes. When in closed position, sensor 115 is broken. This activates the solenoide 135 that locks the hatch.

Function Open:

The solenoide 135 is activated, unlocking the hatch. The motor 133 moves the coulisse with the pawl resulting in an opening of the hatch. When the pawl 136 meets the reload hatch frame 119, it swings away from the hatch. The hatch is now free to fall to its fully open position by gravity. Preferably a damper 132 ensures a controlled motion of the hatch.

The damper is connected to a gearwheel 132 which is connected to the hatch 124. A sensor 131 senses when the hatch is being closed and actuates the motor 133 for closing of the hatch.

Stickmover

Function

The stick-mover 7 transfers the stick from the storage to the incubator disc, see FIG. 54.

Applied Solution

The stick-mover shown in FIGS. 54, 63-67 and 69-71 consists of:

A pawl 75 that manipulates the stick, the pawl is preferably guided in a coulisse 741 that lifts the pawl 75 over the cartridges when the stick-mover is reversed. The pawl is hinged and forced down by a spring 83. A linear guided slide 751 on which the pawl is hinged. The slide is provided with a teeth rack 76 and detection blades 77 for position sensing. A gearwheel 82 that drives the slide. Preferably a stepper motor 74 with a pinion drives the gearwheel with preferably a 3.33:1-ratio. Two photo-interrupters sensing the detection blades on the slide. A housing providing linear guiding of slide, coulisse guiding of the pawl, support of photo-interrupters and a tunnel 78 in which the stick is guided between storage and incubator.

The stick-mover is preferably also equipped with a hatch 79 to reduce airflow between incubator and storage chamber.

Function Sequence

One embodiment of the function sequence is illustrated in FIGS. 63-67.

The pawl rests in the reversed position, the Home-position. Thereafter the pawl is lowered.

The cartridges on the turntable can pass by the tip of the pawl, as it is positioned close to the center of the turntable.

When the desired cartridge is positioned under the stick-mover, aligned with the stick tunnel, the motor is activated to advance the slide. The slide forces the pawl and the pawl lifter to move forward. The pawl lifter 81 enters the lower track of the coulisse in the stickmover house.

The pawl meets the ramp in the cartridge on the top and back of the cartridge. The ramp forces the tip of the pawl to flex upwards against the spring force, which eliminates misalignments and levels the tip of the pawl in relation to the stick, see FIG. 71.

The tip of the pawl engages the end wall of the stick. The end wall of the stick has a shelf-like protrusion matching a cutout in the profile of the tip of the pawl 75, preventing the pawl to slip off the stick.

The stick is pushed out of the cartridge, passes over the gap between the cartridge and tunnel (2±1 mm) and enters the tunnel 78, assisted by leading-in chambers.

When stick and pawl have entered the tunnel the storage turntable is allowed to turn to present next cartridge. The stick-mover may be stopped in this position to await the indexing of the incubator turntable.

The slide is advanced further on and the pawl leaves the coulisse.

The stick passes the gap and into the slot of the incubator and advanced to the intended position. The new stick pushes used stick out of the slot. The used stick falls into the waste container.

The slide is reversed and the tip of the pawl slides of the stick.

The pawl enters the coulisse in its reverse motion and the pawl lifter is being guided into the upper track by the track-changer 84, which is preferably made of a spring wire. The pawl is lifted and can now pass over the cartridge, thus allowing the turntable to rotate.

The slide is returned to home where the pawl is lowered as the upper and lower tracks are connected at this position. The motor is turned off and the cycle is complete.

Figure 68:
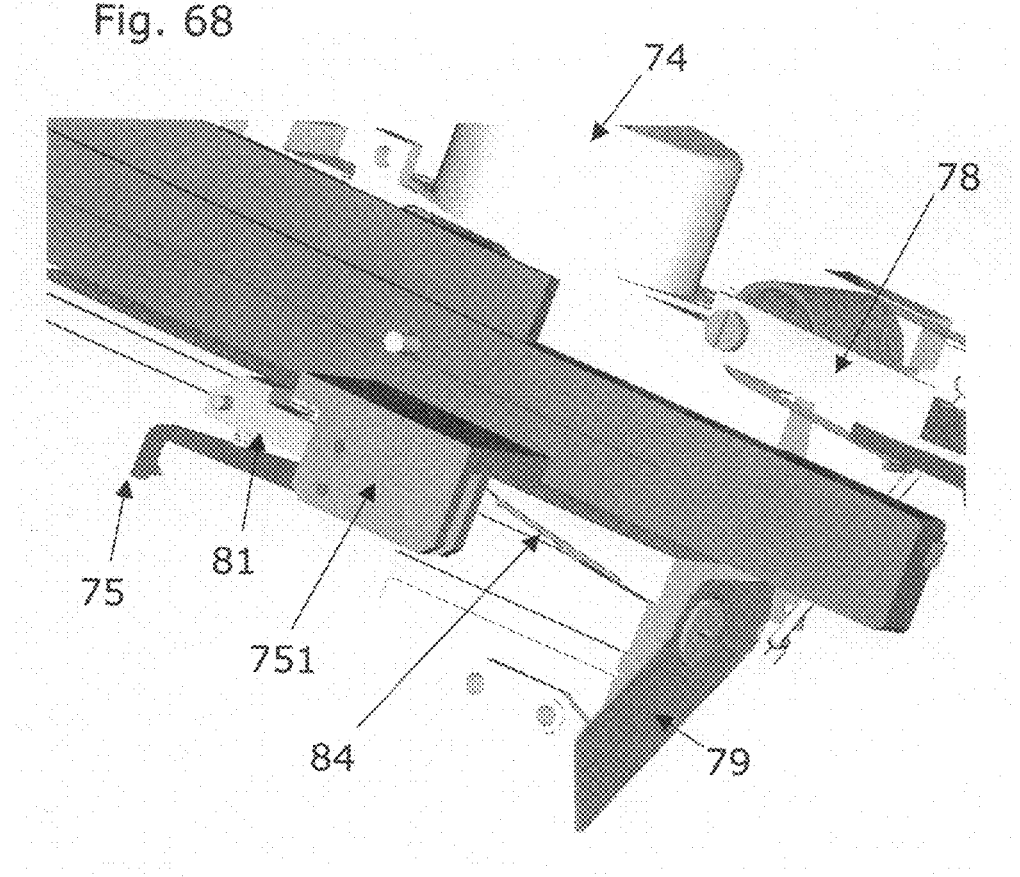
FIG. 68 shows the stickmover assembly and the guiding tracks comprising the flexible track changer for directing the stickmover pawl to a different track upon retraction.
Figure 69:
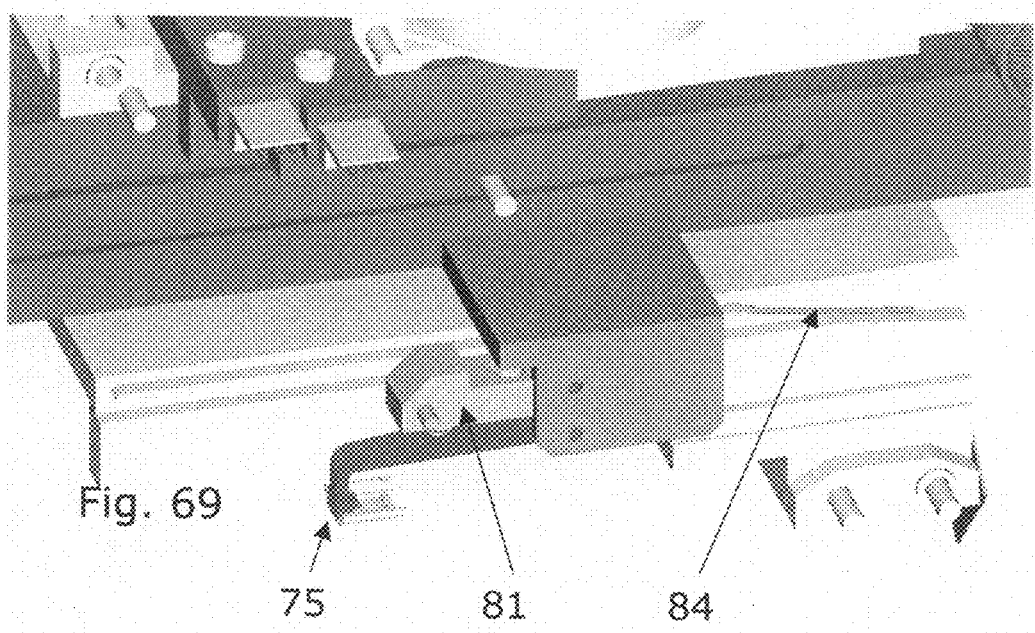
FIG. 69 shows the stickmover assembly catching a stick of a second type.

In FIG. 68 is shown an embodiment wherein the downward biasing of the pawl 75 and pawl lifter 81 is achieved with two small springs.

The motor is driven in ½-step mode to enhance the resolution. Micro step modes are preferably not used as PM-stepper motors don't perform precisely in these modes.

At standstill in the home position the motor is preferably turned off to prevent heat generation.

At other points of standstill the current is preferably reduced to about 50%, which may reduce the heat generation with up to 75%. The synchronism is maintained.

When advancing from home position a digital flank is received from the sensing of the home detection blade. The flank is used for zero-setting the position counter. The slack of the drive train is taken up as advancing begins and the position counted is only precise when mowing forward. When reversed the slack shift direction, meaning a longer virtual movement is necessary to return to home.

In a second embodiment the stickmover system may comprise a system for securing and checking the transfer of sticks from storage to incubator and the precise positioning of the sticks in the incubator.

Transfer from storage to incubator: An optical reflection sensor, of standard type, placed underneath the passing stick in the stickmover tunnel. When the stick, drawn by the stickmover pawl, passes the sensor, the emitted signal from the sensor will be reflected by the stick and received by the sensor. If the pawl does not draw/carry a stick, no signal will be reflected. Corrective actions can then be made by the SW (E.g.: The error will most likely be caused by a malfunctioning cartridge. A shift to another cartridge containing the same sticktype will result in a successful transfer).

| Data and specifications | | |
|---|---|---|
| Step per rev. | 48 PPR | 7.5 PM-stepper motor |
| Microstep | 2 µstep/step | Using ½-step mode |
| Needed resolution | 0.098 mm | |
| Available dL per rev. | 9.42 mm/rev. | |
| PitchDiameter toothwheel | 10 mm | Engaging linear tooth rack on |
| Perimeter toothwheel | 31.4 mm/rev. | stick-mover slide |
| Neded i | 3.33 | |
| Z motorpinion | 12 | |
| Z gearwheel | 40.00 | Bigger wheel on above mentioned tooth wheel |

Incubator Module

Figure 51:
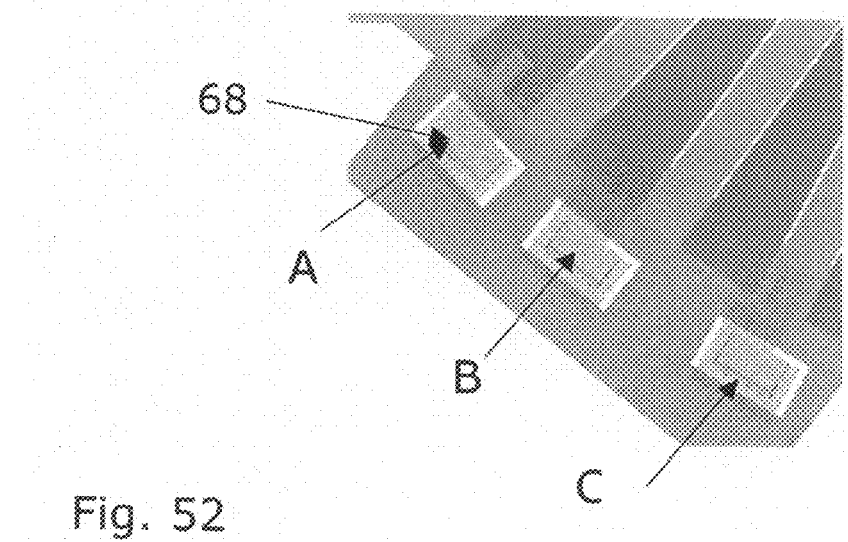
FIG. 51 shows the sensors in the incubator for positioning of the incubator disc, wherein the disc is in a first position.
Figure 52:
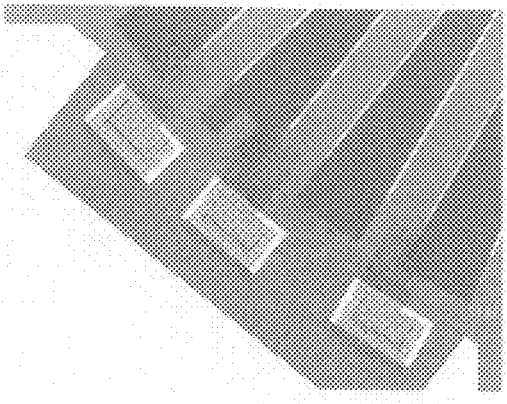
FIG. 52 shows the sensors in the incubator for positioning of the incubator disc, wherein the disc is in a second position.
Figure 53:
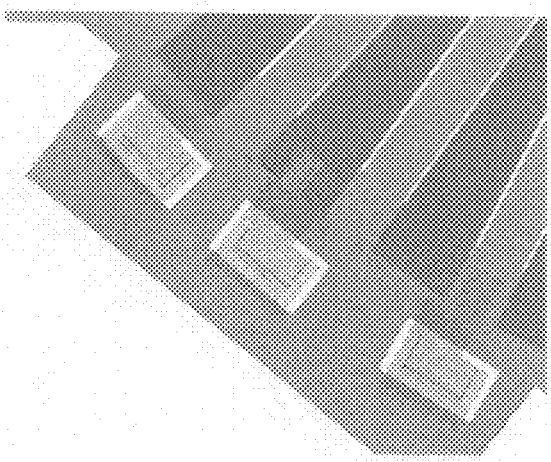
FIG. 53 shows the sensors in the incubator for positioning of the incubator disc, wherein the disc is in a third position.

Three sensors 68 are positioned so that the sensors A and B always see the same signal, see FIGS. 51-53, except when the revolution detection blade passes since the detection blade has a slit, shown in FIG. 52.

Registration of 360°: 360° at registration of A0 and B1 (0: not covered, 1: covered).

B. Error Possibility:

1. A is mounted so that 0 occurs at A before B, when a normal detection blade is left out.
2. B is mounted so that 1 occurs at B before A when a normal detection blade arrives. Both errors are sorted out by registering A0 and B1 two times during a periphery interval at e.g. 1.5 mm corresponding to 15¼ step.

A second embodiment for obtaining a pr revolution signal is using a hall-effect sensor placed at the periphery of the incubator and a magnet placed at the disc.

Registration for tunnel positioning during operation: Sensor C is used to count number of steps from interrupt to tunnel positioning. (C is also used for initialisation. A is preferably only used for giving a 360° signal.)

Start after e.g. power up: Is registered if both B and C shows 0. If they show 0 the Incubator Module carrousel is in tunnel position.

Mechanical Part

The main mechanical part is an incubator disc 72 comprising a number of slots. The preferred embodiment of an incubator disc is shown in FIG. 47.

Function

The incubator disc is necessary for positioning, keeping and guiding the sticks in place during the loading, dosing, incubation, reading and removal steps of the analysis process.

Number of Incubator Slots

The number of slots is preferably 45, but this number is governed by the incubation time and the required throughput of sticks. These slots may be divided into the different sectors as described below:

Slots 1 through 4: Is preferably used for temperature conditioning of the sticks and for physical clearance for the stickmover. Between these positions the temperature of the sticks is raised from 20° C. to app 25° C. This may be achieved by using a forced flow of the 25° C. incubator chamber air.

Slot 5: is preferably for dosage of milk onto the test sticks.

Slots 5 through 43: is preferably for incubation of the sticks. The indexing interval is preferably 8 seconds, as each sample needs to be taken from ST preferably every 24 seconds, in average, and 3 tests, in average, is needed from each sample. The specified time of incubation is preferably 300 seconds and the number of slots of incubation is preferably 38.

Slot 43: is preferably for the reader.

Slot 44, 45 is preferably allocated for physical clearance between reader and stick-mover.

Positioning of Stick in Incubator

Position of stick in incubator: Two or more reflective sensors above or under the incubator disc, will receive reflected signals if the sticks are positioned correctly. This can be obtained by utilising the pattern of free space and reflective and non-reflective materials in the stick, that is established by the stick and around the stick. If the stick is not positioned correctly it will not be used for analysis, and another stick can be transferred for this analysis.

Applied Solution

The incubator disc may be made of 3 mm stainless steel. The manufacturing of the disc can be done by a combination of laser cutting and punching. The disc has preferably 45 places, which can be used for both lateral and colorimetric sticks.

To ensure fixing of the sticks, an injection moulded incubator slot 67 has been mounted for each incubation place, this is shown in FIGS. 44-46.

Figure 48:
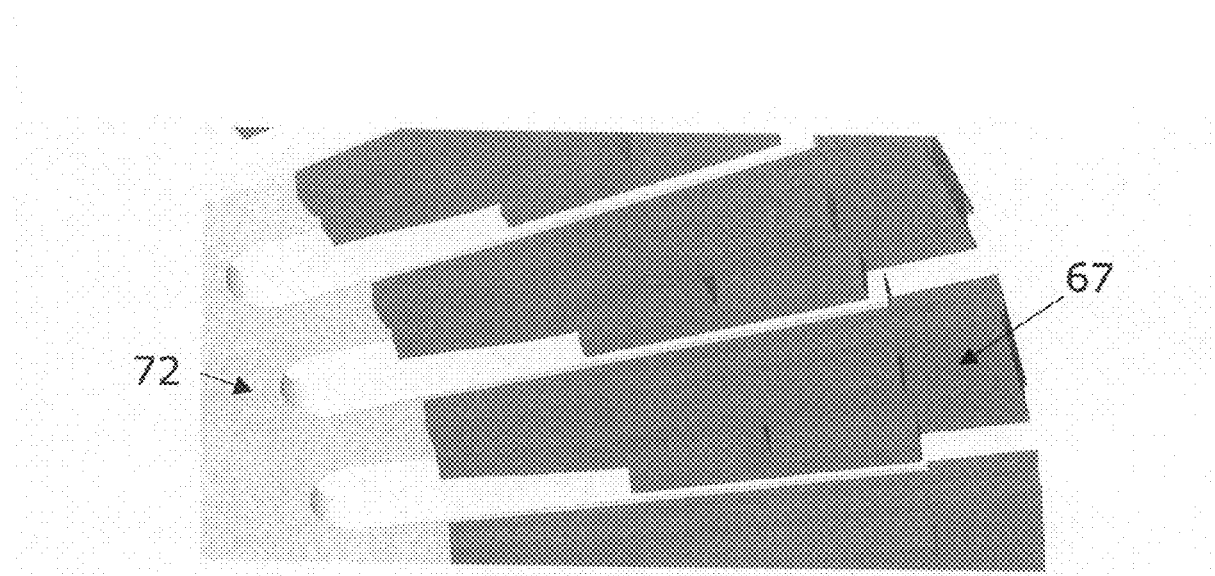
FIG. 48 shows guiding slots mounted to the incubator disc.

When the stick is transferred from storage, the upper side of the stick meets the bottom of the incubator disc. In another embodiment shown in FIGS. 48-49 the upper side of the stick meets a surface 71 in the slot. This has the advantage that the stick will not adhere to the incubator carrousel when pushed into the free fall into the waste container.

Furthermore this embodiment gives the additional advantage that the sensors can be placed in the same manner as in the storage (see drives for storage and incubator).

The incubator slot has lead-in 70 to obtain tolerances, see FIGS. 43-45. The slot also functions so as to guide the wings of the sticks when the sticks are transferred onto the slot.

Furthermore the slot has been supplied with a built-in lock to maintain the stick, when the disc is rotating or the apparatus is influenced by external conditions.

Simultaneously, the lock makes sure that the stick is positioned precisely against the disc, when loading or unloading is taking place. The stick should preferably be positioned in substantially vertical position in order to facilitate reading the result developed on the stick.

The incubator slot may be fixed to the disc 72, shown in FIG. 46, by means of thread shaping screws. Furthermore, in a second embodiment, the incubator slot has detection blades for detection of position. An incubator slot has two detection blades, where the other one can be used for one per revolution sensor.

Figure 49:
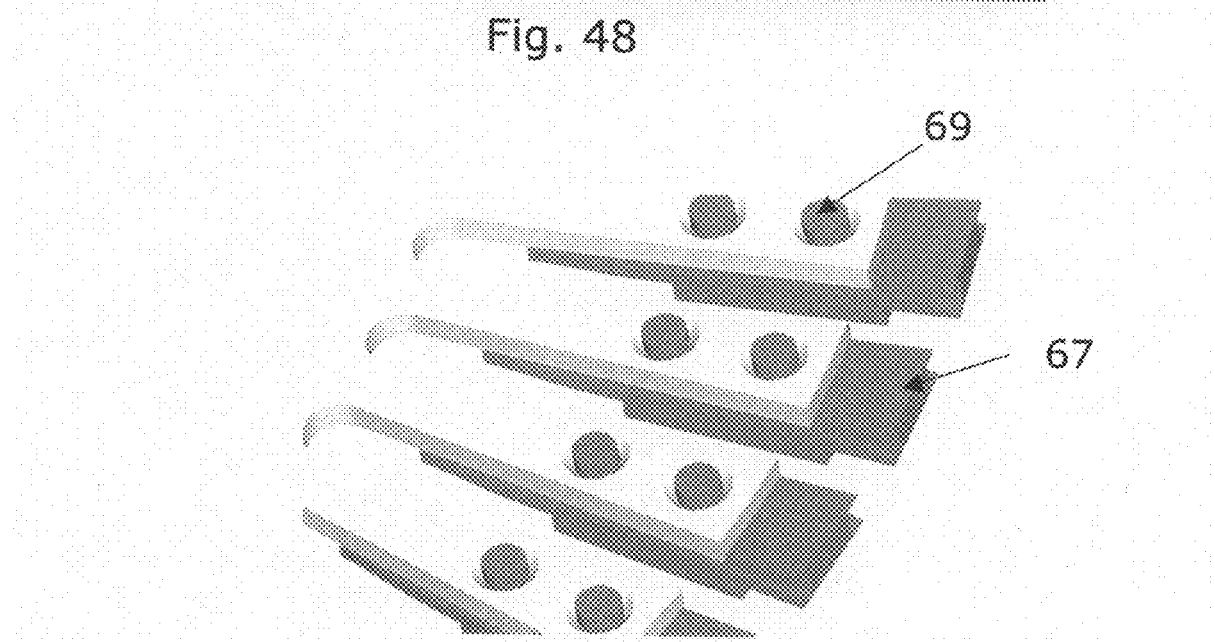
FIG. 49 shows fastening means for the guiding slots.

A preferred embodiment for fastening an incubator slot is shown in FIG. 49 wherein the small towers 69 is heated on the slots, melting the plastic, and in this way locking the slots to the carrousel disc, see FIG. 49.

| Preferred Data and specifications | |
|---|---|
| Disc: | 3 mm stainless AISI 304. |
| | Manufactured by laser cutting and stamping. |
| Weight: | 640 g. |
| Slot: | Injection moulded in POM. |
| Volume of slot: | 550 mm$^3$ |
| Weight: | 0.77 g. |

Dosage System
Dosage Component

Figure 72:
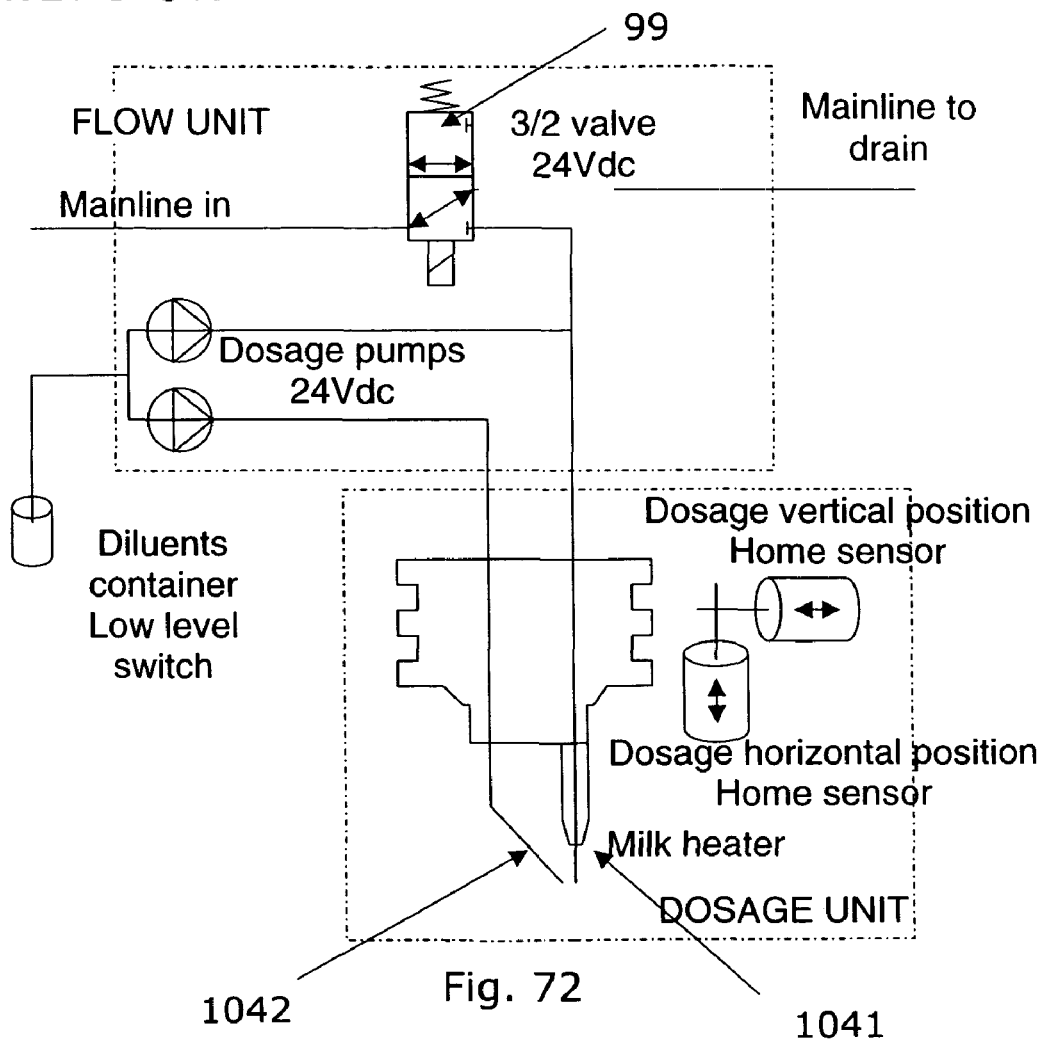
FIG. 72 shows a schematic diagram of the wet-system in the analysis apparatus

A first embodiment of the dosage flow system is illustrated in FIG. 72, and preferably comprises a dosage unit, dosage pumps 95, 96 apportioning different volumes, a drain funnel, a valve and pipes.

Figure 73:
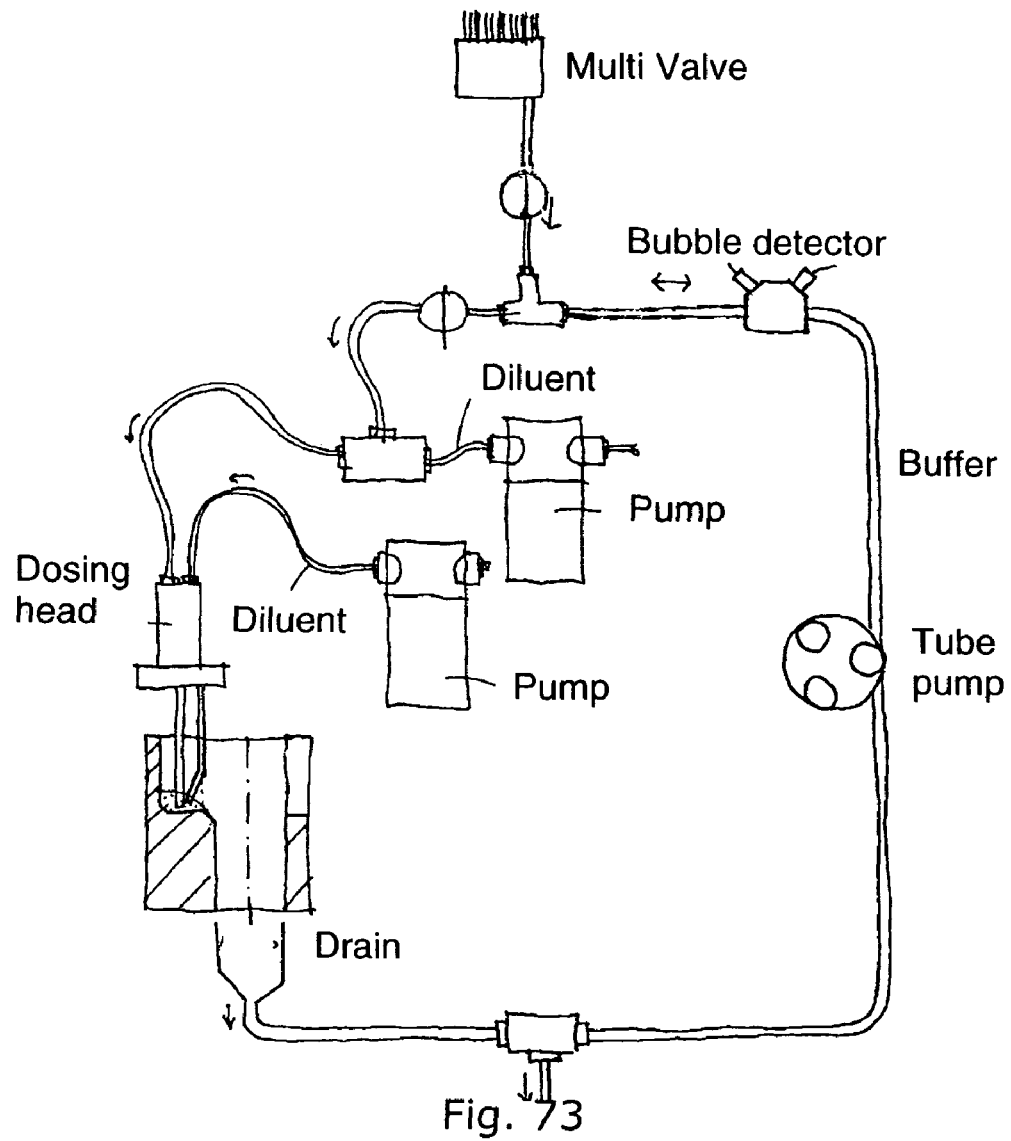
FIG. 73 shows a second embodiment of a wet-system in the analysis instrument comprising bubble detectors.

A second embodiment of the Dosage flow system is illustrated in FIG. 73, and preferably comprises a dosing head 105, dosage pumps 95, 96, a tube pump, a bubble detector, a drain, a multivalve guiding the samples from the milking points to the analyser instrument, valves and pipes. The multivalve and the tube pump can be part of the analyser or part of an external system.

The milk sample is apportioned from the sample transport system to the main line, preferably by a pump placed in the sample transport system. The sample is pumped to the mainline drain, in order to clean the mainline for the previous sample. The valve is switched to the pipe going to the dosage unit. The dosage line is flushed with the sample, with the dosage needle 1041 placed above the drain funnel. The dosage head 105 is then moved to the narrow slit in the drain funnel, the position shown in FIG. 73. The diluent line dosage pump (shown below the sample dosage pump on FIG. 72) is activated. This flushes diluent out in the drain funnel slit, washing the outside of the dosage needle. The dosage unit is slowly moved out of the slit. The slow movement ensures that all the diluent is drawn off the needles. The dosage unit can now be moved to the dosage position above the stick. The sample dosage pump is now activated. Diluent pushes the milk sample out of the dosage needle.

FIG. 74 shows the dosing of milk onto a test stick. The milk is applied from approximately 1-3 mm height by pushing the sample with the dosage pump. To apply the droplet attached to the dosing needle, the dosing needle is lowered in order to contact the test stick. By doing this, the droplet is drawn of the needle. In this way the needed precision of the sample volume applied to the stick is obtained.

In FIG. 75 the pump/valve arrangement is shown. To minimize the amount of tubes and connections the valve and the pump is mounted on a manifold which contains all connections. This manifold is preferably designed without dead volume and easy to clean as it preferably will be cleaned every time the tubes are exchanged (every 6 months). The two dosage pumps 95, 96 are preferably precision solenoid membrane types. The valve 99 is preferably a 3/2 rocker solenoid valve with minimized dead volume.

The tubes 97 preferably comprise tubes for inlet and outlet of diluent as well as a tube for dosing.

The tubes 98 preferably comprises tubes for main line in and main line to drain also shown in FIG. 72.

Figure 77:
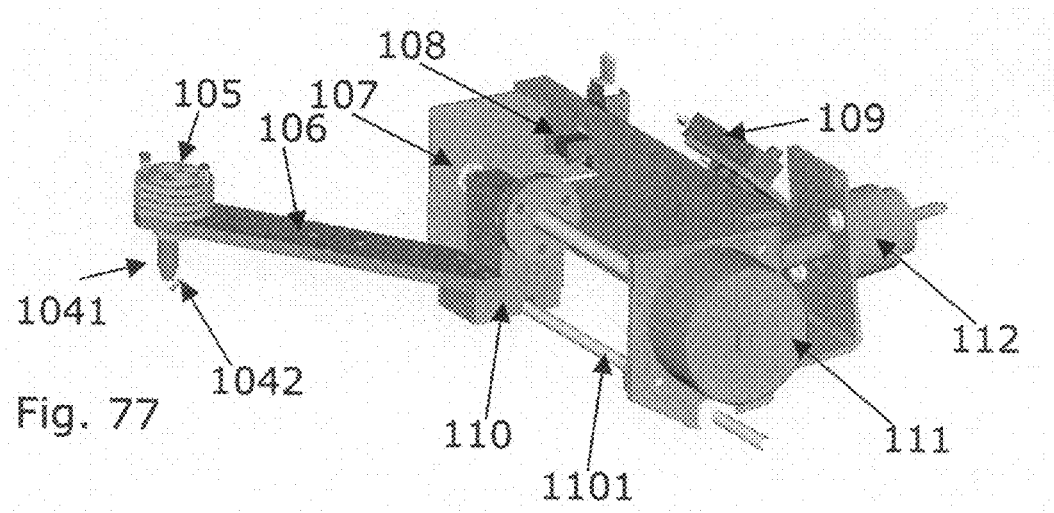
FIG. 77 shows an embodiment of a dosage device comprising a spindle, sensors, motors, dosage head and dosage arm.

FIG. 77 shows a part of the wet system comprising a dosage head 105 comprising holes for mounting of temperature sensor, a heater in form of a resistance, a hole for diluent to the diluent needle and a hole for the sample to the dosage needle.

Furthermore the wet system comprises a dosage needle 1041, comprising a cuper cap for warming the sample to body temperature, a diluent needle 1042, a mounting frame preferably fastened to the beam 46, a sensor 108 for sensing preferably a home position, a sensor for sensing a tilting position, a support bar 1101 for linear movement of the slide 110, a stepper motor for 111 for movement of the slide and thus the dosing head, a stepper motor 112 for performing the tilting movement of the arm 106 and dosage head 105 illustrated in FIG. 74.

Figure 78:
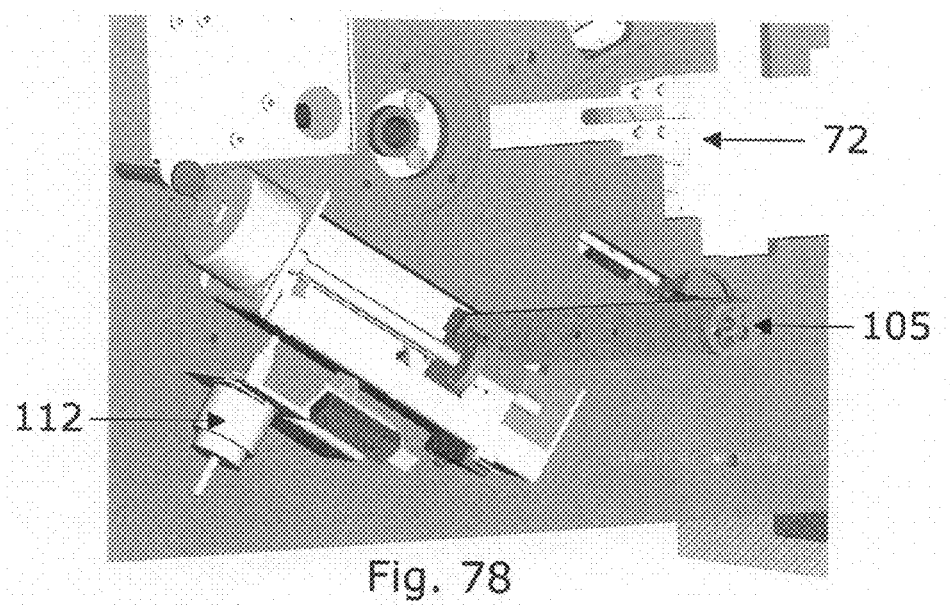
FIG. 78 shows the dosage device mounted on a central beam above the incubator disc.
Figure 119:
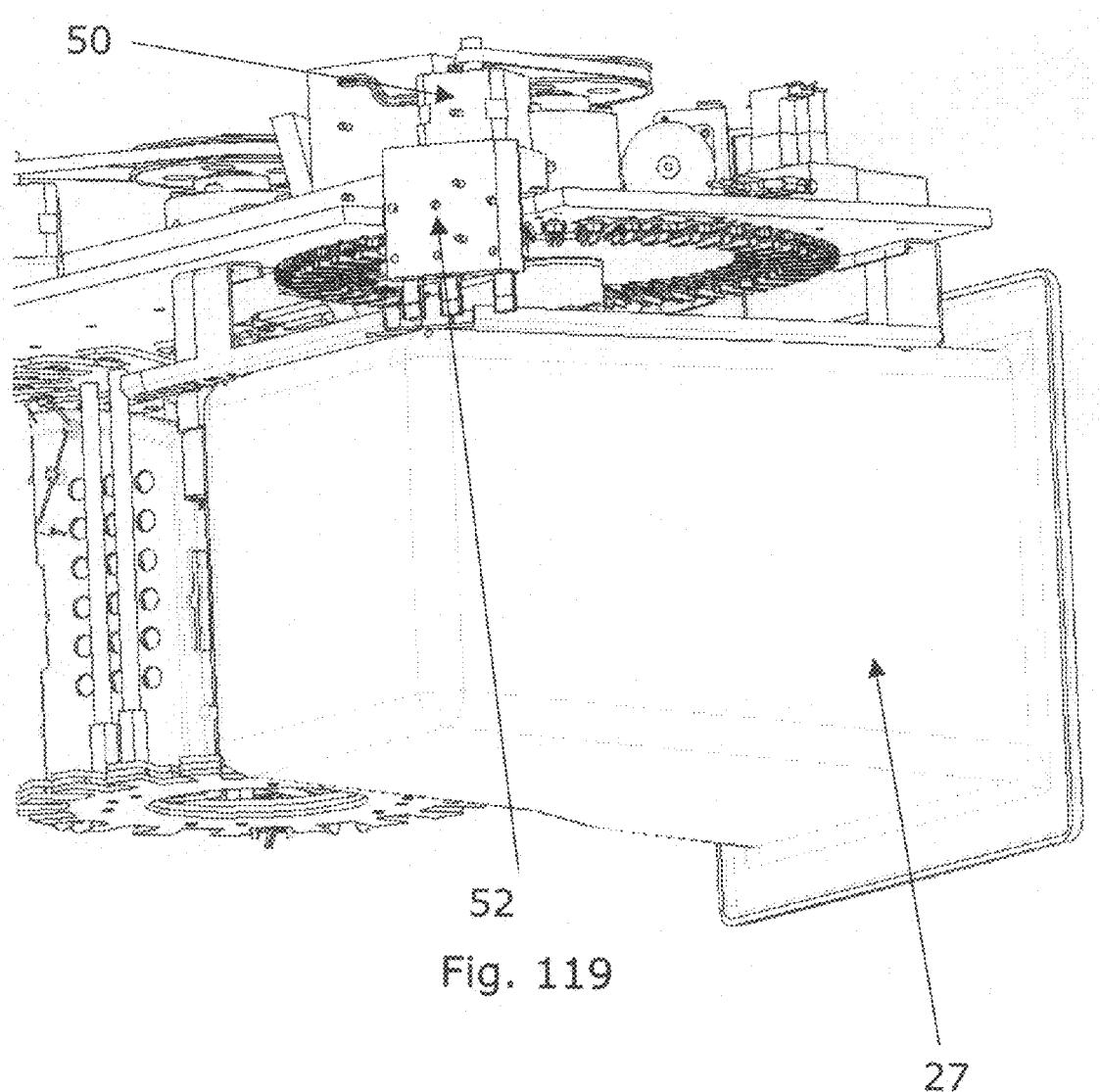
Figure 120:
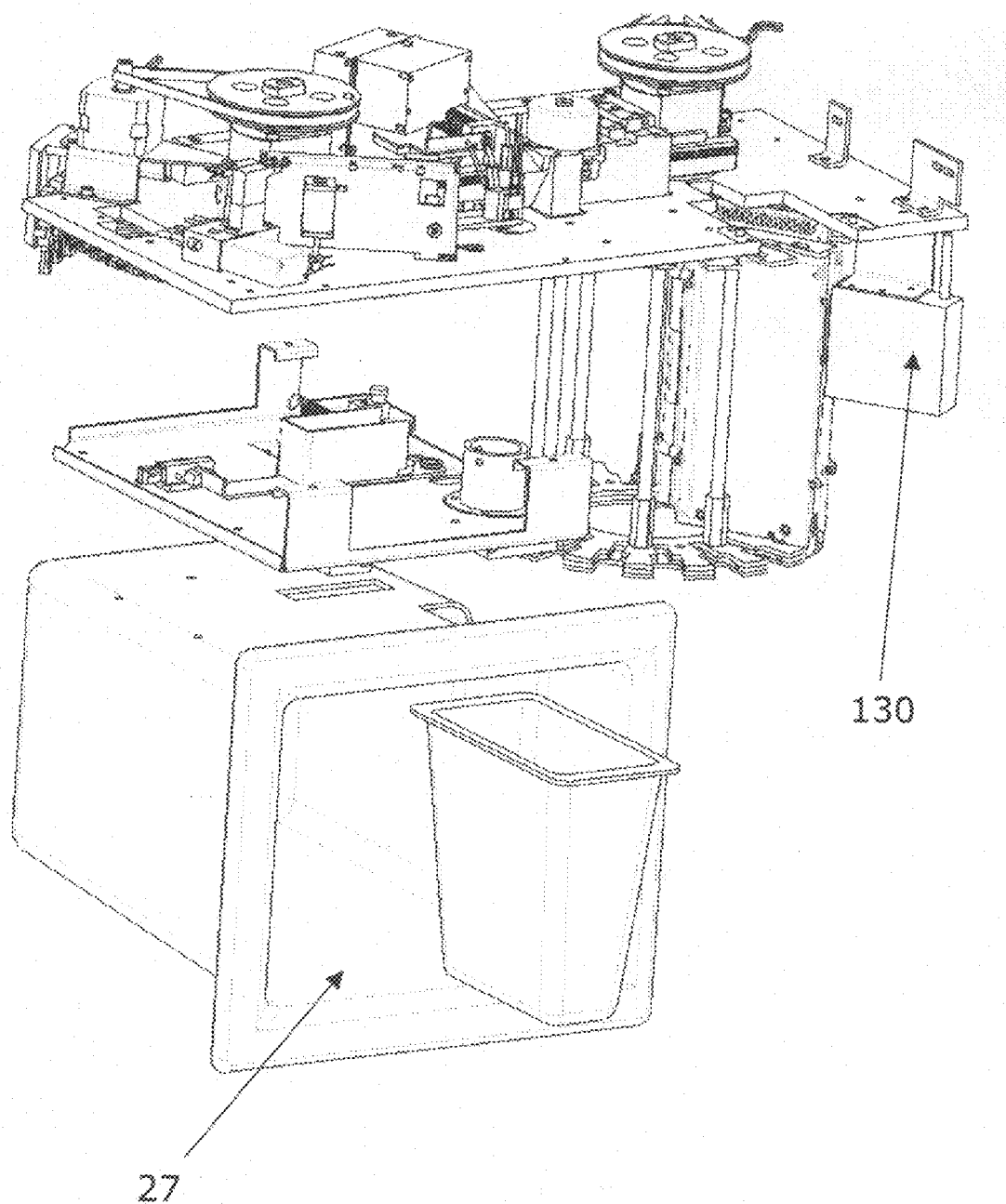

The two main types of sticks, colorimetric 250 and lateral 251, shown in FIG. 46, are placed in the incubator disc in positions where reading with the optical reader is done at the same radii. Because of this, dosage has to be done at two different radii. Additionally the dosage has to move to two positions in the drain funnel. The movement between these four positions is obtained with a spindle. In FIG. 78 it is shown how the spindle arrangement with the dosage head 105 may be mounted to the beam above the incubator disc and the drain funnel. The dosage head 105 is preferably made so that the needles can be removed for cleaning through the drain funnel fixture, from within the consumable room 27, see FIGS. 119 and 120. This will make cleaning and inspection easy and open for the possibility of plugging in a special dosage metering tool. The dosage heating and temperature feedback is done by power resistant and a NTC resistant that are glued in the dosage head. If possible these elements are to be mounted on a small PC board and screwed on the dosage head. This is to simplify assembly and service.

Figure 76:
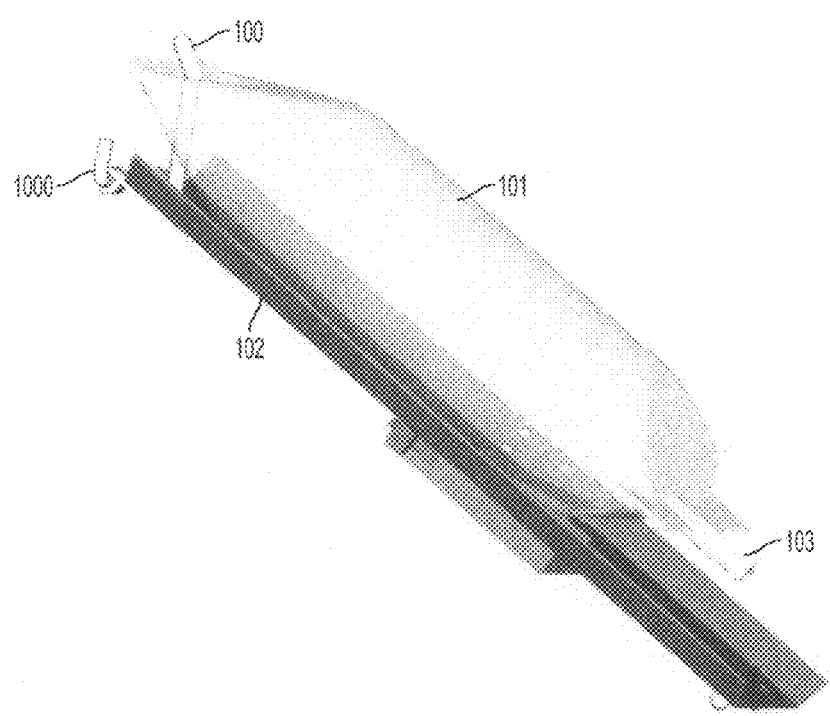
FIG. 76 shows a storage device and assembly for storage of diluent.

The diluent container is preferably to be kept on a ramp 102 in the consumables room, preferably with a low level switch that will signal when the diluent level is below a defined level, see FIG. 76. This level should preferably be defined as a little more than is needed for a full milking session. To monitor the diluent level more accurate the software should keep count on the amount pumped. Preferably the diluent container is hinged in one end 1000 and resting on a chute or plate 102 so that when the consumable room 27 is opened and the beam is moved to an opened position the chute is moved to a horizontal position making it easier for a user to access the diluent container and replace it with a new.

Preferably the diluent container 101 is a bag made of plastic or rubber or any other material useful for the purpose. The diluent container may preferably comprise a protrusion 103, membrane or the alike for penetration of a needle so that diluent may be pumped or sucked into the analysis apparatus.

The needle is preferably a standard syringe tip with luer connection, a suitable standard spike may also be used due to lower cost and convenience for the user.

Optical Reader

General Description

The optical reader module 8 (ORM) is a part of the MERKUR Analysis Instrument. It is an integrated part of the incubator module with the purpose of "reading" the degree of chemical reaction found on individual dry-sticks after milk has been applied.

Principle of Function

At present two different types of chemical reactions can be read.

Type 1: Calorimetric Field Reaction

In this case a milk sample is applied directly to the reaction field, which after some time will develop a colour change proportional to the amount of "tracer" in the sample.

Figure 103:
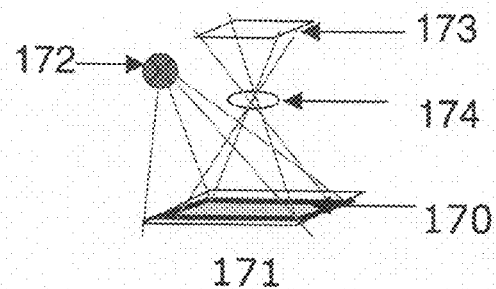
FIG. 103 shows schematically the optical reader for sticks comprising an object field and reaction field.

The measurement object field, which is identical to the reaction field 170, is illuminated with either green or red light, and the amount of reflected light is measured with a calibrated sensor. The average of reflected light from a defined part of the object field 171 is used as a measure for the amount of "tracer", see FIG. 103.

Type 2: Lateral Flow Test Line

In this case a milk sample is applied to a reception area, there after the milk is transferred to the reaction line 175.

Figure 104:
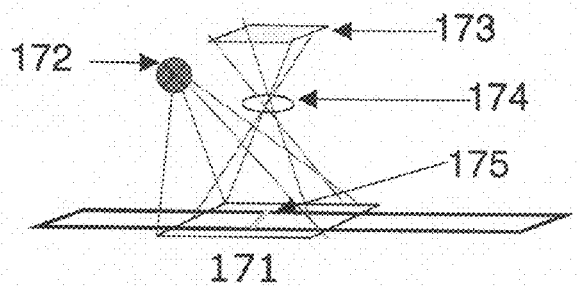
FIG. 104 shows schematically the optical reader for sticks comprising a reaction line and an object field.

The measurement object field 171, which includes the background substrate and the reaction line 175, see FIG. 104, is illuminated with preferably either green or red light, and the amount of reflected light is measured with a calibrated sensor. The strength of the reaction line is used as a measure for the amount of "tracer".

System Description

The ORM is a self-controlled unit capable of capturing an image of a view field 178 and to perform a calculation of reflected light in a defined object field 171 according to the type of object presented.

Figure 105:
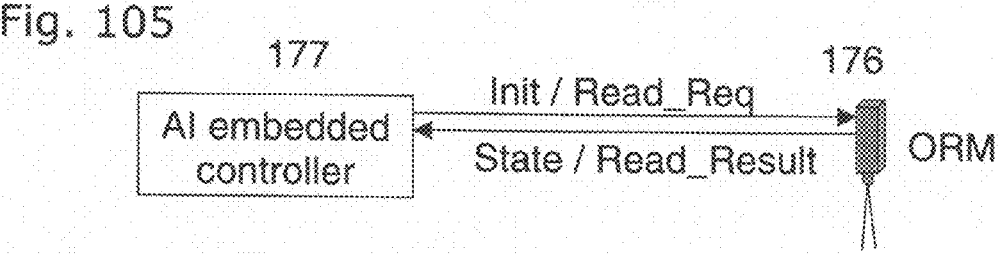
FIG. 105 shows the communication between the controller and optical reader.

The ORM context diagram can be seen in FIG. 105.

In one embodiment, before the ORM may be used for "reading" or after power-up the embedded controller. The AI 177 may send an initialisation string in order to set-up instrument dependent parameters (E.g. internal grey scale offset). The ORM 176 will respond with a state message.

However, in a preferred embodiment the ORM is calibrated independent of the AI embedded controller.

The AI embedded controller may request reading of an object after the object has been brought to a fixed position in the view field 178. The request preferably include object type and illumination wavelength. The ORM will return the calculated values if the image processing software recognises the object as one of the specified type. If not, the ORM preferably will return a result error message. The ORM will be ready for another reading immediately after returning the latest result.

Figure 106:
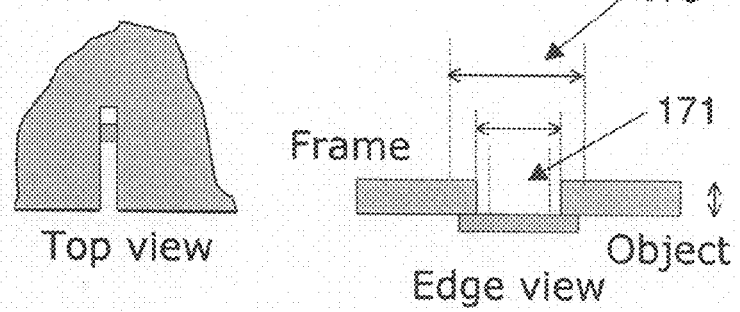
FIG. 106 shows the top and edge view of the object field and view field.

The view and object fields are illustrated in the FIG. 106, as well as in FIG. 107.

Basic design
General product design decisions

| | Design item | Design decision |
|---|---|---|
| | Functions | Type 1 and 2 reaction reading. |
| | Throughput/capacity | Read ratio preferably better than 2 seconds. |
| MORM020 | Image sensor 173 | National Semiconductors LM9617 Black and white |
| | Embedded processor | National Semiconductors LM9504 Image processor |
| MORM026 | Illumination 172 | Green 525 nm xxx 40° angle Red 660 nm xxx 40° angle |

Housing

The housing of the ORM is designed to fit into the physical frames dictated by the incubator module. FIGS. 108 and 109 shows the side and end view of an embodiment of the ORM house.

Figure 110:
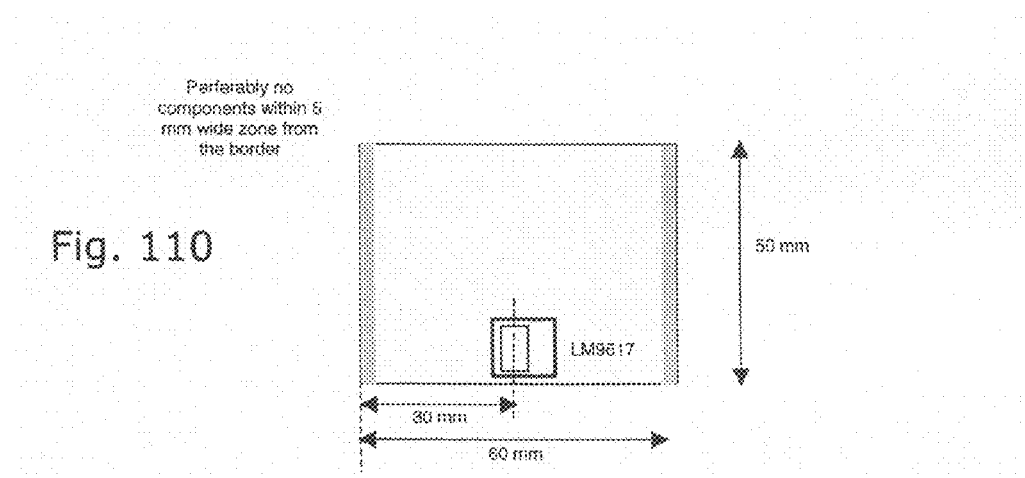
FIG. 110 shows a preferred placement of the image sensor relating to the second embodiment.

FIG. 110 shows PCB layout component side

Optical System

Figure 111:
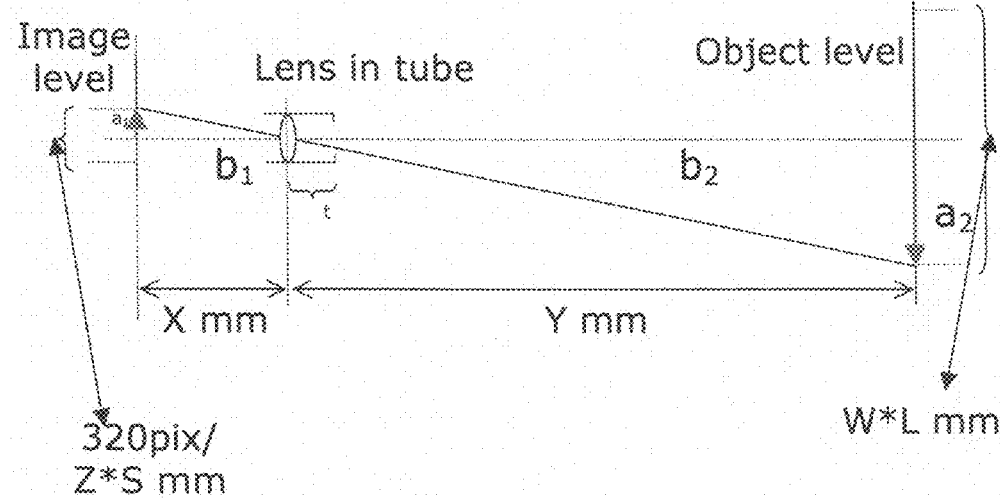
FIG. 111 shows schematically the relations within a second embodiment of an optical reader.

The basic idea of the optical design is illustrated in FIG. 111 as well. It is governed by the fact that the view area of 8*8 or 8*12 mm preferably is down-sized to a part of the sensor area of 4*5 mm of the imager sensor chip 173 from National semiconductors.

The image sensor 173 is preferably a standard VGA colour chip with the dimensions 3.66*4.86 mm and a resolution of 480*640 pixels. Using a square of 320*320 or 320*466 pixels gives image size of 2.4*2.4 or 2.4*3.5 mm on the chip surface, which again gives a magnification factor:

The representation of the variables in the following can be found in FIG. 111. f=Object size/Image size=8 mm/2.4 mm=3.3

$$a_2/a_1 = b_2/b_1 = f => b_2 = f*b_1$$

Given: $b_1 + b_2 = 90$ mm => $b_1 = 20.9$ mm and $b_2 = 69.1$ mm and $1/f = 1/b_1 + 1/b_2 => f = 16.0$ In another embodiment the representation of the variables may be:

$$a_2/a_1 = b_2/b_1 = f => b_2 = f*b_1$$

Given: $b_1 + b_2 = 84.8$ mm => $b_1 = 19.5$ mm and $b_2 = 65.3$ mm and $1/f = 1/b_1 + 1/b_2 => f = 15.0$ In one embodiment the preferred maximum forward lens tube length 176 may be: t=43.2 mm with a tube aperture of 5 mm Ø. The lens tube preferably comprises a lens 174.

Furthermore the housing preferably comprises screening walls 178, and a membrane 177 for closing of the housing.

Figure 113:
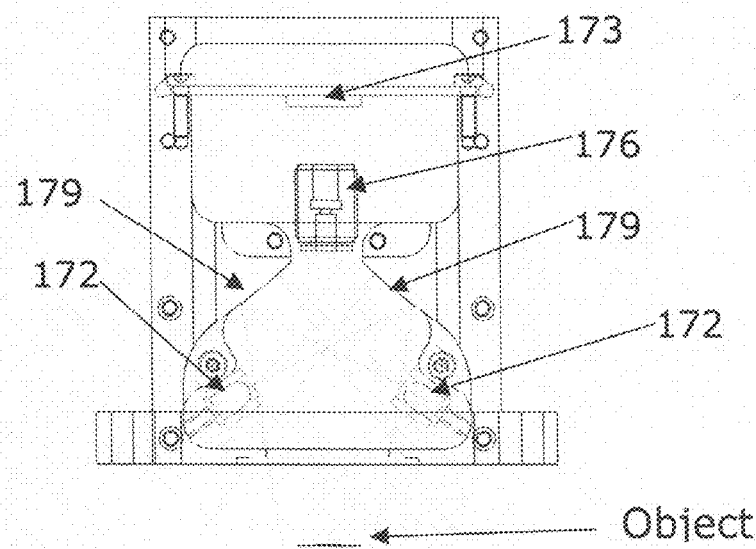
FIG. 113 shows a first embodiment of the optical reader.

In a first embodiment the illumination system of the ORM consist of the LED's 172 and a set of reflectors 179 integrated in the ORM housing. The light from the LED's is pointed at the reflectors and reflects as diffuse light on the object area, see FIG. 113. The light intensity is preferably controlled by a internal grey reference reading.

In another embodiment the illumination has been placed in the lens fixture close to the PC board in order to bring it as far as possible away from the object area and thus ensuring the least possible variance in reflected light if the object is slightly out of focus. In this embodiment it is preferably not necessary to control the light intensity.

Electronics

Figure 112:
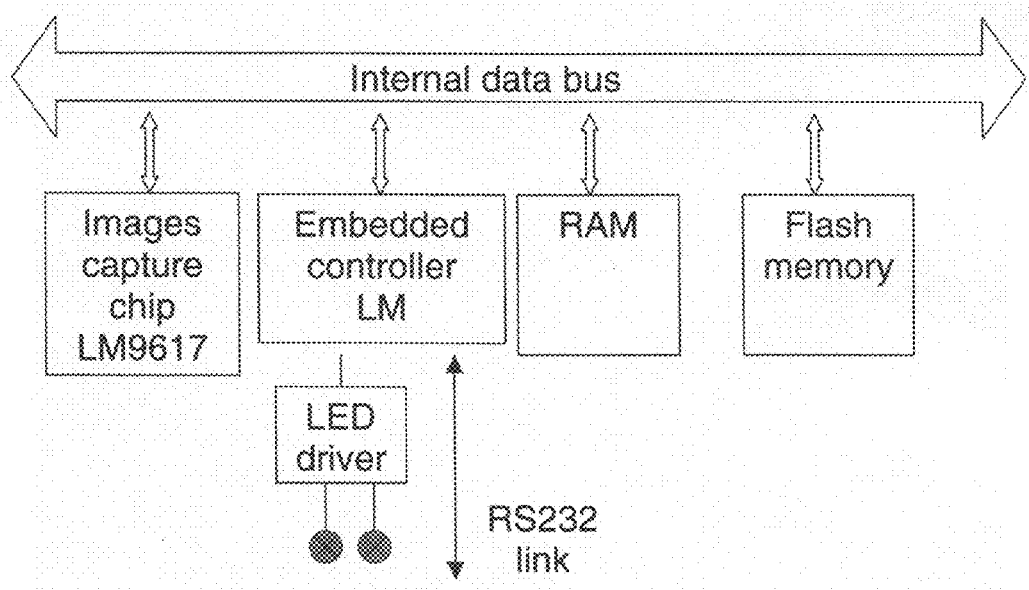
FIG. 112 shows a schematic diagram of the computer system for controlling the optical reader device.

An embodiment of the basic design of the electronics is shown in FIG. 112.

Images capture chip 173
    Embedded controller
    Internal signal interface
    External communication interface
    RAM The controller board is preferably equipped with Flash memory, which holds
A simple monitor including a boot loader and flash burner
The application program.
Control Software
Stick Waste The function of the stick waste is to receive the used sticks pushed out of the incubator by the stickmover. The system has a funnel leading to a container. The funnel has a built in hatch 141 that closes towards the used sticks. The hatch is moved by a DC gear motor 144, see FIGS. 91, 92, 94 and 95.
Detection of Stick Waste Full or Obstruction of Funnel The function of the detection device serves several purposes, firstly it provides detection of full waste container, in case it is not completely emptied by the operator, secondly the device is able to dissolve an obstruction in the chute, and the device can also function as an airlock between incubator and the surrounding environment.

Figure 91:
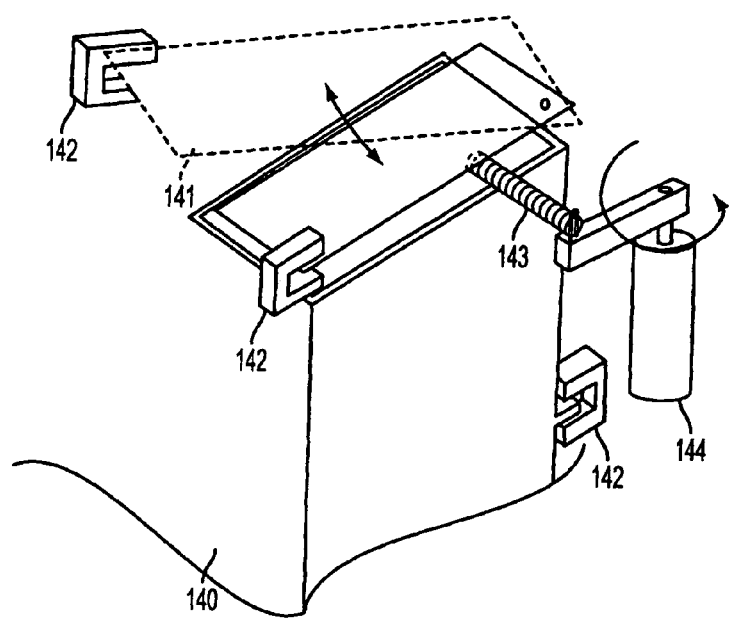
FIG. 91 shows a second embodiment of a waste storage device comprising: a hatch cover, sensors a driving assembly wherein the hatch cover is connected to the motor by a spring.
Figure 92:
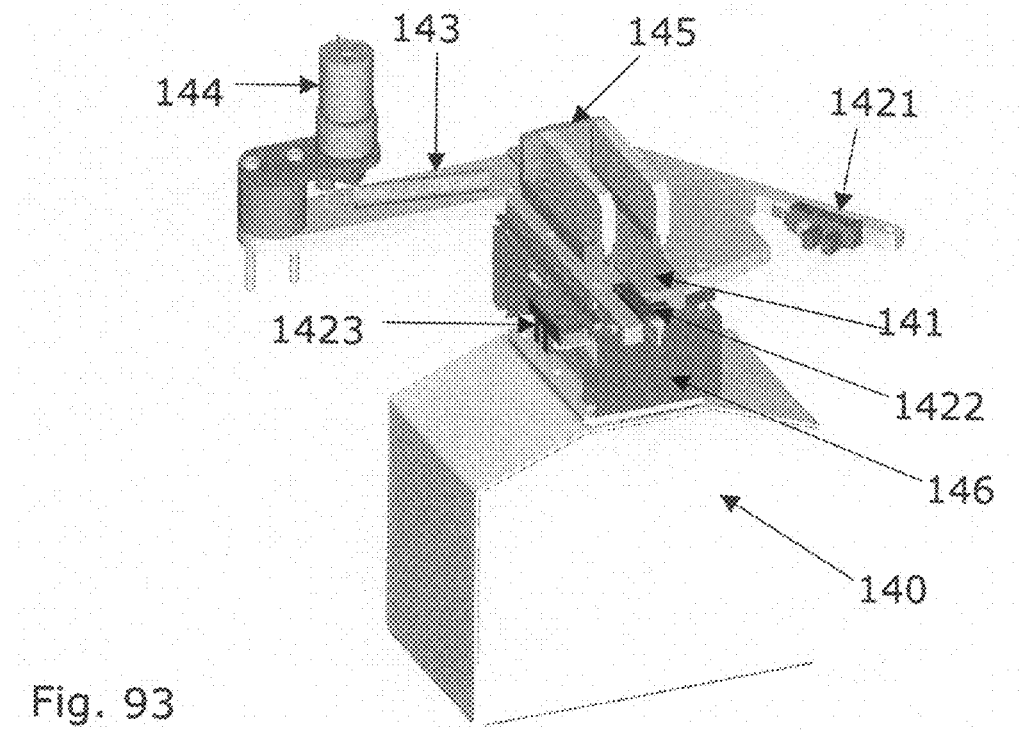
FIG. 92 shows a first embodiment of a waste storage device described in FIG. 91.
Figure 93:
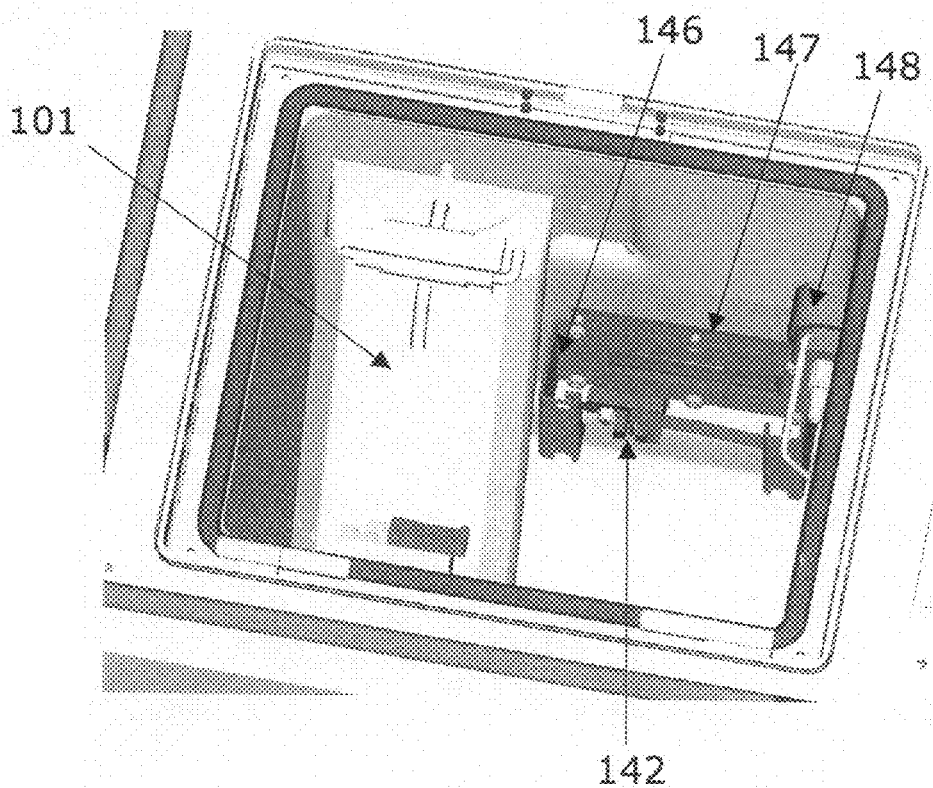
FIG. 93 shows a user interface wherein the waste funnel and the mounting of the diluent storage device is shown.
Figure 94:
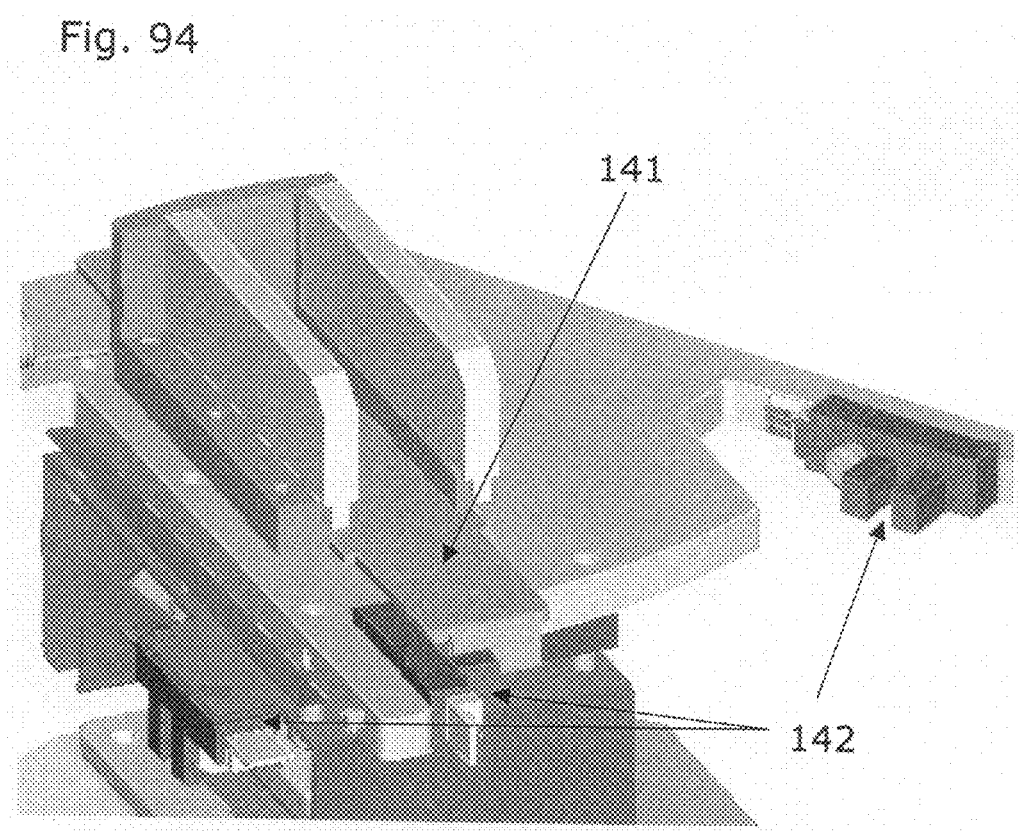
FIG. 94 shows an enlargement of the hatch cover and sensors on a waste storage device.
Figure 95:
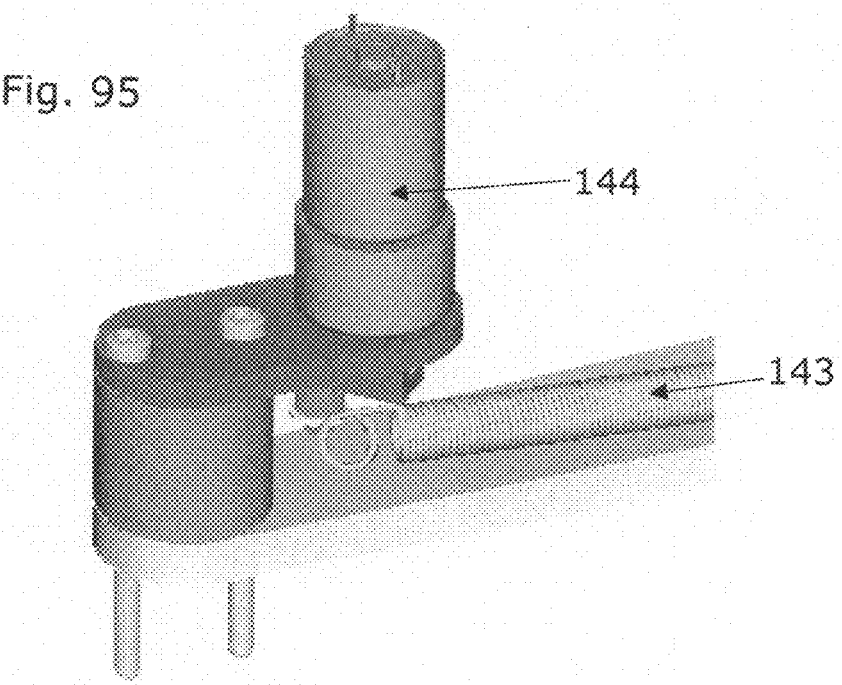
FIG. 95 shows the driving assembly for a hatch cover on a waste storage device.

Different solutions have been taken into consideration, but preferably a 'mechanical' solution gives the highest degree of confidence. The design intent, which is illustrated in FIG. 91, is to let a hatch cover 141, driven by a small DC gear motor 144 perform a sweeping motion across the gap between chute and waste container 140, every time a stick is transferred from storage to incubator. The shaft of the gear motor has a crankshaft connected to a pretensioned spring 143. As the shaft only rotates in one direction, the spring will pull the hatch cover 141 positively to a stop when closing, and push the hatch cover when opening motion is called upon. Should an obstruction occur, the hatch cover will stop at it, and the spring 143 will allow the crankshaft motion to continue, until the hatch cover is moved away from the obstruction, thereby tripping the 'airlock open' sensor 142. Sensors (photo interrupters) 1421, 1422 at each end of the hatch cover's travel path will detect, if an obstruction has taken place, and notify the operator. A sensor 1423 detects if the waste container is in place, and resets the used stick counter.

The waste container 140 is preferably mounted in the apparatus by inserting it into a docking station 146. A plate 147 may be used for mounting.
Function During Normal Behaviour:

1) The number of used sticks are monitored and accounted for by the AI.
2) When xx units of sticks have been processed, the operator is notified about the fact that the waste container should be emptied soon, for instance when the milking session is completed, as there is enough space for additional used sticks, to complete a milking session.
3) The operator empties the waste container, and as he replaces it correctly, the used stick counter is reset.
Function During Unusual Behaviour
(Case 1) (Step 1 Through 2 as in Normal Behaviour):
3) The operator does not empty the waste container completely, and sets it back.
4) The 'waste container in place' sensor resets the stick counter.
5) The waste container will now be filled, before xx number of sticks is reached, and sticks will protrude up through the airlock between chute and waste container.
6) The level detection senses 3 out of 3 consecutive times that an obstruction has occurred.
7) A beacon lights up to alert the operator.
8) Sticks will no longer be transferred, but sticks already transferred to the incubator will be processed (milk will be dosed, and the reader will collect the data).
9) The operator comes to the AI, and empties the waste container. As he opens the front cover in the outer cabinet, the hatch cover sweeps away from the gap, thereby permitting any jammed sticks to drop into the container.
10) As the empty waste container is returned to its position, the stick counter is reset as the 'waste container in place' sensor is tripped. Behaviour can restart at 1).

| Control strategy of waste level detection | | | |
|---|---|---|---|
| Action | Sensor 1 Airlock closed | Sensor 2 Airlock open | Sensor 3 Container in place |
| At stand-by | 1 | 0 | 1 |
| At stick transfer into incubator and/or stick to waste, the DC-gear motor is turned on until S2 is interrupted at which point the motor is turned off. | 0 | 1 | 1 |
| After a short delay the motor is turned on to return hatch cover. When S1 is interrupted the motor is turned off. | 1 | 0 | 1 |
| In case there is an obstruction (a stick in chute) S2 will be interrupted instead. Is S2 interrupted 3 times the motor is turned off at S2 interrupted to leave the airlock chute open. The alarm is turned on to call operator to empty waste. | 0 | 1 | 1 |
| Power-up: S1 interrupted - no action needed. If not interrupted the motor is turned on until it is. | — | — | 1 |

Figure 50:
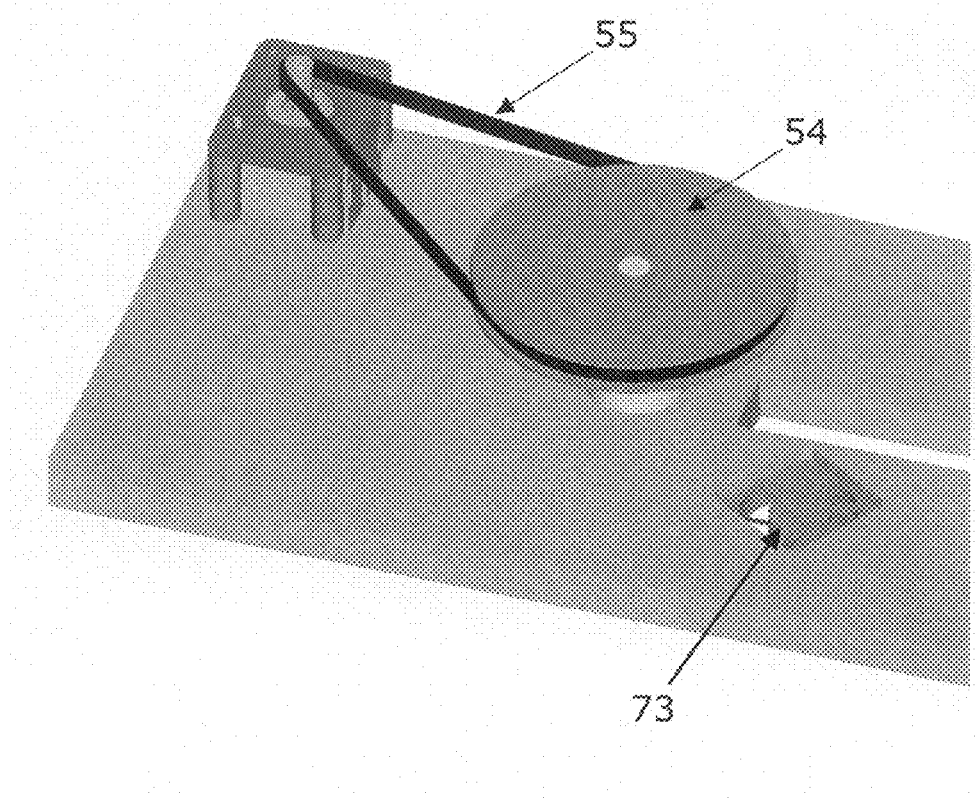
FIG. 50 shows a second embodiment of driving assembly for the incubator further illustrating a fan for preferably warming of the sticks.

Function During Unusual Behaviour
(Case 2) (Step 1 Through 2 as in Normal Behaviour):
3) The operator does not react at all to the warning.
4) When the waste container is filled with xx+yy sticks, the pattern will be as from 6) through 10).
An Embodiment Wherein Thermal Conditioning of Stick is Used
Function of the Thermal Conditioning The sticks are preferably kept in storage at 20° C., before they are transferred to the incubator, where they preferably achieve a temperature of at least 30° C., before dosing in order to avoid milk fat depositing on the sample. Since the temperature inside the incubator module preferably is 37° C., one way of achieving the heat-up of sticks, would simply be to let them cure from slot number 1 (transfer slot) to the dosing slot. Tests have shown that for a calorimetric stick, it takes ~40 s to rise from 20° C. to 30° C. by natural heat convection, while it only takes ~15 s when forced convection is applied by means of a small fan 73. If natural convection was to be used, it would require 6 spaces, and dosing would take place at slot number 7. The same test on a lateral stick showed that 30° C. could be reached within 20 s with the fan. To reduce the size of the incubator (and therefore the size of The Merkur Analyser), forced ventilation may be chosen. As the total elapsed time for a complete revolution of incubator is preferably 5 min (300 s), 4 spaces will give sufficient time (~27 s) for the temperature to rise.
Applied Solution A small fan 73 integrated in the upper beam, illustrated in FIG. 50, directs the airflow towards the 4 slots that lies between transfer slot and dosing slot.
Preferred Data and Specifications:

| Description: | DC brushless fan |
|---|---|
| Dimensions: | 50 × 50 × 10 |

| | |
|---|---|
| Rated voltage: | 12 V |
| IP: | 25 |
| Air flow: | 7.3 cfm(at 1.8 mm H$_2$O) |

Dry Stick Frames

Function

Figure 70:
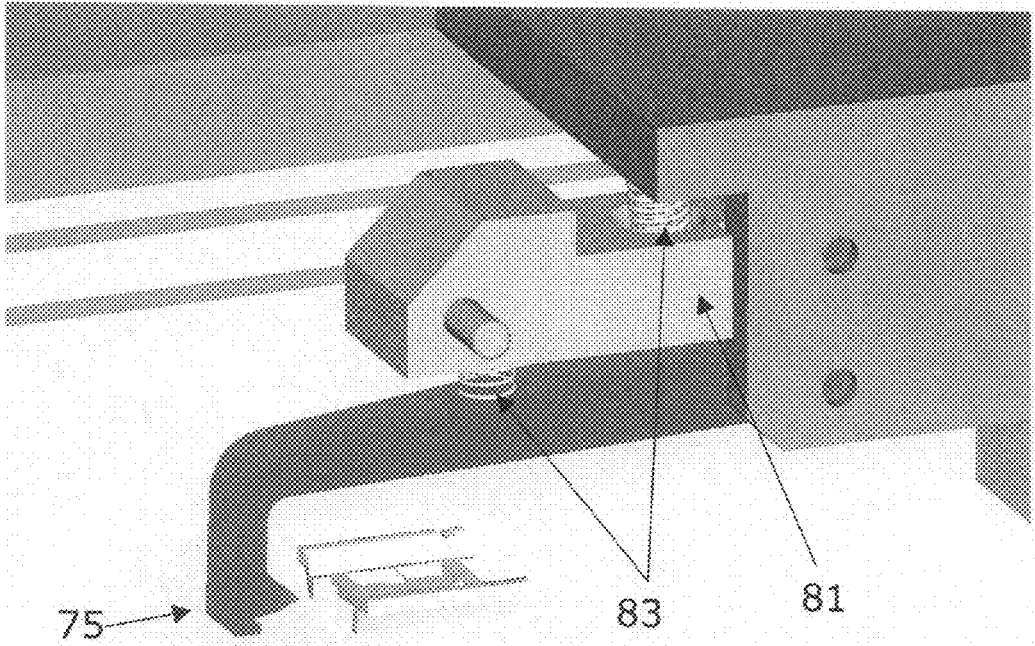
FIG. 70 shows an enlargement of the stickmover pawl and the suspension.
Figure 71:
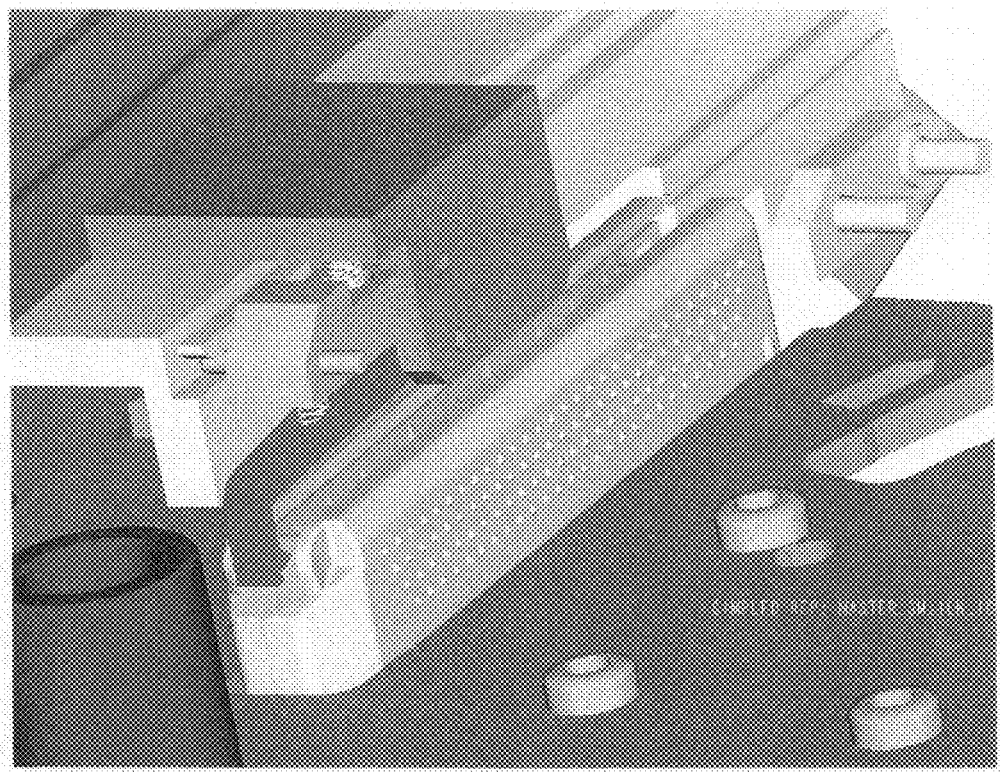
FIG. 71 shows the stickmover pawl catch a stick of a first type from a cartridge.

The stick frames shown in FIGS. 46 and 70 provide handleability to the chemistry pad.

The path of handling from production to waste is:

Frame is manufactured by injection moulding.

Pressing the pad into the frame assembles chemistry pad and frame, now forming a dry stick [DS].

DS are stacked in appropriate numbers and inserted in cartridge. A formed sheet of stainless steel is inserted under the stack forming a no-return floating bottom, securing the stack at any stack height, shown in FIG. 100.

Cartridge is wrapped in protecting seam-welded bags, packaged in boxes and put on stock, while kept cold at 5° C.

Box is transported and distributed to the end-user, still kept cold.

Box is received by end-user and put in refrigerator.

A single cartridge is retrieved from box and brought to AI, inserted in AI-storage, after removal of bag, to replace an emptied cartridge.

The storage temperature is kept at 18° C. and the humidity is kept below 30% RH.

The storage turntable presents the cartridge to the stick-mover when a DS of that specific constituent is desired.

The pawl of the stick-mover sweeps out a DS from the top of the cartridge, through a tunnel between storage and incubator turntables, and into a slot of the incubator, shown in FIGS. 63-67. The DS is ejecting a used DS from the slot, when inserted. The used DS falls into a waste container, which is emptied by the user at appropriate intervals.

As a DS is removed from the cartridge the stack jumps up to present next DS, by means of springs located in the storage. These springs were compressed at the insertion of the cartridge.

The incubator turntable has 45 slots, indexing one slot each ~8 sec, presenting the DS to the dosage module and reader. The slots form a guide way, with integral springs pressing the DS against the underside of the incubator, reducing the number of elements in the chain of tolerances.

While indexing from point of stick-insertion to point of dosage, the temperature of the DS is raised to minimum 30° C., by forcing a flow of 37° C. warm storage air to pass over the DS. A DS temperature of 30° C. is desired to prevent the milk-fat from changing properties when dosed onto the chemistry. Position 1 through 4 is allocated for warming the DS.

At position 5 the DS is presented to the dosage-module. The dosing head is formed by needle-tubes or the alike, which preferably are brought in contact with the chemistry while the volume of milk is dosed. In case of a lateral flow stick [LS] for progesterone a volume of thinner solution is dosed simultaneously.

In the course of indexing from point of dosage to point of reading the 5 minutes of incubation takes place.

At the reader the DS is presented and a picture is taken, whilst illuminated with the appropriate wavelength.

The chemistry has two formats, lateral 251 flow and colorimetric 250:

The lateral flow chemistry consists of a bottom foil with nitrocellulose and glue on which dosage, reaction and suction fiber pads are placed. A tape is placed on top, except at the dosage area. The chemistry is 5 by 60 mm and up to 1.6 mm high. The position of the reader-line is approximately in the middle. At the moment it is uncertain whether it is 35 mm or 25 mm from the leading edge.

The calorimetric chemistry is formed by a 5 by 5 mm fiber-pad. At the moment the pad is expected to be 0.34 mm thick.

Applied Solution

Material.

Polystyrene [PS] has been chosen as it has a low cost per volume and a high stiffness modulus. Furthermore it has a high surface tension towards milk, higher than Polyethylene [PE], reducing the risk of the milk seeking out in the gap between frame and chemistry, shown in FIG. 45.

Manufacture of Frames

The frame is injection moulded. The geometry can be realized in injection tooling, without complexity e.g. separately moving cores etc. Due to the waste numbers needed, the production tooling will have several cavities—maybe as many as 64, and will utilize hot-runners and micro injection-nozzles. The tooling produce no runners and inlet-parts, meaning that there is need to separate and recycle scrap.

The point of injection is placed in an indention of the geometry to allow some degree of undefined geometry.

The ejection pins are slightly prolonged, 0.05 mm, so that wear and tolerances can be taken-up without causing protrusions on the frame.

The stick assembling equipment checks each frame for faults, e.g. dimensions exceeding tolerances and incomplete geometry, and expels faulty frames. This could be done utilizing vision systems and/or laser grids.

Assembly and Securing Chemistry

The chemistry is mounted in the frame simply by a pressing motion with an appropriate shaped plunger. No-return hooks placed on the walls of the frame secure the chemistry by positive engagement, shown in FIG. 71.

The bottom plastic foil of the lateral chemistry flips under the hooks, although it has cut/deformed to some degree. Frame were realized in soft tooling and assembly of chemistry carried out. It was found that the chemistry at the reader-line did not relate to the bottom of the frame as it bended, which affects the focus/precision of the reader. Therefore rib-protrusions are added, which have a transversal distance smaller than the width of the chemistry, thus retaining the pad.

The calorimetric fiber pad is partly formed around and under the hooks, thus retained.

The first calorimetric frame, that were designed and produced, had the chemistry inserted from underneath. This design presents the top of the chemistry with less tolerance of the level, has a higher flexibility regarding different/changing pad thickness and less critical retaining function, as the hooks have a better leading angle. The design was changed to the present as the concept of dosage has changed from non-contact to positive contact of the needles to the chemistry, which calls for support from underneath of the pad.

Geometry of Frames:

The design of the frames aim to have:

Lowest possible cost

Ease of automated production

High reliability of AI—avoid malfunctions and influence of the precision of measurements Small physical dimensions Ease of disposal Lowest possible environmental impact Ease of development, same design paradigm for both frames Same level of dosage for both DS Same level of reading for both DS Geometry Relations:

All three sides of the wings relates to stick-mover tunnel guide way, incubator slot and disc.

Upper surface, sides and end surfaces of wings relates to cartridge.

Top, bottom and ends of frame relates to other frame in cartridge and at ejection of used DS from incubator slot.

Bottom relates to no-return floating bottom-part of cartridge.

Withdrawn end-walls relates to stick-mover pawl.

Cavity and hooks relates to chemistry.

Frame relates to waste chute, waste full detector and waste container.

Frame presents chemistry to dosage module and reader.

The overall height, 2.5 mm, of both frames is determined by the LS, as the chemistry is thicker—at this point of time 1.6 mm. The floor of the LS-frame is 0.6 mm thick, leaving a clearance of 0.3 mm from the top of the frame to the chemistry. The stack-height of the LS is the full 2.5 mm. The stack-height of the CS is reduced to 1.4 mm, by reducing the thickness of the frame body, utilizing the thinner chemistry.

The wings of the frame allow the DS to be guided in the stick-mover tunnel and incubator slot. The guide ways are formed like [ ]-tracks, 1 mm high and 0.8 mm wide.

The stick-mover pawl pushes the stick on its end-wall. The end-wall has a shelf-like protrusion that engages with the stick-mover pawl, preventing it from sliding of and over. The wings are extended beyond the end walls of the frame. This makes room for the stick mover pawl when the next DS jumps up in the cartridge when a stick is swept out.

Dry Stick Cartridge

Function

It is important that calorimetric as well as lateral sticks are guided securely and that they are as easy to handle as possible all the way from production until use in the apparatus. The vertical guidance has to be so robust that the sticks are not erroneously oriented, before they are taken out of the stick mover horizontally. It is necessary for the cartridge to be designed in a way that enables the stick mover to run into an integration surface and be presented to sticks in the same way each time.

Under production, transportation and handling the cartridge with sticks, the cartridge has to be able to withstand all possible ways of handling, which may include pushes, strokes and even drops, but which must not make the sticks be erroneously oriented. The LC (lateral cartridge) preferably contains 50 sticks, and the CC (calorimetric cartridge) preferably 100 sticks.

Applied Solution

Due to various physical designs of colorimetric and lateral sticks, two types of cartridges are available. The two types are called Colorimetric Cartridge [CC] and Lateral Cartridge [LC], respectively. Apart from the depth, the two cartridges are almost identical.

A cartridge consists of two injection-moulded shells, which have been ultrasonic welded together. The shells are made of impact modified PS, which has been chosen due to the favourable price and the mechanical qualities desired, both regarding strength/stiffness and welding.

In the following, the cartridge and the parts, which have integration for the cartridge, are described more closely and will apply for both the CC and the LC.

Ultrasonic Welding

A cartridge consists of two injection-moulded items, which have been ultrasonic welded together, see FIG. 101.

Each shell has three energy directors, (six per cartridge), which have been placed male/female alternately.

The welding takes place by way of a specially manufactured welding horn and a fixture on a 20 kHz welding machine.

The welding time including fixing time is approx. 1.5 second.

In the production the welding may take place fully automated inline with an injection-moulding machine.

Vertical Guide-Way:

Nominal air around the stick is 0.15 mm all the way round (0.3 mm in each direction).

The width of the guide in the edge is 1.2 mm.

To make sure that the sticks can be handled smoothly without being squeezed by the cartridge and without capsizing (lateral sticks have a tendency of that), the welding has to be as precise as possible.

Cartridge, Spring Lock:

To ensure that the sticks cannot be removed from the cartridge in case of shocks when handling, they are held back by a spring lock built into the item. Shown in FIG. 101.

The blocking of the spring locks can only be removed, when the stick is taken out of the stick mover.

Preferred Data and Specifications

Welded in impact modified PS

Good mechanical properties

Suitable for ultrasonic welding

Inexpensive material, approx. DKK 8 per kilo

Physical data, LC:

Volume: $2 \times 21500$ mm$^3$

Weight: $2 \times 22.6$ g

Main dimensions (L×W×D): $160 \times 13.2 \times 25$ mm

Physical data, CC:

Volume: $2 \times 8200$ mm$^3$

Weight: $2 \times 8.6$ g

Main dimensions (L×W×D): $160 \times 13.2 \times 25$ mm

Floating Cartridge Bottom

Function

To ensure that the sticks in the cartridge are always in the top of the cartridge, and that the stack of sticks is kept in place, the bottoms, such as the one shown in FIG. 100, have been used.

Applied Solution

The item has been made of bent sheet metal, so that its shoulders are flexible and act as a lock. The lock runs against four internal one-way stairs in the cartridge. Items for function models have been made of stainless steel by way of laser cutting and bending.

When the cartridge has been emptied for sticks, and the bottom is in the top of the cartridge, a 45-degree bend ensures that the stick mover pawl will slide over the bottom. The bottom is guided between the four legs and the side-guidance of the stairs shown in FIG. 100.

Data and Specifications 0.10 mm stainless spring steel, AISI 301

Laser cutting/photo etching items for function models

Bended in specially manufactured tools

Loading Sticks in Cartridge

The Sticks are Mounted in the Cartridge in the Following Way:

A bottom is placed in a temporary fixture.

50 lateral or 100 colorimetric sticks are placed in the fixture. The recesses in the end of the stick guide the sticks.

The cartridge is taken down to the fixture. The bottom gets in contact with the one-way stairs in the shells.

To get the sticks to the top of the cartridge, the cartridge is held, while the auxiliary plate of the fixture is being pushed upwards.

To secure that the stack of sticks are kept in place, cartridges may be loaded and unloaded in a keeper.

The invention claimed is:

1. A method for analyzing milk, which utilizes an apparatus comprising: (i) at least one storage for storing sticks or other kinds of biosensors to which the milk is to be dosed, wherein the storage is enclosed in a first insulation enclosure thermally insulating and moisture protecting the storage; (ii) at least one incubator, distinct from the storage, that comprises a first fluid dosing means for dosing a stick or biosensor with the milk to be analyzed, wherein the incubator is enclosed in a second insulation enclosure thermally insulating the incubator; (iii) a transfer mechanism for transferring sticks or biosensors from the storage to the incubator, wherein the transfer mechanism comprising a guide tunnel with a hatch for opening and closing the guide tunnel; and (iv) an incubator disc configured for guiding sticks or biosensors during the incubation, wherein the apparatus is sealed in a cabinet, said method comprising:
(a) loading sticks or biosensors into the incubator;
(b) dosing milk to the sticks or biosensors;
(c) incubating the sticks or biosensors in the incubator;
(d) reading the results from the sticks or biosensors; and
(e) removing the sticks or biosensors from the incubator, wherein (a)-(e) are performed upon at least one rotation of the incubator disc.

2. A method according to claim 1, wherein the apparatus further comprises a second fluid dosing means for dosing a fluid other than milk to the sticks or biosensors.

3. A method according to claim 1, wherein the incubator further comprises a reading module for detection of a signal produced on the stick or biosensor after application of the fluid.

4. A method according to claim 1, wherein the storage comprises a storage disc.

5. A method according to claim 1, wherein the apparatus further comprises sensors for monitoring the number of used sticks.

6. A method according to claim 1, wherein the apparatus further comprises a molecular sieve or other desiccant type for conditioning humidity content in the storage.

7. A method according to claim 1, wherein the apparatus is connected to a computer system.

8. A method according to claim 1, wherein the apparatus is connected to a user interface comprising at least one element selected from the group consisting of:
a keyboard;
a screen;
a cartridge loading station for loading cartridges;
a stickwaste container loading station;
a diluent container loading station;
a liquid waste funnel cleaning station; and
a wet system filter changing station.

9. A method according to claim 1, where the storage and the incubator are thermally isolated from each other to avoid or limit humidity or heat exchange between the storage and the incubator.

10. A method according to claim 1, wherein the first dosing means is driven by a spindle or other linear or rotational system for dosing milk at least two different locations.

11. A method according to claim 1, wherein the apparatus is configured for cooling or heating.

12. A method according to claim 1, wherein the incubator further comprises at least one sensor for monitoring the position of a stick in the incubator disc so that the stick is positioned correctly.

13. A method according to claim 1, wherein the apparatus further comprises tubes for transportation of milk.

14. A method according to claim 13, wherein the apparatus further comprises a device for minimizing carry over from a first sample to a second sample by introducing air into the tubes.

15. A method for analyzing a fluid, which utilizes an apparatus comprising: (i) at least one storage for storing sticks or other kinds of biosensors to which the fluid is to be dosed, wherein the storage is enclosed in a first insulation enclosure thermally insulating and moisture protecting the storage; (ii) at least one incubator, distinct from the storage, that comprises a fluid dosing means for dosing a stick or biosensor with the fluid to be analyzed, wherein the incubator is enclosed in a second insulation enclosure thermally insulating the incubator; (iii) a transfer mechanism for transferring sticks or biosensors from the storage to the incubator, wherein the transfer mechanism comprising a guide tunnel with a hatch for opening and closing the guide tunnel; and (iv) an incubator disc configured for rotation to position and guiding sticks or biosensors during the incubation, wherein the fluid dosing means is located inside the incubator, said method comprising:
(a) loading sticks or biosensors into the incubator;
(b) dosing the fluid on to the sticks or biosensors;
(c) incubating the sticks or biosensors in the incubator;
(d) reading the results from the sticks or biosensors; and
(e) removing the sticks or biosensors from the incubator, wherein (a)-(e) are performed upon at least one rotation of the incubator disc.

* * * * *